(12) United States Patent
Lambowitz et al.

(10) Patent No.: US 6,306,596 B1
(45) Date of Patent: *Oct. 23, 2001

(54) METHODS FOR CLEAVING SINGLE-STRANDED AND DOUBLE-STRANDED DNA SUBSTRATES WITH NUCLEOTIDE INTEGRASE

(75) Inventors: Allen M. Lambowitz, Austin, TX (US); Steven Zimmerly, Calgary (CA); Huatao Guo; Georg Mohr, both of Austin, TX (US); Clifford James Beall, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/257,770

(22) Filed: Feb. 25, 1999

Related U.S. Application Data
(60) Provisional application No. 60/076,161, filed on Feb. 26, 1998.

(51) Int. Cl.⁷ .............................. C12Q 1/68; C12P 19/34; A01N 43/04

(52) U.S. Cl. ...................... 435/6; 435/91.31; 435/91.1; 435/91.51; 514/44

(58) Field of Search .......................... 435/6, 91.31, 91.1, 435/91.51; 514/44

(56) References Cited

U.S. PATENT DOCUMENTS

| | | | |
|---|---|---|---|
| 5,498,531 | 3/1996 | Jarrell ................................ | 435/91.31 |
| 5,698,421 | 12/1997 | Lambowitz et al. ................ | 435/91.1 |
| 5,804,418 | 9/1998 | Lambowitz et al. ................ | 435/69.1 |
| 5,869,634 | 2/1999 | Lambowitz et al. ................ | 536/23.1 |
| 6,027,895 | * 2/2000 | Lambowitz et al. ..................... | 435/6 |

FOREIGN PATENT DOCUMENTS

WO 98/23756   6/1998 (WO).

OTHER PUBLICATIONS

"Group I and group II introns" by Saldanha, et al., *The FASEB Journal*, vol. 7, Jan., 1993, pp. 15–24.

"Group II Intron Mobility Occurs to Target DNA–Primed Reversed Transcription" by Zimmerly, et al., *Cell*, vol. 82, Aug. 25, 1995, pp. 545–554.

"An Expanding Universe if Introns" by Belfort, *Science*, vol. 262, Nov. 12, 1993, pp. 1009–1010.

"Integration of Group II Intron bII into Foreign RNA by Reversal of the Self–Splicing Reaction in Vitro", by Morl and Schmelzer, *Cell*, vol. 60, Feb. 23, 1990, pp. 629–636.

"A Group II Intron RNA is a Catalytic Component of a DNA Endonuclease Involved in Intron Mobility", by Zimmerly, et al., *Cell*, vol. 83, Nov. 17, 1995, pp. 1–10.

"RNA enzymes (ribozymes) as antiviral therapeutic agents" by Rossi ans Sarver, *Tibtech*, vol. 8, Jul., 1990, pp. 179–183.

"Mobile Group II Introns of Yeast Mitochondrial DNA Are Novel Site–Specific Retroelements" by Moran, et al., *Molecular and Cellular Biology*, vol. 15, No. 5, May 1995, pp. 2828–2838.

"Evolutionary relationships among group II intorn–encoded proteins and identification of a conserved domain that may be related to maturase function" by Mohr, et al., *Nucleic Acids Research*, vol. 21, No. 21, No. 22, 1993. pp. 4991–4997.

"Reverse Transcriptase Activity Associated with Maturase–Encoding Group II Introns in Yeast Nitochondria" by Kennell, et al., *Cell*, vol. 73, Apr. 9, 1993, pp. 133–146.

"Introns as Mobile Genetic Elements" by Lambowitz, et al., *Annual Reviews Biochem.*, vol. 62, 1993, pp. 587–622.

(List continued on next page.)

*Primary Examiner*—Lisa B. Arthur
*Assistant Examiner*—Jeanine Goldberg
(74) *Attorney, Agent, or Firm*—Calfee, Halter & Griswold LLP

(57) ABSTRACT

Methods, employing a nucleotide integrase, for cleaving single-stranded RNA substrates, single-stranded DNA substrates, and double-stranded DNA substrates at specific sites and for inserting a nucleic acid molecule into the cleaved substrate are provided. One method uses a nucleotide integrase to cleave one strand of a double-stranded DNA substrate. The method comprises the steps of: providing an isolated nucleotide integrase comprising a group II intron RNA having two hybridizing sequences for hybridizing with two intron RNA binding sequences on the top strand of the DNA substrate, and a group II-intron encoded protein which binds to a first sequence element of the substrate; and reacting the nucleotide integrase with the double-stranded DNA substrate to permit the nucleotide integrase to cleave the top strand of the DNA substrate and to insert the group II intron RNA into the cleavage site. The method of cleaving both strands of a double-stranded DNA substrate comprises the steps of: providing a nucleotide integrase comprising a group II intron RNA having two hybridizing sequences for hybridizing with two intron RNA binding sequences on one strand of the substrate, and a group II-intron encoded protein that interacts with a first sequence element and a second sequence element in the recognition site of the substrate; and reacting the nucleotide integrase with the double-stranded DNA substrate such that the nucleotide integrase cleaves both strands of the DNA substrate and inserts the group II intron RNA into the cleavage site of the one strand. The method for cleaving a single-stranded nucleic acid substrate comprises the steps of: providing a nucleotide integrase having two hybridizing sequences for hybridizing with two intron RNA-binding sequences on the single-stranded substrate, and a group II intron encoded protein; and reacting the nucleotide integrase with the single stranded nucleic acid substrate to allow the nucleotide integrase to cleave the substrate and to attach the group II intron RNA molecule thereto.

10 Claims, 24 Drawing Sheets

OTHER PUBLICATIONS

"A bacterial group II intron encoding reverse transcriptase, maturase, and DNA endonuclease activities: biochemical demonstration of maturase activity and insertion of new genetic information within the intron", by Matsuura, et al., *Genes& Development*, vol. 11, 1997, pp. 2910–2924.

"Group II intron endonucleases use both RNA and protein subuints for recognition of specific sequences in double–stranded DNA" by Guo, et al., *The EMBO Journal*, vol. 16, No. 22, 1997, pp. 6835–6848.

"Efficient integration of an intron RNA into double–stranded DNA by reverse splicing" by Yang, et al., *Nature*, vol. 381, No. 23, May 1996, pp. 332–335.

"Mobility of Yeast Mitochondrial Group II Introns: Engineering a New Site Specifically and Retrohoming via Full Reverse Splicing" by Eskes, et al., *Cell*, vol. 88, Mar. 21, 1997, pp. 865–874.

"Splicing of a Group II Intron Involved in the Conjugative Transfer of pRS01 in Lactococci" by Mills, et al., *Journal of Bacteriology*, vol. 178, No. 12, Jun. 1996, pp. 3531–3538.

"Splicing of a group II intron in a functional transfer gene of *Lactococcus lactis*" by Shearman, et al., *Molecular Microbiology*, vol. 21, 1996, pp. 45–53.

"Targeted DNA cleavage and insertion by group II introns" by Guo, et al., *RNA '97, The second annual meeting of RNA society*, May 27–Jun. 1, 1997, p. 262.

"A bacterial group II intorn encoding reverse transcriptase, maturase, and DNA endonuclease activities" by Matsuura, et al., *RNA '97, The second annual meeting of the RNA society*, May 27–Jun. 1, 1997, p. 369.

"Novel mechanisms for site–specific DNA cleavage and insertion involving group II intron catalytic RNA s" by Lambowitz, Functional Genomics Conference, Newport, Rhode Island, Nov. 2–5, 1997.

"Group II introns as site–specific retroelements", by Guo, et al., Keystone Symposia on Molecular and Cellular Biology: Transposition and Site–Specific Recombination, Santa Fe, New Mexico, Mar. 1–7, 1997.

"Group II intron mobility and evolution" by Zimmerly, et al., Keystone Symposia on Molecular and Cellular Biology: Posttranscriptional RNA Processing, Hilton Head, South Carolina, Mar. 11–17, 1996.

"Retrotransposition of group II introns" by Zimmerly, et al., Keystone Symposia on Molecular and Cellular Biology: Viral Genome Replication, Tamarron, Colorado, Mar. 1–7, 1996.

"Mitochondrial plasmid and group II intron reverse transcription" by Lambowitz, et al., Keystone Symposia on Molecular and Cellular Biology: Viral Genome Replication, Tamorron, Colorado, Mar. 1–7, 1996.

"Homing of a Group II Intron from *Lactococcus lactis* subsp. *lactis* ML3" Mills, et al., *Journal of Bacteriology* Oct. 1997, vol. 179, No. 19, pp. 6107–6111.

Executed Supplemental Information Disclosure Statement of Steven Zimmerly.

Executed Supplemental Information Disclosure Statement of Alan Lambowitz.

* cited by examiner

S. cerevisiae 161 mt coxI E1, aI1, E2, aI2, E3

```
<E1                                                               60
ATGGTACAAA GATGATTATA TTCAACAAAT GCAAAAGATA TTGCAGTATT ATATTTTATG

120
TTAGCTATTT TTAGTGGTAT GGCAGGAACA GCAATGTCTT TAATCATTAG ATTAGAATTA

E1>aI1     180
GCTGCACCTG GTTCACAATA TTTACATGGT AATTCACAGT TATTTAATGG TGCGCCTCTC

240
AGTGCGTATA TTTCGTTGAT GCGTCTAGCA TTAGTATTAT GAATCATCAA TAGATACTTA

300
AAACATATGA CTAACTCAGT AGGGGCTAAC TTTACGGGGA CAATAGCATG TCATAAAACA

360
CCTATGATTA GTGTAGGTGC AGTTAAGTGT TACATGGTTA GGTTAACGAA CTTCTTACAA

>EBS2<                                       420
GTCTTTATCA GGATTACAAT TTCCTCTTAT CATTTGGATA TAGTAAAACA AGTTTGATTA

>EBS1<                                                   480
TTTTACGTTG AGGTAATCAG ATTATGATTC ATTGTTTTAG ATAGCACAGG CAGTGTGAAA

540
AAGATGAAGG ACCTAAATAA CACAAAAGGA AATACGAAAA GTGAGGGATC AACTGAAAGA

600
GGAAACTCTT GAGTTGACAG AGGTATAGTA GTACCGAATA CTCAAATAAA AATGAGATTT

660
TTAAATCAAG TTAGATACTA TTCAGTAAAT AATAATTTAA AAATAGGGAA GGATACCAAT

720
ATTGAGTTAT CAAAAGATAC AAGTACTTCG GACTTGTTAG AATTTGAGAA ATTAGTAATA

′780
GATAATATAA ATGAGGAAAA TATAAATAAT AATTTATTAA GTATTATAAA AAACGTAGAT

840
ATATTAATAT TAGCATATAA TAGAATTAAG AGTAAACCTG GTAATATAAC TCCAGGTACA
```
————— MATCH TO FIG.2B —————

Fig. 2A

MATCH TO FIG. 2A

```
                                                                    900
ACATTAGAAA CATTAGATGG TATAAATATA ATATATTTAA ATAAATTATC AAATGAATTA

960
GGAACAGGTA AATTCAAATT TAAACCCATG AGAATAGTTA ATATTCCTAA ACCTAAAGCT

1020
GGTATAAGAC CTTTAAGTGT AGGTAATCCA AGAGATAAAA TTGTACAAGA AGTTATAAGA

1080
ATAATTTTAG ATACAATTTT TGATAAAAAG ATATCAACAC ATTCACATGG TTTTAGAAAG

1140
AATATAAGTT GTCAAACAGC AATTTGAGAA GTTAGAAATA TATTTGGTGG AAGTAATTGA

1200
TTTATTGAAG TAGACTTAAA AAAATGTTTT GATACAATTT CTCATGATTT AATTATTAAA

1260
GAATTAAAAA GATATATTTC AGATAAAGGT TTTATTGATT TAGTATATAA ATTATTAAGA

1320
GCTGGTTATA TTGATGAGAA AGGAACTTAT CATAAACCTA TATTAGGTTT ACCTCAAGGA

1380
TCATTAATTA GTCCTATCTT ATGTAATATT GTAATAACAT TGGTAGATAA TTGATTAGAA

1440
GATTATATTA ATTTATATAA TAAAGGTAAA GTTAAAAAAC AACATCCTAC ATATAAAAAA

1500
TTATCAAGAA TAATTGCAAA AGCTAAAATA TTTTCGACAA GATTAAAATT ACATAAAGAA

1560
AGAGCTAAAG GCCCACTATT TATTTATAAT GATCCTAATT TCAAGAGAAT AAAATACGTT

1620
AGATATGCAG ATGATATTTT AATTGGGGTA TTAGGTTCAA AAAATGATTG TAAAATAATC

1680
AAAAGAGATT TAAACAATTT TTTAAATTCA TTAGGTTTAA CTATAAATGA AGAAAAAACT
```

MATCH TO FIG. 2C

*Fig. 2B*

_MATCH TO FIG. 2B_

```
                                                                   1740
TTAATTACTT GTGCAACTGA ACTACCAGCA AGATTTTTAG GTTATAATAT TTCAATTACA

1800
CCTTTAAAAA GAATACCTAC AGTTACTAAA CTAATTAGAG GTAAACTTAT TAGAAGTAGA

1860
AATACAACTA GACCTATTAT TAATGCACCA ATTAGAGATA TTATCAATAA ATTAGCTACT

1920
AATGGATATT GTAAGCATAA TAAAAATGGT AGAATAGGAG TGCCTACAAG AGTAGGTAGA

1980
TGACTATATG AAGAACCTAG AACAATTATT AATAATTATA AAGCGTTAGG TAGAGGTATC

2040
TTAAATTATT ATAAATTAGC TACTAATTAT AAAAGATTAA GAGAAAGAAT CTATTACGTA

2100
TTATATTATT CATGTGTATT AACTTTAGCT AGTAAATATA GATTAAAAAC ATTAAGTAAA

2160
ACTATTAAAA AATTTGGTTA TAATTTAAAT ATTATTGAAA ATGATAAATT AATTGCCAAT

2220
TTTCCAAGAA ATACTTTTGA TAATATCAAA AAAATTGAAA ATCATGGTAT ATTTATATAT

2280
ATATCAGAAG CTAAAGTAAC TGATCCTTTT GAATATATCG ATTCAATTAA ATATATATTA

2340
CCTACAGCTA AAGCTAATTT TAATAAACCT TGTAGTATTT GTAATTCAAC TATTGATGTA

2400
GAAATACATC ATGTTAAACA ATTACATAGA GGTATATTAA AAGCACTTAA AGATTATATT

2460
CTAGGTAGAA TAATTACCAT AAACAGAAAA CAAATTCCAT TATGTAAACA ATGTCATATT

2520
AAAACACATA AAAATAAATT TAAAAATATA GCACCTGGTA TATAAAATCT ATTATTAATG
```

_MATCH TO FIG. 2D_

Fig. 2C

MATCH TO FIG.2C

```
                                                                    2580
ATACTCAATA TGGAAAGCCG TATGATGGGA AACTATCACG TACGGTTTGG GAAAGGCTCT aI1 > E2                        2640
TTAACACGTG GCAACATAGG TTAATTTGCT ATTACATTTT TAGTAGTTGG TCATGCTGTA

E2 > aI2                                                 2700
TTAATGATTT TCTGTGCGCC GTTTCGCTTA ATTTATCACT GTATTGAAGT GTTAATTGAT

2760
AAACATATCT CTGTTTATTC AATTAATGAA AACTTTACCG TATCATTTTG GTTCTGATTA

2820
TTAGTAGTAA CATACATAGT ATTTAGATAC GTAAACCATA TGGCTTACCC AGTTGGGGCC

2880
AACTCAACGG GGACAATAGC ATGCCATAAA AGCGCTGGAG TAAAACAGCC AGCGCAAGGT

> EBS2 <
AAGAACTGTC CGATGGCTAG GTTAACGAAT TCCTGTAAAG AATGTTTAGG GTTCTCATTA

> EBS1 <              3000
ACTCCTTCCC ACTTGGGGAT TGTGATTCAT GCTTATGTAT TGGAAGAAGA GGTACACGAG

3060
TTAACCAAAA ATGAATCATT AGCTTTAAGT AAAAGTTGAC ATTTGGAGGG CTGTACGAGT

3120
TCAAATGGAA AATTAAGAAA TACGGGATTG TCCGAAAGGG GAAACCCTGS GGATAACGGA

3180
GTCTTCATAG TACCCAAATT TAATTTAAAT AAAGCGAGAT ACTTTAGTAC TTTATCTAAA

3240
TTAAATGCAA GGAAGGAAGA CAGTTTAGCG TATTTAACAA AGATTAATAC TACGGATTTT

3300
TCCGAGTTAA ATAAATTAAT AGAAAATAAT CATAATAAAC TTGAAACCAT TAATACTAGA

3360
ATTTTAAAAT TAATGTCAGA TATTAGAATG TTATTAATTG CTTATAATAA AATTAAAAGT
```

MATCH TO FIG.2E

*Fig. 2D*

_MATCH TO FIG.2D_

```
                                                                      3420
AAGAAAGGTA ATATATCTAA AGGTTCTAAT AATATTACCT TAGATGGGAT TAATATTTCA

3480
TATTTAAATA AATTATCTAA AGATATTAAC ACTAATAYGT TTAAATTTTC TCCGGTTAGA

3540
AGAGTTGAAA TTCCTAAAAC ATCTGGAGGA TTTAGACCTT TAAGTGTTGG AAATCCTAGA

3600
GAAAAAATTG TACAAGAAAG TATGAGAATA ATATTAGAAA TTATCTATAA TAATAGTTTC

3660
TCTTATTATT CTCATGGATT TAGACCTAAC TTATCTTGTT TAACAGCTAT TATTCAATGT

3720
AAAAATTATA TGCAATACTG TAATTGATTT ATTAAAGTAG ATTTAAATAA ATGCTTTGAT

3780
ACAATTCCAC ATAATATGTT AATTAATGTA TTAAATGAGA GAATCAAAGA TAAAGGTTTC

3840
ATAGACTTAT TATATAAATT ATTAAGAGCT GGATATGTTG ATAAAAATAA TAATTATCAT

3900
AATACAACTT TAGGAATTCC TCAAGGTAGT GTTGTCAGTC CTATTTTATG TAATATTTTT

3960
TTAGATAAAT TAGATAAATA TTTAGAAAAT AAATTTGAGA ATGAATTCAA TACTGGAAAT

4020
ATGTCTAATA GAGGTAGAAA TCCAATTTAT AATAGTTTAT CATCTAAAAT TTATAGATGT

4080
AAATTATTAT CTGAAAAATT AAAATTGATT AGATTAAGAG ACCATTACCA AAGAAATATG

4140
GGATCTGATA AAAGTTTTAA AAGAGCTTAT TTTGTTAGAT ATGCTGATGA TATTATCATT

4200
GGTGTAATGG GTTCTCATAA TGATTGTAAA AATATTTTAA ACGATATTAA TAACTTCTTA
```

_MATCH TO FIG.2F_

Fig. 2E

MATCH TO FIG.2E

```
                                                                 4260
AAAGAAAATT TAGGTATGTC AATTAATATA GATAAATCCG TTATTAAACA TTCTAAAGAA

4320
GGAGTTAGTT TTTTAGGGTA TGATGTAAAA GTTACACCTT GAGAAAAAAG ACCTTATAGA

4380
ATGATTAAAA AAGGTGATAA TTTTATTAGG GTTAGACATC ATACTAGTTT AGTTGTTAAT

4440
GCCCCTATTA GAAGTATTGT AATAAAATTA AATAAACATG GCTATTGTTC TCATGGTATT

4500
TTAGGAAAAC CCAGAGGGGT TGGAAGATTA ATTCATGAAG AAATGAAAAC CATTTTAATG

4560
CATTACTTAG CTGTTGGTAG AGGTATTATA AACTATTATA GATTAGCTAC CAATTTTACC

4620
ACATTAAGAG GTAGAATTAC ATACATTTTA TTTTATTCAT GTTGTTTAAC ATTAGCAAGA

4680
AAATTTAAAT TAAATACTGT TAAGAAAGTT ATTTTAAAAT TCGGTAAAGT ATTAGTTGAT

4740
CCTCATTCAA AAGTTAGTTT TAGTATTGAT GATTTTAAAA TTAGACATAA AATAAATATA

4800
ACTGATTCTA ATTATACACC TGATGAAATT TTAGATAGAT ATAAATATAT GTTACCTAGA

4860
TCTTTATCAT TATTTAGTGG TATTTGTCAA ATTTGTGGTT CTAAACATGA TTTAGAAGTA

4920
CATCACGTAA GAACATTAAA TAATGCTGCC AATAAAATTA AAGATGATTA TTTATTAGGT

4980
AGAATGATTA AGATAAATAG AAAACAAATT ACTATCTGTA AAACATGTCA TTTTAAAGTT

5040
CATCAAGGTA AATATAATGG TCCAGGTTTA TAATAATTAT TATACTCCTT CGGGGTCGCC
```

MATCH TO FIG.2G

Fig. 2F

MATCH TO FIG.2F

5100
GCGGGGGCGG GCCGGACTAT TAAATATGCG TTAAATGGAG AGCCGTATGA TATGAAAGTA

5160
TCACGTACGG TTCGGAGAGG GCTCTTTTAT ATGAATGTTA TTACATTCAG ATAGGTTTGC aI2 > E3　　　　　　　　　　　　　　　　　　　　E3
TACTCTACTC TTAGTAATGC CTGCTTTAAT TGGAGGTTTT GGT

```
       10         20         30         40         50         60
AAGCTTAGAGAAAAATAATGCGGTGCTTGGTCATCACCTCATCCAATCATTTTCTCCTGA
TTCGAATCTCTTTTTATTACGCCACGAACCAGTAGTGGAGTAGGTTAGTAAAAGAGGACT 70         80         90        100        110        120
TGACAATCTAACTCCTGAACAAATTCATGAAATAGGTCGTCAAACCATATTAGAATTTAC   LtrB.E1
ACTGTTAGATTGAGGACTTGTTTAAGTACTTTATCCAGCAGTTTGGTATAATCTTAAATG 130        140        150        160        170        180
AGGTGGCGAATATGAATTTGTGATTGCAACCCACGTCGATCGTGAACACATCCATAACGT   LtrBl
TCCACCGCTTATACTTAAACACTAACGTTGGGTGCAGCTAGCACTTGTGTAGGTATTGCA 190        200        210        220        230        240
GCGCCCAGATAGGGTGTTAAGTCAAGTAGTTTAAGGTACTACTCTGTAAGATAACACAGA
CGCGGGTCTATCCCACAATTCAGTTCATCAAATTCCATGATGAGACATTCTATTGTGTCT 250        260        270        280        290        300
AAACAGCCAACCTAACCGAAAAGCGAAAGCTGATACGGGAACAGAGCACGGTTGGAAAGC
TTTGTCGGTTGGATTGGCTTTTCGCTTTCGACTATGCCCTTGTCTCGTGCCAACCTTTCG 310        320        330        340        350        360
GATGAGTTACCTAAAGACAATCGGGTACGACTGAGTCGCAATGTTAATCAGATATAAGGT
CTACTCAATGGATTTCTGTTAGCCCATGCTGACTCAGCGTTACAATTAGTCTATATTCCA 370        380        390       400 EBS2  410        420
ATAAGTTGTGTTTACTGAACGCAAGTTTCTAATTTCGGTTATGTGTCGATAGAGGAAAGT
TATTCAACACAAATGACTTGCGTTCAAAGATTAAAGCCAATACACAGCTATCTCCTTTCA
                                             EBS1
      430        440        450        460  \    470        480
GTCTGAAACCTCTAGTACAAAGAAAGGTAAGTTATGGTTGTGGACTTATCTGTTATCACC
CAGACTTTGGAGATCATGTTTCTTTCCATTCAATACCAACACCTGAATAGACAATAGTGG 490        500        510        520        530        540
ACATTTGTACAATCTGTAGGAGAACCTATGGGAACGAAACGAAAGCGATGCCGAGAATCT
TGTAAACATGTTAGACATCCTCTTGGATACCCTTGCTTTGCTTTCGCTACGGCTCTTAGA 550        560        570        580        590        600
GAATTTACCAAGACTTAACACTAACTGGGGATACCCTAAACAAGAATGCCTAATAGAAAG
CTTAAATGGTTCTGAATTGTGATTGACCCCTATGGGATTTGTTCTTACGGATTATCTTTC
-------------------------------------
          MATCH TO FIG.10B
```

Fig. 10A

MATCH TO FIG. 10A

```
       610       620       630       640       650       660
GAGGAAAAAGGCTATAGCACTAGAGCTTGAAAATCTTGCAAGGGTACGGAGTACTCGTAG
CTCCTTTTTCCGATATCGTGATCTCGAACTTTTAGAACGTTCCCATGCCTCATGAGCATC 670       680       690       700       710       720
TAGTCTGAGAAGGGTAACGCCCTTTACATGGCAAAGGGGTACAGTTATTGTGTACTAAAA
ATCAGACTCTTCCCATTGCGGGAAATGTACCGTTTCCCCATGTCAATAACACATGATTTT

→LtrA ORF
       730       740       750       760       770       780
TTAAAAATTGATTAGGGAGGAAAACCTCAAAATGAAACCAACAATGGCAATTTTAGAAAG
AATTTTTAACTAATCCCTCCTTTTGGAGTTTTACTTTGGTTGTTACCGTTAAAATCTTTC 790       800       810       820       830       840
AATCAGTAAAAATTCACAAGAAAATATAGACGAAGTTTTTACAAGACTTTATCGTTATCT
TTAGTCATTTTTAAGTGTTCTTTTATATCTGCTTCAAAAATGTTCTGAAATAGCAATAGA 850       860       870       880       890       900
TTTACGTCCAGATATTTATTACGTGGCGTATCAAAATTTATATTCCAATAAAGGAGCTTC
AAATGCAGGTCTATAAATAATGCACCGCATAGTTTTAAATATAAGGTTATTTCCTCGAAG 910       920       930       940       950       960
CACAAAAGGAATATTAGATGATACAGCGGATGGCTTTAGTGAAGAAAAAATAAAAAAGAT
GTGTTTTCCTTATAATCTACTATGTCGCCTACCGAAATCACTTCTTTTTATTTTTTCTA 970       980       990      1000      1010      1020
TATTCAATCTTTAAAAGACGGAACTTACTATCCTCAACCTGTACGAAGAATGTATATTGC
ATAAGTTAGAAATTTTCTGCCTTGAATGATAGGAGTTGGACATGCTTCTTACATATAACG 1030      1040      1050      1060      1070      1080
AAAAAAGAATTCTAAAAAGATGAGACCTTTAGGAATTCCAACTTTCACAGATAAATTGAT
TTTTTTCTTAAGATTTTTCTACTCTGGAAATCCTTAAGGTTGAAAGTGTCTATTTAACTA 1090      1100      1110      1120      1130      1140
CCAAGAAGCTGTGAGAATAATTCTTGAATCTATCTATGAACCGGTATTCGAAGATGTGTC
GGTTCTTCGACACTCTTATTAAGAACTTAGATAGATACTTGGCCATAAGCTTCTACACAG 1150      1160      1170      1180      1190      1200
TCACGGTTTTAGACCTCAACGAAGCTGTCACACAGCTTTGAAAACAATCAAAAGAGAGTT
AGTGCCAAAATCTGGAGTGGCTTCGACAGTGTGTCGAAACTTTTGTTAGTTTTCTCTCAA
```

MATCH TO FIG. 10C

*Fig. 10B*

MATCH TO FIG. 10B

```
      1210      1220      1230      1240      1250      1260
TGGCGGCGCAAGATGGTTTGTGGAGGGAGATATAAAAGGCTGCTTCGATAATATAGACCA
ACCGCCGCGTTCTACCAAACACCTCCCTCTATATTTTCCGACGAAGCTATTATATCTGGT 1270      1280      1290      1300      1310      1320
CGTTACACTCATTGGACTCATCAATCTTAAAATCAAAGATATGAAAATGAGCCAATTGAT
GCAATGTGAGTAACCTGAGTAGTTAGAATTTTAGTTTCTATACTTTTACTCGGTTAACTA 1330      1340      1350      1360      1370      1380
TTATAAATTTCTAAAAGCAGGTTATCTGGAAAACTGGCAGTATCACAAAACTTACAGCGG
AATATTTAAAGATTTTCGTCCAATAGACCTTTTGACCGTCATAGTGTTTTGAATGTCGCC 1390      1400      1410      1420      1430      1440
AACACCTCAAGGTGGAATTCTATCTCCTCTTTTGGCCAACATCTATCTTCATGAATTGGA
TTGTGGAGTTCCACCTTAAGATAGAGGAGAAAACCGGTTGTAGATAGAAGTACTTAACCT 1450      1460      1470      1480      1490      1500
TAAGTTTGTTTTACAACTCAAAATGAAGTTTGACCGAGAAAGTCCAGAAAGAATAACACC
ATTCAAACAAAATGTTGAGTTTTACTTCAAACTGGCTCTTTCAGGTCTTTCTTATTGTGG 1510      1520      1530      1540      1550      1560
TGAATATCGGGAACTTCACAATGAGATAAAAAGAATTTCTCACCGTCTCAAGAAGTTGGA
ACTTATAGCCCTTGAAGTGTTACTCTATTTTTCTTAAAGAGTGGCAGAGTTCTTCAACCT 1570      1580      1590      1600      1610      1620
GGGTGAAGAAAAAGCTAAAGTTCTTTTAGAATATCAAGAAAAACGTAAAAGATTACCCAC
CCCACTTCTTTTTCGATTTCAAGAAAATCTTATAGTTCTTTTTGCATTTTCTAATGGGTG 1630      1640      1650      1660      1670      1680
ACTCCCCTGTACCTCACAGACAAATAAAGTATTGAAATACGTCCGGTATGCGGACGACTT
TGAGGGGACATGGAGTGTCTGTTTATTTCATAACTTTATGCAGGCCATACGCCTGCTGAA 1690      1700      1710      1720      1730      1740
CATTATCTCTGTTAAAGGAAGCAAAGAGGACTGTCAATGGATAAAAGAACAATTAAAACT
GTAATAGAGACAATTTCCTTCGTTTCTCCTGACAGTTACCTATTTTCTTGTTAATTTTGA 1750      1760      1770      1780      1790      1800
TTTTATTCATAACAAGCTAAAAATGGAATTGAGTGAAGAAAAAACACTCATCACACATAG
AAAATAAGTATTGTTCGATTTTTACCTTAACTCACTTCTTTTTTGTGAGTAGTGTGTATC
```

MATCH TO FIG. 10D

*Fig. 10C*

MATCH TO FIG. 10C

```
         1810      1820      1830      1840      1850      1860
     CAGTCAACCCGCTCGTTTTCTGGGATATGATATACGAGTAAGGAGAAGTGGAACGATAAA
     GTCAGTTGGGCGAGCAAAAGACCCTATACTATATGCTCATTCCTCTTCACCTTGCTATTT 1870      1880      1890      1900      1910      1920
     ACGATCTGGTAAAGTCAAAAAGAGAACACTCAATGGGAGTGTAGAACTCCTTATTCCTCT
     TGCTAGACCATTTCAGTTTTTCTCTTGTGAGTTACCCTCACATCTTGAGGAATAAGGAGA 1930      1940      1950      1960      1970      1980
     TCAAGACAAAATTCGTCAATTTATTTTTGACAAGAAAATAGCTATCCAAAAGAAAGATAG
     AGTTCTGTTTTAAGCAGTTAAATAAAAACTGTTCTTTTATCGATAGGTTTTCTTTCTATC 1990      2000      2010      2020      2030      2040
     CTCATGGTTTCCAGTTCACAGGAAATATCTTATTCGTTCAACAGACTTAGAAATCATCAC
     GAGTACCAAAGGTCAAGTGTCCTTTATAGAATAAGCAAGTTGTCTGAATCTTTAGTAGTG 2050      2060      2070      2080      2090      2100
     AATTTATAATTCTGAATTAAGAGGGATTTGTAATTACTACGGTCTAGCAAGTAATTTTAA
     TTAAATATTAAGACTTAATTCTCCCTAAACATTAATGATGCCAGATCGTTCATTAAAATT 2110      2120      2130      2140      2150      2160
     CCAGCTCAATTATTTTGCTTATCTTATGGAATACAGCTGTCTAAAAACGATAGCCTCCAA
     GGTCGAGTTAATAAAACGAATAGAATACCTTATGTCGACAGATTTTTGCTATCGGAGGTT 2170      2180      2190      2200      2210      2220
     ACATAAGGGAACACTTTCAAAAACCATTTCCATGTTTAAAGATGGAAGTGGTTCGTGGGG
     TGTATTCCCTTGTGAAAGTTTTTGGTAAAGGTACAAATTTCTACCTTCACCAAGCACCCC 2230      2240      2250      2260      2270      2280
     CATCCCGTATGAGATAAAGCAAGGTAAGCAGCGCCGTTATTTTGCAAATTTTAGTGAATG
     GTAGGGCATACTCTATTTCGTTCCATTCGTCGCGGCAATAAAACGTTTAAAATCACTTAC 2290      2300      2310      2320      2330      2340
     TAAATCCCCTTATCAATTTACGGATGAGATAAGTCAAGCTCCTGTATTGTATGGCTATGC
     ATTTAGGGGAATAGTTAAATGCCTACTCTATTCAGTTCGAGGACATAACATACCGATACG 2350      2360      2370      2380      2390      2400
     CCGGAATACTCTTGAAAACAGGTTAAAAGCTAAATGTTGTGAATTATGTGGAACATCTGA
     GGCCTTATGAGAACTTTTGTCCAATTTTCGATTTACAACACTTAATACACCTTGTAGACT
```

MATCH TO FIG. 10E

*Fig. 10D*

MATCH TO FIG.10D

```
        2410      2420      2430      2440      2450      2460
TGAAAATACTTCCTATGAAATTCACCATGTCAATAAGGTCAAAAATCTTAAAGGCAAAGA
ACTTTTATGAAGGATACTTTAAGTGGTACAGTTATTCCAGTTTTTAGAATTTCCGTTTCT 2470      2480      2490      2500      2510      2520
AAAATGGGAAATGGCAATGATAGCGAAACAACGTAAAACTCTTGTTGTATGCTTTCATTG
TTTTACCCTTTACCGTTACTATCGCTTTGTTGCATTTTGAGAACAACATACGAAAGTAAC
                                    ┌─→LtrA ORF
        2530      2540      2550    │  2560      2570      2580
TCATCGTCACGTGATTCATAAACACAAGTGAATTTTTACQAACGAACAATAACAGAGCCG
AGTAGCAGTGCACTAAGTATTTGTGTTCACTTAAAAATGCTTGCTTGTTATTGTCTCGGC 2590      2600      2610      2620      2630      2640
TATACTCCGAGAGGGGTACGTACGGTTCCCGAAGAGGGTGGTGCAAACCAGTCACAGTAA     LtrBI
ATATGAGGCTCTCCCCATGCATGCCAAGGGCTTCTCCCACCACGTTTGGTCAGTGTCATT 2650      2660      2670│ 2680      2690      2700
                                │                                 LtrB.E2
TGTGAACAAGGCGGTACCTCCCTACTTCACCATATCATTTTTAATTCTACGAATCTTTAT
ACACTTGTTCCGCCATGGAGGGATGAAGTGGTATAGTAAAAATTAAGATGCTTAGAAATA 2710      2720      2730      2740      2750      2760
ACTGGCAAACAATTTGACTGGAAAGTCATTCCTAAAGAGAAAACAAAAAGCGGCAAAGCT
TGACCGTTTGTTAAACTGACCTTTCAGTAAGGATTTCTCTTTTGTTTTTCGCCGTTTCGA
```

```
          10        20        30        40        50        60
MKPTMAILERISKNSQENIDEVFTRLYRYLLRPDIYYVAYQNLYSNKGASTKGILDDTAD 70        80        90       100       110       120
GFSEEKIKKIIQSLKDGTYYPQPVRRMYIAKKNSKKMRPLGIPTFTDKLIQEAVRIILES 130       140       150       160       170       180
IYBPVFEDVSHGFRPQRSCHTALKTIKREFGGARWFVEGDIKGCFDNIDHVTLIGLINLK 190       200       210       220       230       240
IKDMKMSQLIYKFLKAGYLENWQYHKTYSGTPQGGILSPLLANIYLHELDKFVLQLKMKF 250       260       270       280       290       300
DRESPERITPEYRELHNEIKRISHRLKKLEGEEKAKVLLEYQEKRKRLPTLPCTSQTNKV 310       320       330       340       350       360
LKYVRYADDFIISVKGSKEDCQWIKEQLKLFIHNKLKMELSEEKTLITHSSQPARFLGYD 370       380       390       400       410       420
IRVRRSGTIKRSGKVKKRTLNGSVELLIPLQDKIRQFIFDKKIAIQKKDSSWFPVHRKYL 430       440       450       460       470       480
IRSTDLEIITIYNSELRGICNYYGLASNFNQLNYFAYLMEYSCLKTIASKHKGTLSKTIS 490       500       510       520       530       540
MFKDGSGSWGIPYEIKQGKQRRYFANFSECKSPYQFTDEISQAPVLYGYARNTLENRLKA 550       560       570       580       590       600
KCCELCGTSDENTSYEIHHVNKVKNLKGKEKWEMAMIAKQRKTLVVCFHCHRHVIHKHK*
```

FIGURE 11

File: targets.ltra                                        September 26, 1997

Lactococcus target DNA: mutant oligos for top strand: MUTATIONS ARE UNDERLINED

```
        Pvu I     E1              ↓              E2              EcoR I
         |         |                                              |
        CCCACGTCGATCGTGAACACATCCATAACCATATCATTTTTAATTCTACGAATCTTTATACGGgaattccg   72
        GGGTGCAGCTAGCACTTGTGTAGGTATTGGTATAGTAAAAATTAAGATGCTTAGAAATATACCcttaaggc
                                    ↑
```

```
WT          CCCACGTCGATCGTGAACACATCCATA
C-24H       CCCACHTCGATCGTGAACACATCCATA
T-23V       CCCACGVCGATCGTGAACACATCCATA
C-22D       CCCACGTDGATCGTGAACACATCCATA
G-21H       CCCACGTCHATCGTGAACACATCCATA
A-20B       CCCACGTCGBTCGTGAACACATCCATA
T-19V       CCCACGTCGAVCGTGAACACATCCATA
C-18D       CCCACGTCGATDGTGAACACATCCATA
G-17H       CCCACGTCGATCHTGAACACATCCATA
T-16V       CCCACGTCGATCGVGAACACATCCATA
G-15H       CCCACGTCGATCGTHAACACATCCATA
A-14B       CCCACGTCGATCGTGBACACATCCATA
A-13B       CCCACGTCGATCGTGABCACATCCATA
LLN         CCCACGTDHBVDHVHBBCACATCCATA
LLN-2       CCCACGTDGAVDHVHBBCACATCCATA
LLN-3A      CCCACGTDGATDHVHBBCACATCCATA
LLN-4       CCCACGTDGATDGVHBBCACATCCATA
LLN-3B      CCCACGTDHBVDGTGBBCACATCCATA
GC1         CCCGCGGCGATCGTGAACACATCCATA
GC2         CCCACGTCGATCGGGGACACATCCATA

WT2         CCCACGTCGATCGTGAACACATCCATAACCATATCATTTT
A-13Y       CCCACGTCGATCGTGAYCACATCCATAACCATATCATTTT
C-12R       CCCACGTCGATCGTGAARACATCCATAACCATATCATTTT
A-11Y       CCCACGTCGATCGTGAACYCATCCATAACCATATCATTTT
C-10R       CCCACGTCGATCGTGAACARATCCATAACCATATCATTTT
A-9Y        CCCACGTCGATCGTGAACACYTCCATAACCATATCATTTT
T-8R        CCCACGTCGATCGTGAACACARCCATAACCATATCATTTT
C-7R        CCCACGTCGATCGTGAACACATRCATAACCATATCATTTT
C-6R        CCCACGTCGATCGTGAACACATCRATAACCATATCATTTT
A-5Y        CCCACGTCGATCGTGAACACATCCYTAACCATATCATTTT
T-4R        CCCACGTCGATCGTGAACACATCCARAACCATATCATTTT
A-3Y        CCCACGTCGATCGTGAACACATCAATYACCATATCATTTT
A-2Y        CCCACGTCGATCGTGAACACATCCATAYCCATATCATTTT
C-1R        CCCACGTCGATCGTGAACACATCCATAARCATATCATTTT
C+1R        CCCACGTCGATCGTGAACACATCCATAACRATATCATTTT
cIBS1IBS2   CCCACGTCGATCGTGAAGTGTAGGTATTGCATATCATTTT
c9875321    CCCACGTCGATCGTGAACACTAGCTTTTGCATATCATTTT
```

FIG. 12A

Lactococcus target DNA: mutant oligos for top strand: MUTATIONS ARE UNDERLINED

```
                    Pvu I                                          EcoR I
                    |                                              |
          CCCACGTCGATCGTGAACACATCCATAACCATATCATTTTAATTCTACGAATCTTTATACTGGgaattccg  72
          GGGTGCAGCTAGCACTTGTGTAGGTATTGGTATAGTAAAATTAAGATGCTTAGAAATATGACCcttaaggc L753      CCCACGTCGATCGTGAACACATGCTTTACCATATCATTTT
C-7T      CCCACGTCGATCGTGAACACATTCATAACCATATCATTTT
C-7A      CCCACGTCGATCGTGAACACATACATAACCATATCATTTT
C-7G      CCCACGTCGATCGTGAACACATGCATAACCATATCATTTT
A-5T      CCCACGTCGATCGTGAACACATCCTTAACCATATCATTTT
A-5C      CCCACGTCGATCGTGAACACATCCCTAACCATATCATTTT
A-5G      CCCACGTCGATCGTGAACACATCCGTAACCATATCATTTT
A-3T      CCCACGTCGATCGTGAACACATCCATTACCATATCATTTT
A-3C      CCCACGTCGATCGTGAACACATCCATCACCATATCATTTT
A-3G      CCCACGTCGATCGTGAACACATCCATGACCATATCATTTT
C-12G     CCCACGTCGATCGTGAAGACATCCATAACCATATCATTTT
T-11A     CCCACGTCGATCGTGAACTCATCCATAACCATATCATTTT
C-10G     CCCACGTCGATCGTGAACAGATCCATAACCATATCATTTT
T-4G      CCCACGTCGATCGTGAACACATCCAGAACCATATCATTTT
C-1G      CCCACGTCGATCGTGAACACATCCATAACGATATCATTTTAA
A+2T      CCCACGTCGATCGTGAACACATCCATAACCTTATCATTTTAA
T+3A      CCCACGTCGATCGTGAACACATCCATAACCAAATCATTTTAA
T+3G      CCCACGTCGATCGTGAACACATCCATAACCAGATCATTTTAA
A+4T      CCCACGTCGATCGTGAACACATCCATAACCATTTCATTTTAA
T+5G      CCCACGTCGATCGTGAACACATCCATAACCATAGCATTTTAA
TopI      CCCACGTCGATCGTGAACACATCCATAACCTGCGCATTTTAA
```

Lactococcus target DNA: mutant oligos for bottom strand

```
                    Pvu I                                          EcoR I
                    |                                              |
          CCCACGTCGATCGTGAACACATCCATAACCATATCATTTTAATTCTACGAATCTTTATACTGGgaattccg  72
          GGGTGCAGCTAGCACTTGTGTAGGTATTGGTATAGTAAAATTAAGATGCTTAGAAATATGACCcttaaggc
```

MUTATIONS ARE UNDERLINED

```
LLBOT        GTGTAGGTATTGGTATAGTAAAATTAAGATGCTTAGAAATATGACCcttaaggc
LLBOT2                      TATAGTAAAATTAAGATGCTTACAAATATGACCcttaaggc
LLBOT 3                         AGTAAAATTAAGATGCTTAGAAATATGACCcttaaggc
BotT         GTGTAGGTATTGGACGCGTAAAATTAAGATGCTTAGAAATATGACCcttaagga
LL3'compI    GTGTAGGTATTGGATATCATTTTAATTCTAGGAAAGAAAAAGACCCTTAGGC
```

KEY TO MUTATIONS

METHODS FOR CLEAVING SINGLE-STRANDED AND DOUBLE-STRANDED DNA SUBSTRATES WITH NUCLEOTIDE INTEGRASE

This application claims the benefit of U.S. Provisional Application No. 60/076,161, filed Feb. 26, 1998.

The present invention was made with support from National Institute of Health Grant NO. GM37949. The United States Government has certain rights in the invention.

BACKGROUND

In recent years, a number of methods have been developed for manipulating DNA. Some of these methods employ biomolecules to cut or cleave DNA, which in some instances renders the substrate DNA nonfunctional. Other methods employ biomolecules to facilitate insertion of new pieces of nucleic acid into the cleavage site of the DNA substrate. The insertion of new segments of nucleic acid into the cleavage sites of the DNA substrate changes the characteristics of the RNA or protein molecules encoded by the substrate DNA molecules. Accordingly, the biomolecules which catalyze the cleavage of DNA substrates or the insertion of new nucleic acid molecules into the DNA substrates are useful tools for genetic engineering, for analytical studies and for diagnostic studies. One such molecule used for cleaving DNA substrates is the restriction endonuclease.

Restriction endonucleases are enzymatic proteins that cleave double-stranded DNA. Such endonucleases recognize specific nucleotide sequences in double-stranded DNA, and cleave both strands within or near the specific recognition site. Such specificity renders the restriction endonucleases important tools in the controlled fragmentation of double-stranded DNA. Restriction endonucleases are also useful analytical tools for determining whether certain sequences are present in substrate DNA and in genomic sequencing studies.

However, restriction endonucleases only cleave DNA substrates; they do not insert new nucleic acid molecules into the cleaved DNA substrate. Accordingly, another biomolecule is needed to insert new pieces of DNA or RNA into the double-stranded DNA.

Ribozymes are catalytic RNA molecules that cleave RNA and, in certain circumstances, that insert new pieces of RNA into the cleavage site of the RNA substrate. Unfortunately, ribozymes have not been particularly useful for cleaving single-stranded DNA substrates or double-stranded DNA substrates. Ribozymes cut single-stranded DNA only under extreme conditions of elevated temperatures and high concentrations of magnesium. Ribozymes can be used to cleave double-stranded DNA only after the DNA is denatured and separated into two pieces of single-stranded DNA. Moreover, ribozymes have limited use in systems containing ribonucleases.

Accordingly, it would be desirable to have methods which employ a new tool that is capable of cleaving double-stranded DNA molecules, single-stranded DNA molecules, and single-stranded RNA molecules at specific sites. Methods which employ a new biomolecule capable of cleaving RNA molecules, single-stranded DNA molecules and double-stranded DNA molecules at specific sites and simultaneously inserting a new nucleic acid molecule into the cleavage site are especially desirable.

SUMMARY OF THE INVENTION

The present invention provides new methods, employing a nucleotide integrase, for cleaving single-stranded RNA substrates, single-stranded DNA substrates, and double-stranded DNA substrates at specific sites and for inserting nucleic acid molecules into the cleaved substrate. The nucleotide integrase is a ribonucloeprotein particle comprising a group II intron RNA and a group II intron-encoded protein, which is bound to the group II intron RNA.

One method uses a nucleotide integrase to cleave one strand, hereinafter referred to as the "top strand" of a double-stranded DNA substrate. The method comprises the steps of: providing a nucleotide integrase comprising a group II intron RNA having two hybridizing sequences, "EBS1" and "EBS2", that are capable of hybridizing with two intron RNA binding sequences,"IBS1" and "IBS2", respectively, on the top strand of the DNA substrate, and a group II intron-encoded protein which binds to a first sequence element of the substrate; and reacting the nucleotide integrase with the double-stranded DNA substrate under conditions that permit the nucleotide integrase to cleave the top strand of the DNA substrate and to insert the group II intron RNA into the cleavage site. Preferably, the nucleotide immediately preceding the first nucleotide of the EBS1 sequence on the group II intron RNA, hereinafter referred to as the δ nucleotide is complementary to the nucleotide at +1 on the top strand of the substrate, hereinafter referred to as the δ' nucleotide.

As denoted herein, nucleotides that are located upstream of the cleavage site have a (−) position relative to the cleavage site, and nucleotides that are located downstream of the cleavage site have a (+) position relative to the cleavage site. Thus, in the above-described method, the cleavage site is located between nucleotides −1 and +1 on the top strand of the double-stranded DNA substrate. The IBS1 sequence and the IBS2 sequence lie in a region of the recognition site which extends from about position −1 to about position −14 relative to the cleavage site. As denoted herein, the first sequence element comprises from about 10 to about 12 pairs of nucleotides that lie upstream of IBS2 and IBS1, i.e from about position −12 relative to the cleavage site to about position −26 relative to the cleavage site. As denoted herein, the second sequence element comprises from about 10 to about 12 pairs of nucleotides that lie downstream of the cleavage site, i.e., at positions +1 to about +12. The EBS1 sequence of the group II intron RNA comprises from about 5 to 7 nucleotides and has substantial complementarity with the nucleotides at positions −1 to about −5 or about −7 on the top strand of the DNA substrate. The EBS2 sequence comprises from about 4 to 7 nucleotides and has substantial complementarity with the nucleotides at positions from about −6 to about −14 on the top strand of the DNA substrate.

The present invention also provides a method which employs a nucleotide integrase to cleave both strands of a double-stranded DNA substrate. The method comprises the steps of: providing a nucleotide integrase comprising a group II intron RNA having two hybridizing sequences, EBS1 and EBS2, that are capable of hybridizing with two intron RNA binding sequences, IBS1 and IBS2, on the top strand of the substrate, and a group II-intron encoded protein that is capable of binding to a first sequence element and to a second sequence element in the recognition site of the substrate; and reacting the nucleotide integrase with the double-stranded DNA substrate such that the nucleotide integrase cleaves both strands of the DNA substrate and inserts the group II intron RNA into the cleavage site of the top strand. As denoted herein, the second sequence element comprises from about 10 to about 12 pairs of nucleotides that lie downstream of the cleavage site, i.e from position +1 to about position +10, +11, or +12. Preferably, the δ nucleotide of the group II intron RNA is complementary to the δ' nucleotide on the top strand of the substrate.

Another method provided by the present invention employs a nucleotide integrase for cleaving a single stranded nucleic acid substrate and for inserting the group II intron RNA of the nucleotide integrase into the cleavage site. The method comprises the steps of: providing a nucleotide integrase having two hybridizing sequences, EBS1 and EBS2, that are capable of hybridizing with two intron RNA-binding sequences, IBS1 and IBS2, on the single-stranded substrate, and a group II intron encoded protein; and reacting the nucleotide integrase with the single stranded nucleic acid substrate for a time and at a temperature sufficient to allow the nucleotide integrase to cleave the substrate and to attach the group II intron RNA molecule thereto. The EBS1 sequence of the group II intron RNA comprises from about 5 to 7 nucleotides that have substantial complementarity with the nucleotides at positions −1 to about −5 or about −7 relative to the putative cleavage site. The EBS2 sequence comprises from about 4 to 7 nucleotides that have substantial complementarity with the nucleotides at positions from about −6 to about −13 relative to the putative cleavage site. Preferably, the δ nucleotide of the group II intron RNA is complementary to the δ' nucleotide on the top strand of the substrate.

The present invention also relates to a method of determining whether a nucleic acid comprises a particular recognition site. The method comprises the steps of providing a nucleotide integrase capable of cleaving a nucleic acid comprising a particular recognition site; reacting the nucleotide integrase with the nucleic acid; and assaying for cleavage of the nucleic acid, wherein cleavage of the nucleic acid indicates that the nucleic acid comprises the recognition site.

BRIEF DESCRIPTION OF THE DRAWINGS

FIGS. 2A–2G is a diagram depicting the nucleotide sequence and the secondary structure of the aI2 intron RNA and the excised group II intron RNA of the first intron of the *S. cerevisiae* mitochondrial COX1 gene, hereinafter referred to as the "aI1 intron" RNA.

FIG. 4 is a graph showing the relative extent of cleavage of the substrates having mutations in the nucleotides upstream of the cleavage site by a nucleotide integrase comprising a wild-type aI2 intron RNA and the protein encoded thereby.

FIGS. 10A–10E shows the nucleotide sequence SEQ ID NO: 5 of the Ll.ltrB intron RNA plus portions of the exon sequences that flank the Ll.ltrB intron RNA.

FIG. 11 is the amino acid sequence SEQ ID NO: 6 of the ltrA protein.

FIG. 12 is a chart depicting the sequences of DNA substrates cleaved by nucleotide integrases comprising a wild-type or modified Ll.ltrB intron RNA and the ltrA protein.

DETAILED DESCRIPTION OF THE INVENTION

The present invention provides new methods that employ a nucleotide integrase for manipulating DNA and RNA substrates. One method uses a nucleotide integrase to cleave one strand, hereinafter referred to as the top strand, of a double-stranded DNA at a specific site and to concomitantly attach a nucleic acid molecule, which comprises an RNA molecule, to the cleaved strand at the cleavage site. The method of cleaving the top strand of a double-stranded DNA substrate comprises the steps of: providing a nucleotide integrase comprising a group II intron RNA having an EBS1 sequence and an EBS2 sequence that are capable of hybridizing with the IBS 1 sequence and the IBS2 sequence, respectively on the top strand of the DNA substrate, and a group II-intron encoded protein capable of binding to or interacting with the first sequence element; and reacting the nucleotide integrase with the double-stranded DNA substrate for a time and at a temperature sufficient to permit the nucleotide integrase to cleave the top strand of the DNA substrate and to insert the group II intron RNA into the cleavage site.

The nucleotide integrase employed in this method comprises a group II intron-encoded protein bound to an excised group II intron RNA. The EBS1 sequence and EBS2 sequence of the group II intron RNA have at least 80%, preferably 90%, more preferably full complementarity with the IBS1 sequence and IBS2 sequence, respectively, that are on the top strand of the substrate. The group II intron-encoded protein comprises an RT domain, an X domain, and the non-conserved portion of the Zn domain.

Figure 1:
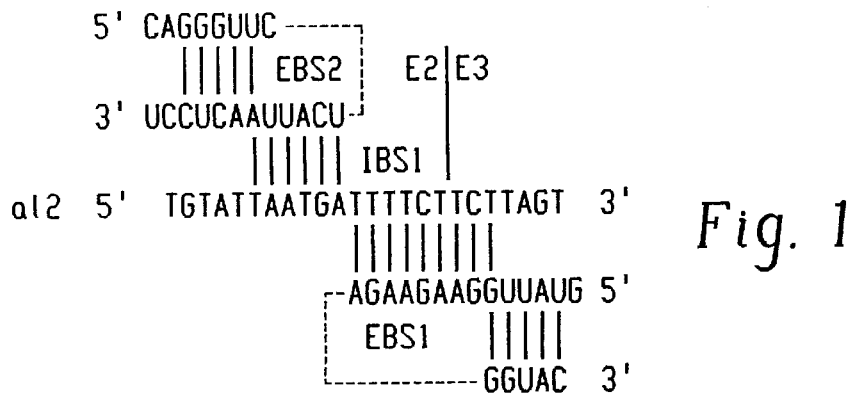
FIG. 1 is a diagram showing the interaction between the EBS sequences of a group II intron RNA of the second intron of the *S. cerevisiae* mitochondrial COX1 gene, hereinafter referred to as the "aI2 intron" RNA and the IBS sequences of a DNA substrate. The cleavage site in the substrate is represented by an arrow.

EBS1 is located in domain I of the group II intron RNA and comprises from about 5 to 7 nucleotides that are capable of hybridizing to the nucleotides of the IBS1 sequence of the substrate. EBS2 is located in domain I of the group II intron RNA upstream of EBS1 and comprises from about 5 to 7 nucleotides that are capable of hybridizing to the nucleotides of IBS2 sequence of the substrate. If the nucleotides of the EBS1 and EBS2 sequences of the group II intron RNA are not at least 80% complementary to the nucleotides of the IBS1 or IBS2 sequences, respectively, then the group II intron RNA is modified to increase the complementarity between the EBS and IBS sequences. As shown in FIG. 1, the IBS1 sequence of the substrate is upstream of the cleavage site and the IBS2 sequence of the substrate is upstream of the IBS1 sequence.

In order to cleave the substrate efficiently, it is preferred that the nucleotide, delta, which immediately precedes the first nucleotide of EBS 1 of the group II intron RNA, be complementary to the nucleotide at +1 in the top strand of the substrate. Thus, if the delta nucleotide is not complementary to the nucleotide at +1 on the top strand of the substrate, the group II intron RNA is modified to contain a delta nucleotide which is complementary to the nucleotide at +1 on the top strand of the substrate. The nucleotide integrase is then reacted with the substrate.

The DNA substrate has a recognition site which comprises a first intron RNA binding sequence that is located on the top strand of the substrate and upstream of the cleavage site and a second intron RNA binding sequence upstream that is located on the top strand of the DNA substrate and upstream of the IBS1 sequence. The recognition site also comprises a first sequence element that is located upstream of the IBS2 sequence and a second sequence element that is located downstream of the cleavage site. The first sequence element and the second sequence element both comprise from about 10 to 12 pairs of nucleotides. The first sequence element contains one or more nucleotide pairs that are required for cleavage by a particular nucleotide integrase. Except for the nucleotide pairs that are required for cleavage, it is preferred that the first sequence element comprise more A-T base pairs than G-C base pairs. It is also preferred that the second sequence element, particularly the first five pairs of nucleotides downstream from the cleavage site, be G/C poor.

Figure 3:
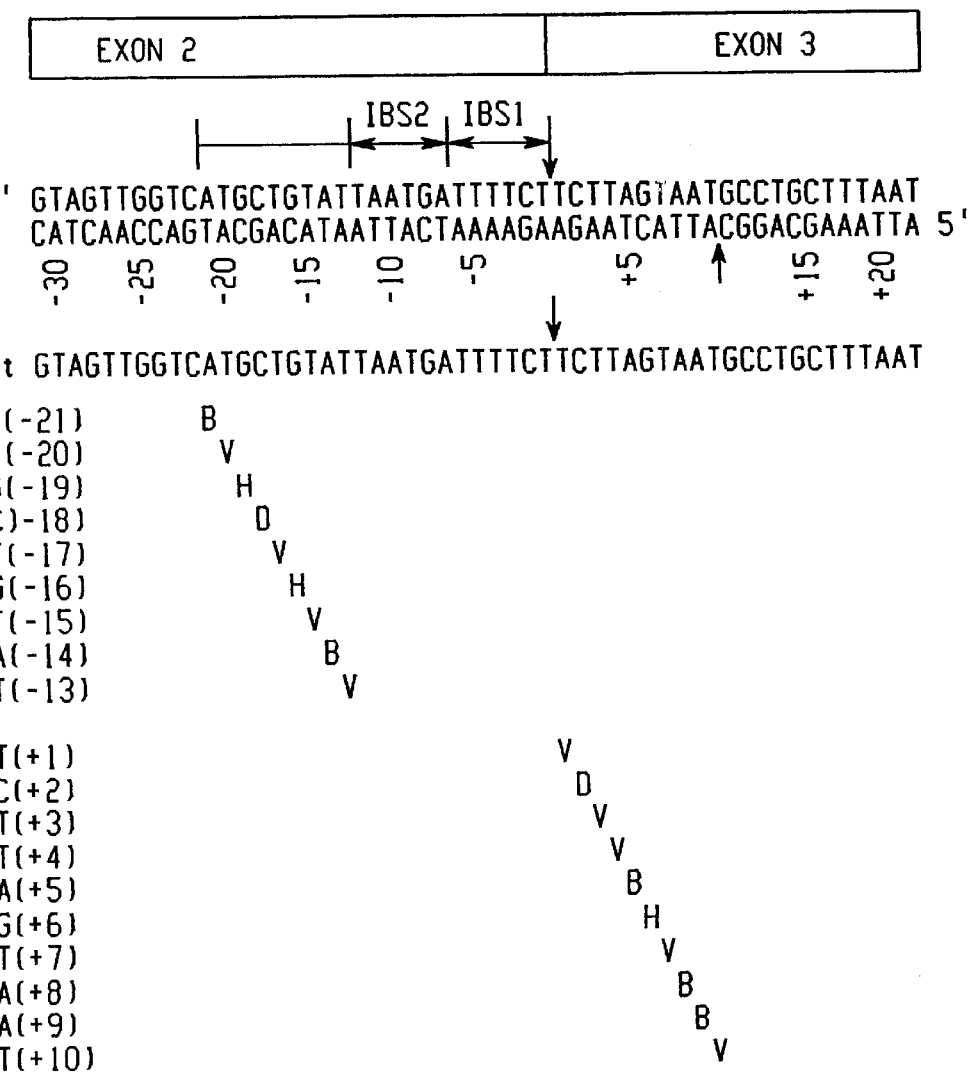
FIG. 3 is a chart depicting the wild-type sequence SEQ ID NO: 2 of the E2/E3 junction of the yeast mitochondrial COX 1 gene and the position of the point mutations made in the wild-type sequence.

Suitable nucleotide integrases for use in this method include, for example the aI2 nucleotide integrase, the aI1 nucleotide integrase, and the ltrA nucleotide integrase. The aI2 integrase is an isolated ribonucleoprotein particle that comprises a wild-type or modified group II intron RNA of the second intron of the *S. cerevisiae* mitochondrial COX1 gene, hereinafter referred to as the "aI2 intron" RNA, bound to a wild-type or modified aI2 intron encoded-protein. The sequence of the wild-type aI2 intron RNA is set forth in SEQ.ID.NO. 1. The sequence of the protein encoded by the wild-type aI2 intron RNA is set forth in SEQ.ID.NO. 7. EBS1 of the aI2 intron RNA comprises 6 nucleotides and is located at position 2985–2990 of the sequence set forth in SEQ. ID. NO. 1. EBS1 of the wild-type aI2 intron RNA has the sequence 5'-AGAAGA. EBS2 of the aI2 intron RNA comprises 6 nucleotides and is located at positions 2935–2940. EBS2 of the wild-type aI2 intron RNA has the sequence 5'-UCAUUA.

aI2 nucleotide integrases are used to cleave double-stranded substrates that have on the top strand thereof the wt sequence, SEQ ID NO: 2, shown in FIG. 3 or a target sequence that differs from the wt sequence, SEQ ID NO: 2, shown in FIG. 3. The aI2 target sequence has a T at positions −15 and −13 relative to the putative cleavage site, a C at position −18 relative to the putative cleavage site, and a G at position −16 or position −19 relative to the putative cleavage site Thus, to use the aI2 nucleotide integrase, one first examines the sequence of the top strand of the substrate to locate a target sequence 5'GCXXTXT or a target sequence 5'XCXGTXT, wherein X represents A,C,G,or T; and wherein A represents a nucleotide having an adenine base, G represents a nucleotide having a guanine base, C represents a nucleotide have a cytosine base, and T represents a nucleotide have a thymine base. Then, if the EBS2 sequence of the aI2 intron RNA does not have substantial complementarity to the IBS2 sequence, i.e., the sequence of 6 nucleotides that lie immediately downstream from one of these target sequences, and/or if EBS1 sequence of the aI2 intron RNA does not have substantial complementarity to the IBS1 sequence, i.e., the sequence of six nucleotides that lie immediately downstream of the IBS2 sequence, then EBS1 and EBS2 are modified to have substantial complementarity, as hereinafter explained. The efficiency of cleavage by the aI2 nucleotide integrase is increased if the top strand of the substrate has an A at −21, a G at −19, a C at −18, a G at −16 a T at −15, and a T at −13.

Figure 6:
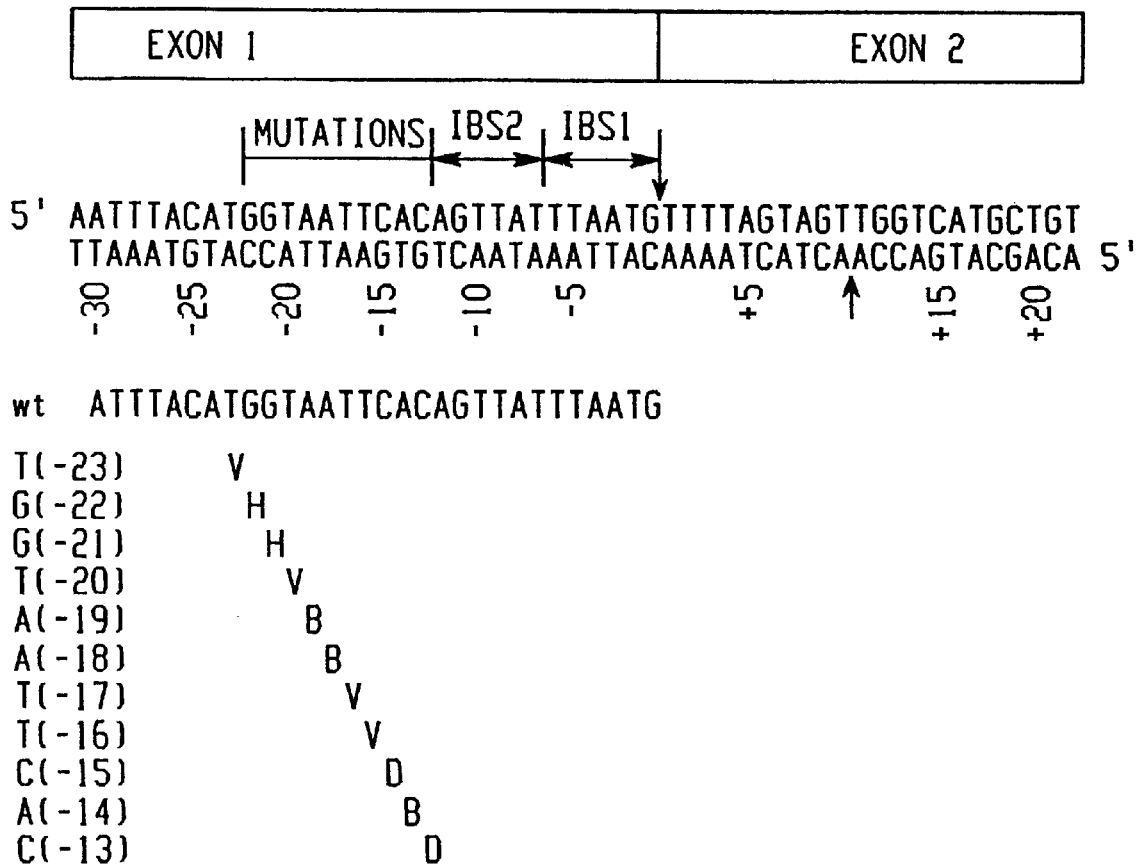
FIG. 6 is a chart depicting the wild-type sequence SEQ ID. NO: 3 of the E1/E2 junction of the yeast mitochondrial COX 1 gene and the position of the point mutations made in the wild-type sequence.
Figure 7:
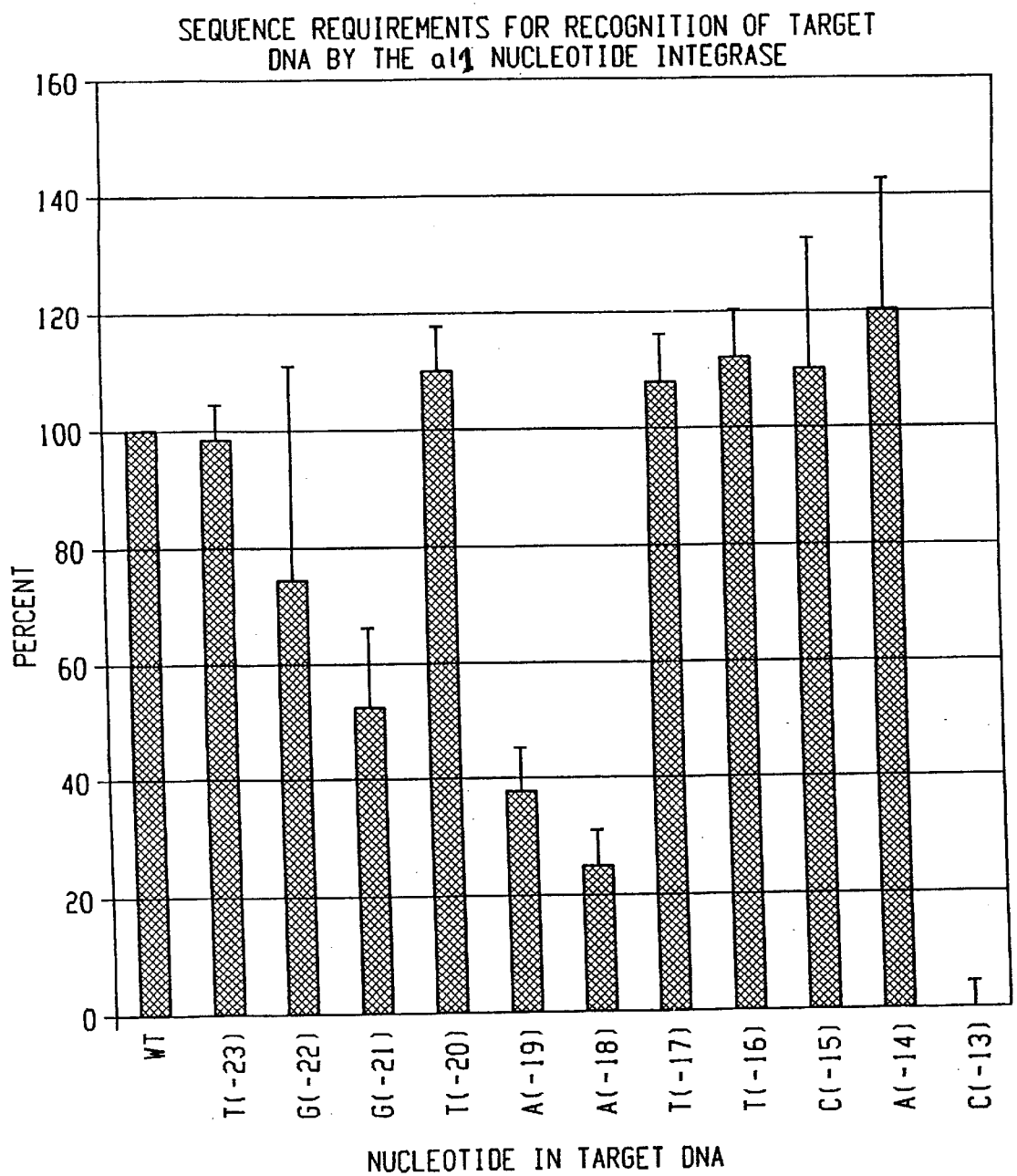
FIG. 7 is a graph showing the relative extent of cleavage of the substrates having mutations upstream of the cleavage site by a nucleotide integrase comprising a wild-type aI1 intron RNA the protein encoded thereby.

The aI1 nucleotide integrase is an isolated ribonucleoprotein particle that comprises an excised, wild-type or modified excised group II intron RNA of the first intron of the *S. cerevisiae* mitochondrial COX1 gene, hereinafter referred to as the "aI1 intron" RNA, and a wild-type or modified aI1 intron-encoded protein. The sequence of the aI1 intron RNA is set forth in SEQ.ID.NO. 1. The sequence of the protein encoded by the aI1 intron RNA is set forth in SEQ.ID.NO. 12. EBS1 of the aI1 intron RNA comprises 6 nucleotides and is located at position 426–431. EBS1 of the wild-type aI1 intron RNA has the sequence 5'-CGUUGA. EBS2 of the aI1 intron RNA comprises 6 nucleotides and is located at positions 376–381. EBS2 of the wild-type aI1 intron RNA and has the sequence 5'-ACAAUU.

aI1 nucleotide integrases are used to cleave double-stranded DNA substrates that have on the top strand thereof the wt sequence, SEQ ID NO: 3, shown in FIG. 6, or target sequences which differ from the wt sequence, SEQ ID NO 3, shown in FIG. 6. The aI1 target sequence has C at position −13 relative to the putative cleavage site. Preferably, the top strand of the substrate has a C at −13, an A at −18, an A at −19, and a G at −21 relative to the putative cleavage site. If the EBS2 sequence of the aI1 intron RNA does not have substantial complementarity to the IBS2 sequence, i.e., the sequence of 6 nucleotides that lie immediately downstream from the C nucleotide at −13, and/or if EBS1 sequence of the aI1 intron RNA does not have substantial complementarity to the IBS1 sequence, i.e., the sequence of six nucleotides that lie immediately downstream of the IBS2 sequence and immediately upstream of the cleavage site, then the EBS1 sequence and the EBS2 sequence of the group II intron RNA are modified to have substantial complementarity, as hereinafter explained.

The ltrA nucleotide integrase comprises an excised, wild-type or modified excised group Ll.ltrB group II intron RNA of the Lactococcus lactis ltrB gene, hereinafter referred to as the "Ll.ltrB intron" RNA, and a wild-type or modified Ll.ltrB intron-encoded protein, hereinafter referred to as the ltrA protein. The sequence of the Ll.ltrB intron RNA is set forth in SEQ.ID.NO. 5. The sequence of the ltra protein is set forth in SEQ.ID.NO. 7. The EBS1 of the Ll.ltrB intron RNA comprises 7 nucleotides and is located at positions 457 to 463. The EBS1 sequence of the wild-type Ll.ltrB intron RNA has the sequence 5'-GUUGUGG. The EBS2 of the Ll.ltrB intron RNA comprises 6 nucleotides and is located at positions 401 to and including 406. The EBS2 sequence of the wild-type Ll.ltrB intron RNa has the Sequence 5'AUGUGU. The ltrA nucleotide integrase is used to cleave the top strand of a double-stranded DNA substrate when the top strand has the wt sequence, SEQ ID NO:4, shown in FIG. 8 or a target sequence which differs from the wt sequence, SEQ ID NO:4 shown in FIG. 8 The ltrA target sequence has a G at −21, an A at −20, and a T at −4 relative to the cleavage site. The ltrA nucleotide integrase cuts the top strand more efficiently when there is a G at −21, an A at −20 a T at −19, a G at −17, and a G at −15, a C at −12 and a T at −4

Another method uses a nucleotide integrase for cleaving both strands of double-stranded DNA and for attaching the group II intron RNA molecule into the cleavage site of the top strand of the DNA substrate. The nucleotide integrase comprises a group II intron-encoded protein bound to an excised group II intron RNA, wherein the group II intron RNA has an EBS1 sequence and an EBS2 sequence that have substantial complementarity to the IBS1 sequence and IBS2 sequence, respectively, on the top strand of the substrate. EBS1 comprises from about 5 to 7 nucleotides. EBS2 comprises from about 5 to 7 nucleotides. If the nucleotides of EBS1 and EBS2 of the group II intron RNA are not at least 80% complementary to the nucleotides of IBS1 and IBS2, the non-complementary nucleotides are modified, preferably, by recombinant techniques. Preferably, the delta nucleotide of the group II intron RNA is complementary to the nucleotide at +1 in the top strand. If the delta nucleotide is not complementary to the nucleotide at +1, preferably the delta nucleotide is modified to be complementary. The group II intron-encoded protein comprises an RT domain, an X domain, and the conserved and non-conserved regions of a Zn domain. To insert a cDNA into the cleavage site on the bottom strand of the substrate, the group II intron-encoded protein also comprises a reverse transcriptase domain.

The method of cleaving both strands of a double-stranded DNA sequence having a recognition site comprises the steps of: providing a nucleotide integrase comprising a group II intron RNA having two sequences, EBS1 and EBS2, that are capable of hybridizing with two intron RNA-binding sequences, IBS1 and IBS2, on the top strand of the DNA substrate, and a group II-intron encoded protein that binds to a first sequence element and to a second sequence element in the recognition site of the substrate; and reacting the nucleotide integrase with the double-stranded DNA substrate for a time and at a temperature sufficient to permit the nucleotide integrase to cleave both strands of the DNA substrate and to insert the group II intron RNA into the cleavage site of the top strand. The first sequence element of the recognition site is upstream of the putative cleavage site, the IBS1 sequence and the IBS2 sequence. The first sequence element comprises from about 10 to about 12 pairs of nucleotides. The second sequence element of the recognition site is downstream of the putative cleavage site and comprises from about from about 10 to about 12 nucleotides.

Nucleotide integrases that may be employed to cleave both strands of a DNA substrate include, but are not limited to an aI2 nucleotide integrase, an aI1 nucleotide integrase, and an ltrA nucleotide integrase. The preferred recognition site for the aI2 nucleotide integrase comprises on the top strand there of a C at −18, a T at −15, a T at −13, a G at −16 or −19, a T at +1, a T at +4, and a G at +6 relative to the cleavage site. To use the aI2 nucleotide integrase to cleave both strands of the DNA substrate, one first examines the substrate sequence to determine if one strand thereof contains this set of nucleotides. Then, if the EBS2 sequence of the aI2 intron RNA does not have substantial complementarity to the IBS2 sequence of the substrate, i.e., the sequence of 6 nucleotides that lies immediately downstream from the T at −13, and/or if EBS1 sequence of the aI2 intron RNA does not have substantial complementarity to the IBS1 sequence, i.e., the sequence of six nucleotides that lie immediately downstream of the IBS2 sequence and immediately upstream of the T at +1, then the EBS1 sequence and EBS2 sequence of the group II intron RNA are modified to have substantial complementarity, as hereinafter explained. The aI2 nucleotide integrase cleaves both strands of the substrate with greater efficiency if the top strand of the substrate has an A at −21, a G at −19, a C at −18, a G at −16, a T at −15, a T at −13 a T at +1, a T at +4, and a G at +6. The aI2 cleaves both strands of the substrate with even greater efficiency if the top strand has an A at −21, a T at −20, a G at −19, a C at −18, −a T at −17, a G at −16, a T at −15,a T at −13 a T at +1, a T at +4, and a G at +6. If the top strand of the substrate additionally has a C at +2, a T at +3, a T at +7, an A at +8, an A at +9, and a T at +10, cleavage will be even greater.

The aI1 integrase is used to cleave both strands of a DNA substrate that has on the top strand thereof a C residue at position −13 relative to the cleavage site. Preferably, the top strand of the double-stranded substrate has a C at −13, a G at −21, an A at −19, an A at −18, a T at +4, a G at +6, a T at +7, and a G at +9. Cleavage is more efficient if there is a G at −22, a G at −21, an A at −19, an A at 18, a C at −13, a T at +1, a T at +2, a T at +3, a T at +4, a A at +5, a G at +6, a T at +7, an A at +8, a G at +9, and a T at +10 on the top strand of the DNA substrate. If the top strand of the substrate additionally comprises a T at −20, a T at −17, a T at −16, a C at −15, and an A at −14, cleavage will be even greater.

The ltrA nucleotide integrase is used to cleave both strands of a double stranded DNA substrate, when the substrate has on the top strand thereof a G at −21, an A at −20 a C +1, an A at +2, a T at +3, an A at +4, a T at +5, a C at +6, an A at +7, and a T at +8. The ltrA nucleotide integrase cleaves both strands of the substrate more efficiently if the top strand has a G at −21, an A at −20, a T at −19, a G at −17, and G at −15, a C +1, an A at +2, a T at +3, an A at +4, a T at +5, a C at +6, an A at +7, and a T at +8. If the top strand additionally has a C at −22, a C at −18, a T at −16, an A at −14, an A at −13, a T at +9 and a T at +10, cleavage will be even greater.

Another method uses a nucleotide integrase for cleaving a single-stranded nucleic acid substrate, i.e., a single-stranded DNA or RNA, and for attaching the group II intron RNA molecule into the cleavage site. The method comprises the steps: providing a nucleotide integrase comprising: a group II intron RNA having two hybridizing sequences, EBS1 and EBS2, which are capable of hybridizing with two intron RNA-binding sequences, IBS1 and IBS2, respectively on the substrate, and a group II intron encoded protein having an RT domain, an X domain and the non-conserved portions of the Zn domain; and reacting the substrate with the nucleotide integrase. The EBS1 sequence of the group II intron RNA comprises from about 5 to 7 nucleotides and has at least 80%, preferably 90%, and more preferably full complementarity with the nucleotides at positions −1 to about −5 or about −7. The EBS2 sequence of the group II intron RNA comprises 4 to 7 nucleotides and has at least 80%, preferably 90%, more preferably full complementarity with the nucleotides at positions from about −6 to about −13. Preferably, the nucleotide immediately preceding the first nucleotide of EBS1 is complementary to the nucleotide at +1 in the sense strand. More preferably, the three nucleotides immediately upstream of EBS1 are complementary to nucleotides +1 to +3 on the single-stranded substrate.

The present invention also provides a method of determining whether a nucleic acid substrate comprises a particular recognition site. The method comprises the steps of providing a nucleotide integrase capable of cleaving a nucleic acid substrate with a particular recognition site; reacting the nucleotide integrase with the nucleic acid substrate; and assaying for cleavage of the substrate. Cleavage of the substrate indicates that the substrate comprises the particular recognition site. In addition to assaying for fragmentation and alterations in size of the nucleic acid substrate, cleavage may be detected by assaying for incorporation into or attachment of the group II intron RNA to one strand of the nucleic acid substrate.

While a wide range of temperatures are suitable for the methods herein, good results are obtained at a reaction temperature of from about 30° C. to about 42° C., preferably from about 30° to about 37° C. A suitable reaction medium contains a monovalent cation such as $Na^+$ or $K^+$, at a concentration from about 0 to about 300 mM; preferably from about 10 to about 200 mM KCl, and a divalent cation, preferably a magnesium or manganese ion, more preferably a magnesium ion, at a concentration that is less than 100 mM and greater than 1 mM. Preferably the divalent cation is at a concentration of about 5 to about 20mM, more preferably about 10 to about 20 mM. The preferred pH for the medium is from about 6.0–8.5, more preferably about 7.5–8.0.

In the above-described methods it is believed that the single stranded nucleic acid substrates and the top strand of the double-stranded DNA substrate are cut by the excised group II intron RNA. The cleavage that is catalyzed by the excised group II intron RNA is a reverse splicing reaction that results in the insertion, either partially or completely, of the excised group II intron RNA into the cleavage site, i.e. between nucleotides −1 and +1 in the top strand. With partial insertion the group II intron RNA is covalently attached to the +1 nucleotide on the top strand of the cleavage site. It is believed that the bottom strand or antisense strand of the double-stranded DNA substrate is cut by the group II intron-encoded protein. The bottom strand of the double stranded DNA substrate is cut at a position from about 9 to about 11 base pairs downstream of the cleavage site in the top strand, i.e., at a site between nucleotides positions +9, +10, and +11.

The methods of using a nucleotide integrase as an endonuclease to cleave a substrate DNA are useful analytical tools for determining the presence and location of a particular recognition site in a DNA substrate. Moreover, the simultaneous insertion of a nucleic acid molecule into the DNA substrate, which occurs when either single-stranded DNA or double stranded DNA is cleaved with a nucleotide integrase, permits tagging of the cleavage site of the DNA substrate with a radiolabeled molecule, a feature which facilitates in identifying DNA substrates that contain a particular recognition site. In addition, the automatic attachment of an RNA molecule onto one strand of a double-stranded DNA substrate permits identification of the cleavage site through hybridization studies that use a probe that is complementary to the attached RNA molecule. An attached RNA molecule that is tagged with a molecule such as biotin also enables the cleaved strand to be affinity purified.

The methods of using nucleotide integrases to cleave RNA and DNA substrates having a recognition site are useful for rendering certain genes within the substrates nonfunctional. Such methods are also useful for inserting a nucleic acid into the cleavage site, thus, changing the characteristics of the RNA molecules and the protein molecules encoded by the substrates.

The Nucleotide Integrase

The nucleotide integrase is an isolated ribonucleoprotein ("RNP) particle and comprises a group II intron encoded RNA and a group II intron encoded protein, which protein is bound to the RNA. Preferably, the group II intron RNA is an excised group II intron RNA. "Excised group II intron RNA," as used herein, refers to an RNA that is either an in vitro or in vivo transcript of the DNA of the group II intron and that lacks flanking exon sequences. The excised group II intron RNA is obtained from wild type organisms, or mutated organisms, by in vivo transcription and splicing, or by in vitro transcription and splicing from the transcript of a modified or unmodified group II intron. "Group II intron encoded protein" as used herein, is a protein encoded by a group II intron open reading frame.

Figures 2G, 4:
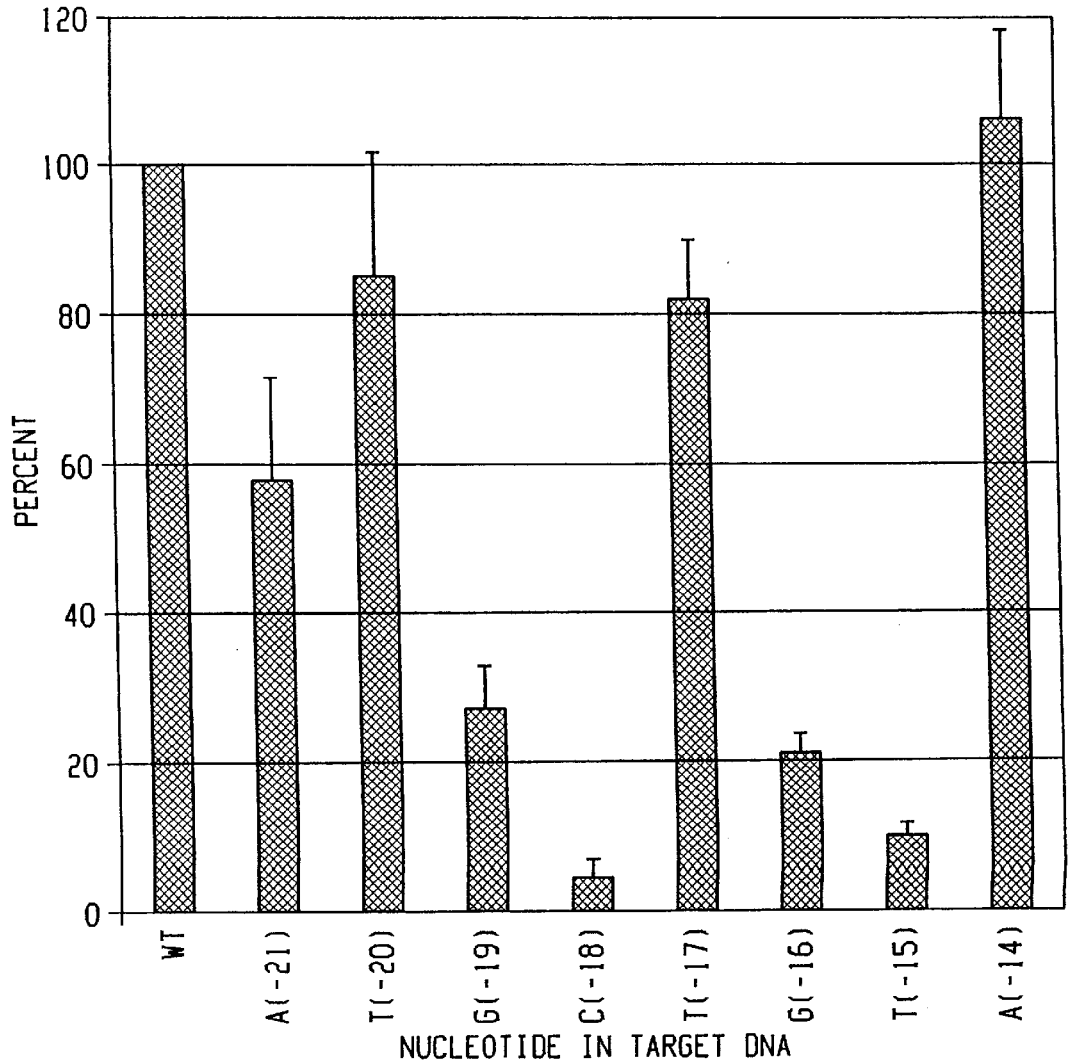
Figure 5:
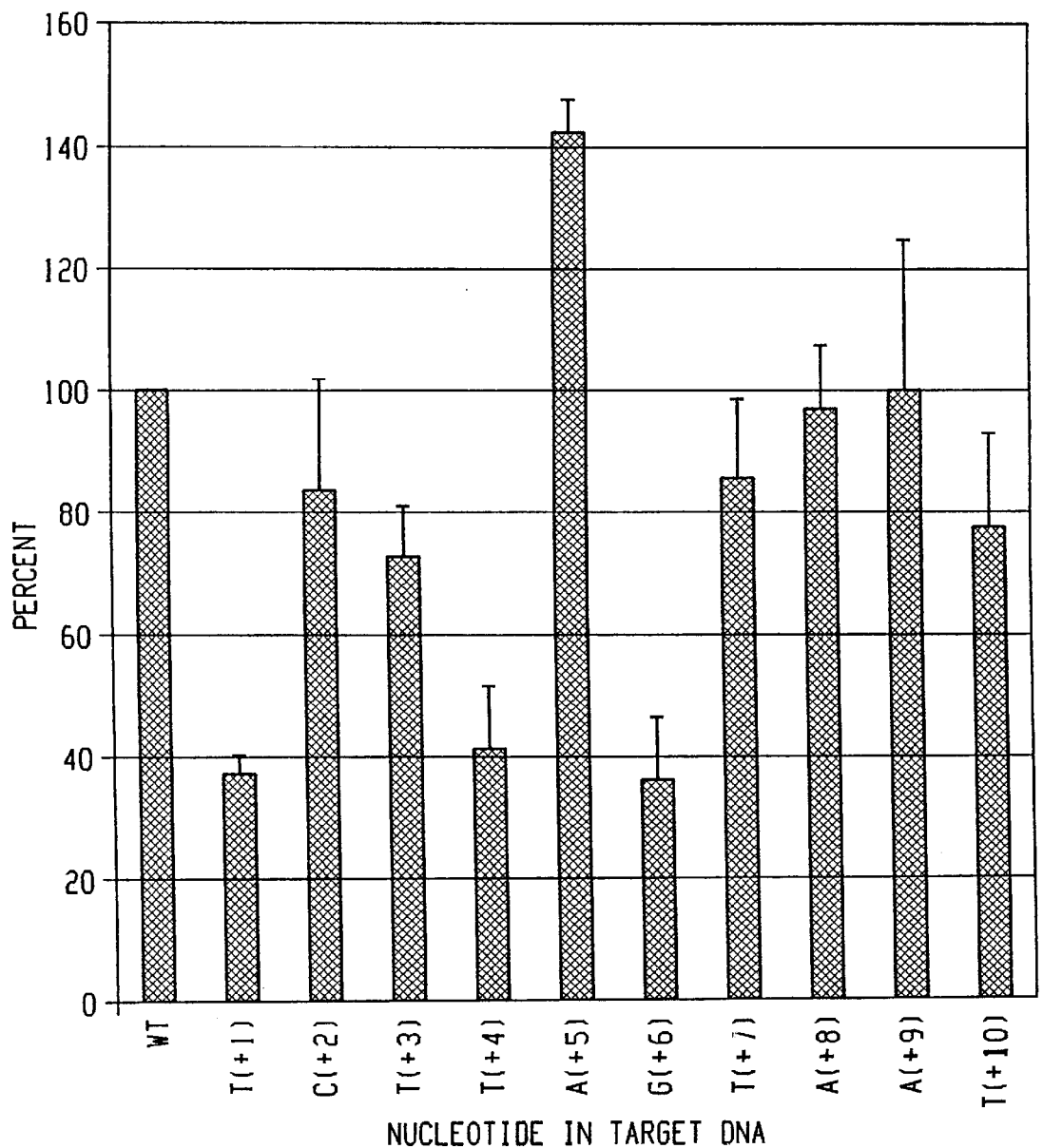
FIG. 5 is a graph showing the relative extent of cleavage of the substrates having mutations in the nucleotides downstream of the cleavage site by a nucleotide integrase comprising a wild-type aI2 intron RNA and the protein encoded by the aI2 intron RNA.

A group II intron is a specific type of intron that is present in the DNA of bacteria and in the DNA of organelles, particularly the mitochondria of fungi, yeast and plants and the chloroplast of plants. The group II intron RNA molecules, that is, the RNA molecules which are encoded by the group II introns, share a similar secondary and tertiary structure. FIG. 2 depicts the secondary structure of the aI1 and aI2 intron RNA and part of the nucleotide sequence of the wild-type aI1 and aI2 intron RNA. The group II intron RNA molecules typically have six domains. Domain IV of the group II intron RNA contains the nucleotide sequence which encodes the "group II intron encoded protein."

Nucleotide integrases include, for example, excised group II intron RNA molecules having a sequence which is identical to a group II intron RNA that is found in nature, i.e. a wild-type group II intron RNA, and excised group II RNA's which have a sequence different from a group II intron RNA that is found in nature, i.e. a modified, excised group II intron RNA molecule. Modified excised group II intron RNA molecules, include, for example, group II intron RNA molecules that have nucleotide base changes or additional nucleotides in the internal loop regions of the group II intron RNA, preferably the internal loop region of domain IV and group II intron RNA molecules that have nucleotide base changes in the hybridizing regions of domain I. Nucleotide integrases in which the group II intron RNA has nucleotide base changes in the hybridizing region, as compared to the wild type, typically have altered specificity for the substrate DNA of the nucleotide integrase.

The group II intron-encoded protein of the nucleotide integrase comprises an X domain and a Zn domain. The X domain of the protein has a maturase activity. The Zn domain of the protein has $Zn^{2+}$ finger-like motifs. Preferably, the group II intron-encoded protein further comprises a reverse transcriptase domain. As used herein, a group II intron-encoded protein includes modified group II intron-encoded proteins that have additional amino acids at the N terminus, or C terminus, or alterations in the internal regions of the protein as well as wild-type group II intron-encoded proteins. It is believed that the group II intron-encoded protein is bound to 3' region of the group II intron RNA.

The nucleotide integrase are provided in the form of RNP particles isolated from wild-type, mutant, or genetically-engineered organisms. The nucleotide integrase are also provided in the form of reconstituted RNP particles isolated from a reconstituted RNP particle preparation. The nucleotide integrase also comprises reconstituted RNP particles that are formed by combining an exogenous synthetic, excised group II intron RNA with either a group II intron-encoded protein or an RNA-protein complex preparation. The exogenous RNA includes both unmodified and modified group II intron RNA molecules. Preferably, the exogenous RNA is an in vitro transcript or a derivative of an in vitro transcript of an unmodified or modified intron group II intron. For example, the exogenous RNA may be derived by splicing from an in vitro transcript. The RNA-protein complex preparation contains group II intron-encoded protein molecules complexed to RNA molecules that are not an excised group II RNA molecule having a sequence which encodes this protein. The group II intron-encoded protein of the RNA-protein complex is associated with either a ribosomal RNA molecule, an mRNA molecule, or an excised group II intron RNA that does not encode the group II-intron encoded protein.

The nucleotide integrase may be used as a purified RNP particle or a purified reconstituted particle. Alternatively, the nucleotide integrase may be used in a partially-purified preparation which contains the RNP particles and reconstituted particles that have nucleotide integrase activity as well as other RNP particles, such as for example ribosomes. This partially-purified preparation is free of organelles.

Preparation of the Nucleotide Integrase

The nucleotide integrase is isolated from wild type or mutant yeast mitochondria, fungal mitochondria, plant mitochondria, chloroplasts, the proteotobacterium *Azotobacter vinelandii,* the cyanobacterium Calothrix, and *Escherichia coli lactococcus lactis.* The procedure for isolating the RNP particle preparation involves mechanically and/or enzymatically disrupting the cell membranes and/or cell walls of the organisms. In the case of fungi and plants, the purification also involves separating the specific organelles, such as mitochondria or chloroplasts, from the other cellular components by differential centrifugation and/or flotation gradients and then lysing the organelles with a nonionic detergent, such as Nonidet P-40. The organelle and bacterium lysates are then centrifuged through a sucrose cushion to obtain the ribonucleoprotein (RNP) particle preparation. The RNP particles may be further purified by separation on a sucrose gradient, or a gel filtration column, or by other types of chromatography.

The nucleotide integrase is also isolated from reconstituted RNP particle preparations that are prepared by combining an RNA-protein complex preparation with an exogenous, excised group II intron RNA. The RNA-protein complex preparation is preferably isolated from a yeast, fungi, or bacterium using the protocol for RNP particles described above. The RNA-protein complex preparation comprises group II intron-encoded protein molecules complexed with RNA molecules that are not an excised group II intron RNA having a sequence that encodes the group II intron-encoded protein. The group II intron-encoded protein of the RNA-protein complex preparation is associated with either a ribosomal RNA molecule, an mRNA molecule, or an excised group II intron RNA that does not encode the group II-intron encoded protein.

The exogenous RNA preferably is a synthetic molecule made by in vitro transcription or by in vitro transcription and self-splicing of the group II intron. The exogenous RNA may also be made by isolation of the group II intron RNA from cells or organelles in which it is naturally present or from cells in which an altered intron has been inserted and expressed. The exogenous RNA is then added to a preparation containing the RNA-protein complex. Preferably, the exogenous group II intron RNA is first denatured. The exogenous RNA is added to the RNA-protein complex on ice.

In another embodiment, the nucleotide integrase is made by introducing an isolated DNA molecule which comprises a group II intron DNA sequence into a host cell. Suitable DNA molecules include, for example, viral vectors, plasmids, and linear DNA molecules. Following introduction of the DNA molecule into the host cell, the group II intron DNA sequence is expressed in the host cell such that excised RNA molecules encoded by the introduced group II intron DNA sequence and protein molecules encoded by introduced group II intron DNA sequence are formed in the cell. The excised group II intron RNA and group II intron-encoded protein are combined within the host cell to produce the nucleotide integrase.

Preferably the introduced DNA molecule also comprises a promoter, more preferably an inducible promoter, operably linked to the group II intron DNA sequence. Preferably, the DNA molecule further comprises a sequence which encodes a tag to facilitate isolation of the nucleotide integrase such as, for example, an affinity tag and/or an epitope tag. Preferably, the tag sequences are at the 5' or 3' end of the open reading frame sequence. Suitable tag sequences include, for example, sequences which encode a series of histidine residues, the Herpes simplex glycoprotein D, i.e., the HSV antigen, or glutathione S-transferase. Typically, the DNA molecule also comprises nucleotide sequences that encode a replication origin and a selectable marker. Optionally, the DNA molecule comprises sequences that encode molecules that modulate expression, such as for example T7 lysozyme.

The DNA molecule comprising the group II intron sequence is introduced into the host cell by conventional methods, such as, by cloning the DNA molecule into a vector and by introducing the vector into the host cell by conventional methods, such as electroporation or by $CaCl_2$-mediated transformation procedures. The method used to introduce the DNA molecule is related to the particular host cell used. Suitable host cells are those which are capable of expressing the group II intron DNA sequence. Suitable host cells include, for example, heterologous or homologous bacterial cells, yeast cells, mammalian cells, and plant cells. In those instances where the host cell genome and the group II intron DNA sequence use different genetic codes, it is preferred that the group II intron DNA sequence be modified to comprise codons that correspond to the genetic code of the host cell. The group II intron DNA sequence, typically, is constructed de novo from synthetic oligonucleotides or modified by in vitro site-directed mutagenesis to prepare a group II intron DNA sequence with different codons. Alternatively, to resolve the differences in the genetic code of the intron and the host cell, DNA sequences that encode the tRNA molecules which correspond to the genetic code of the group II intron are introduced into the host cell. Optionally, DNA molecules which comprise sequences that encode factors that assist in RNA or protein folding, or that inhibit RNA or protein degradation are also introduced into the cell.

The DNA sequences of the introduced DNA molecules are then expressed in the host cell to provide a transformed host cell. As used herein the term "transformed cell" means a host cell that has been genetically engineered to contain additional DNA, and is not limited to cells which are cancerous. Then the RNP particles having nucleotide integrase activity are isolated from the transformed host cells.

Preferably, the nucleotide integrase is isolated by lysing the transformed cells, such as by mechanically and/or enzymatically disrupting the cell membranes of the transformed cell. Then the cell lysate is fractionated into an insoluble fraction and soluble fraction.

Preferably, an RNP particle preparation is isolated from the soluble fraction. RNP particle preparations include the RNP particles having nucleotide integrase activity as well as ribosomes, mRNA and tRNA molecules and other RNPs. Suitable methods for isolating RNP particle preparations include, for example, centrifugation of the soluble fraction through a sucrose cushion. The RNP particles, preferably, are further purified from the RNP particle preparation or from the soluble fraction by, for example, separation on a sucrose gradient, or a gel filtration column, or by other types of chromatography. For example, in those instances where the protein component of the desired RNP particle has been engineered to include a tag such as a series of histidine residues, the RNP particle may be further purified from the RNP particle preparation by affinity chromatography on a matrix which recognizes and binds to the tag. For example, NiNTA Superflow from Qiagen, Chatsworth Calif., is suitable for isolating RNP particles in which the group II intron-encoded protein has a $His_6$ tag.

The following methods for preparing nucleotide integrases are included for purposes of illustration and are not intended to limit the scope of the invention.

Formulations

The RNP particle preparations of the following formulations 1–10, and the RNA-protein complex of the formulation 12 were isolated from the mitochondria of the wild-type *Saccharomyces cerevisiae* yeast strain ID41-6/161 MATa ade1 lys1, hereinafter designated "161", and derivatives thereof. The mitochondria of the wild-type yeast strain 161 contains a COX1 gene that includes the group II intron aI1 and the group II intron aI2.

The COX1 gene in the mutant yeast strains either lacks one of the group II introns or has a mutation in one of the group II introns. The excised group II intron RNA molecules and the group II intron encoded proteins are derived from the group II introns aI1 and aI2 that are present in the wild-type and mutant yeast strains.

The intron composition of the COX1 gene in the different yeast strains is denoted by a convention in which a superscript "+" indicates the presence of the aI1 intron or the aI2 intron, a superscript "0" indicates the absence of the aI1 or aI2 intron, and other superscripts refer to specific alleles or mutations in the aI2 intron.

Formulation 1

An RNP particle preparation was isolated from the mitochondria of the *Saccharomyces cerevisiae* wild-type yeast strain 161. The intron composition of the COX1 gene of the wild-type strain is $1^+2^+$. The RNP particle preparation contains an RNP particle that is derived from the aI1 intron and includes an excised aI1 RNA bound to a protein encoded by aI 1. The preparation also contains an RNP particle that is derived from the aI2 intron and that comprises a excised aI2 RNA molecule and an associated aI2-encoded protein.

To prepare the RNP particle preparation, the yeast were inoculated into a 1 liter liquid culture medium containing 2% raffinose, 2% BactoPeptone from Difco and 1% yeast extract from Difco to an $O.D._{595}$ of 1.6–1.7. The cell walls were digested with 40 mg of the yeast lytic enzyme from ICN, and the cells broken by mechanical disruption with glass beads. The nuclei and cell debris were pelleted from the lysate by centrifugation for 5 minutes in a Beckman GSA rotor at 5,000 rpm. The supernatant was removed and centrifuged in a Beckman GSA rotor at 13,000 rpm for 15 minutes to obtain a mitochondrial pellet. The mitochondria were layered on a flotation gradient consisting of a 44% sucrose solution layer, a 53% sucrose solution layer, and a 65% sucrose solution layer and centrifuged in a Beckman SW28 rotor at 27,000 rpm for 2 hours and 10 minutes. The mitochondria were collected from the 53%/44% interface and suspended in buffer containing 0.5M KCl, 50 mM $CaCl_2$, 25 mM Tris-HCl, pH 7.5, 5 mM DTT and lysed by the addition of Nonidet P-40 to a final concentration of 1%. The mitochondrial lysate was then centrifuged in a Beckman 50Ti rotor at 50,000 rpm for 17 hours through a 1.85 M sucrose cushion in a buffer containing 0.5M KCl, 25 mM $CaCl_2$, 25 mM Tris-HCl, pH 7.5, 5 mM DTT, to obtain a pellet of RNP particles that were largely free of mitochondrial proteins. The isolated RNP particles were resuspended in 10 mM Tris-HCl, pH 8.0 and 1 mM DTT and stored at −70° C. The preparation may be repeatedly thawed and frozen before use.

Formulation 1a Purified RNP Particle 2.5 $O.D._{260}$ of the RNP particles from formulation 1 in a volume of 150 µl were layered onto a 12 ml 5–20% linear sucrose gradient in a buffer consisting of 100 mM KCl, 2 mM $MgCl_2$, 50 mM Tris-HCl, pH 7.5, and 5 mM DTT. The gradient was centrifuged in an SW41 rotor at 4° C. at 40,000 rpm for five hours. The gradient was fractionated into 35 fractions of approximately 0.325 ml. Fractions 12–20 contain the purified RNP particles which are substantially free of ribosomal RNA. The location of the RNP particles in the gradient fractions was independently verified by Northern hybridization with aI2 antisense RNA. The location of the small and large subunits of ribosomal RNA in the gradient fractions was independently verified by ethidium bromide staining of the fractions on a 1% agarose gel. Approximately 85% of the ribosomal RNA is found in a fraction that does not contain the RNP particles which comprise the nucleotide integrase.

Formulation 2 RNP Particle Preparation from Mutant Yeast Strain $1^02^+$

The RNP particles comprise an excised aI2 RNA and an aI2-encoded protein. Yeast strain $1^02^{+t}$ was obtained from Dr. Philip S. Perlman at the University of Texas Southwestern Medical Center and was prepared as described in Moran et al., 1995, *Mobile Group II Introns of Yeast Mitochondrial DNA Are Novel Site-Specific Retroelements,* Mol. Cell Biol. 15, 2828–38, which is incorporated herein by reference. The $1^02^{+t}$ mutant strain was constructed as follows: (i) the aI2 intron from strain 161 was cloned as a ClaI-to-BamHI fragment into pBluescript KS+ obtained from Stratagene to yield pJVM4; (ii) pJVM4 was cleaved with ClaI and NdeI to remove the 5' end of the insert; and (iii) an MspI-to-NdeI fragment that contains exons 1 and 2 of the mitochondriae COX1 gene plus the 5' end of aI2 from yeast strain C1036ΔI was inserted to yield plasmid pJVM164. Yeast strain C1036ΔI, in which aI1 is excised from the mitochondrial DNA, was prepared as described in Kennell et al., 1993, *Reverse transcriptase activity associated with maturase-encoding a group II introns in yeast mitochondria.* Cell 73, 133–146, which is incorporated herein by reference. pJVM164 was transformed into a [rho⁰] strain, and the $1^02^{+t}$ allele was placed into an intact mitochondrial DNA by recombination. This last step is accomplished by mating to a nonreverting COX1 mutant derived from mutant C1036 (strain 5B), whose construction is described in Kennel et al., 1993, and selecting for recombinant progeny that are capable of respiring and growing on glycerol-containing medium (GLY⁺) and that contain the transformed COX1 allele in place of the 5B allele.

The reactions and manipulations directed at cloning DNA, such as ligations, restriction enzyme digestions, bacterial transformation, DNA sequencing etc. were carried out according to standard techniques, such as those described by Sambrook et al., *Molecular cloning: a laboratory manual*, 2nd ed., Cold Spring Harbor Laboratory Press. Cold Spring Harbor, N.Y. Yeast mitochondrial transformations were also carried out according to standard techniques such as those described in Belcher et al., 1994, Biolistic transformation of mitochondria in *Saccharomyces cerevisiae*, 101–115. In N.-S. Yang and P. Christou (ed.) *Particle Bombardment Technology for Gene Transfer.* Oxford University Press, New York. The RNP particle preparation was made from the mitochondria of mutant yeast strain $1°2^+$, as in formulation 1.

Formulation 3 RNP Particle Preparation from Mutant Yeast Strain $1^{+/}2°$

Yeast strain $1^{+/}2°$ is a derivative of the wild-type yeast strain 161. The yeast strain $^{+/}2°$ was obtained from Dr. Philip S. Perlman and was prepared as described in Kennell et al., 1993. Cell 73, 133–146. Yeast strain $1^{+/}2°$ contains a segment of the COX1 gene of *S. diastaticus*, which lacks aI2, inserted into wild-type 161 mtDNA via mitochondrial transformation. The construction started with plasmid pSH2, which contains aI1 from wild-type 161 and some flanking sequences cloned as a HpaII/EcoRI fragment in pBS(+) (Stratagene, La Jolla, Calif.). That plasmid was cleaved near the 3' end of aI1 with ClaI and in the downstream polylinker with BamHI, and the gap was filled with a ClaI/BamHI fragment from *S. diastaticus* mitochondrial DNA (NRRL Y-2416) that contains the 3' end of aI1, E2, E3 and most of aI3, thus creating a $1^{+/}2°$ form of the COX1 gene. The plasmid containing the hybrid COX1-$1^{+/}2°$ segment was transformed into a rho° derivative of strain MCC109 (MATa ade2-101 ura3-52 kar1-1) by biolistic transformation. The resulting artificial petite was crossed to strain n161/m161-5B, and gly⁺recombinants containing the COX1 $1^{+/}2°$ allele in the n161 background were isolated. The hybrid aI1 allele, which is spliced normally, differs from that of wild-type 161 by one nucleotide change, C to T, at position 2401, changing Thr$_{744}$ to Leu in the intron open reading frame. The RNP particle preparation was made from the mitochondria of mutant yeast strain $I^{+/}2°$ as in formulation 1. The RNP particles comprise an excised aI1 RNA molecule and an aI1 encoded protein.

Formulation 4 RNP Particle Preparation from Mutant Yeast Strain $1°2^{YAHH}$

Yeast strain $1°2^{YAHH}$ was obtained from Dr. Philip S. Perlman and was made as described in Moran et al., 1995, Mol. Cell Biol. 15, 2838–38., using a mutagenized pJVM164 plasmid. The allele was made by oligonucleotide-directed mutagenesis of pJVM164 which contains a 4.4 kb MspI/BamHI fragment extending from 217 nucleotides upstream of exon 1 through intron aI3 of the COX1 allele. The mutagenesis changes the aI2 nucleotides 1473 to 1478 from GAT GAT to CAT CAT (D-491D-492 to HH). The RNP particles comprise a mutated, excised aI2 RNA and an aI2-encoded protein that has the mutation YADD®YAHH in the reverse transcriptase domain of the protein. The RNP particle preparation was made from the mitochondria of mutant yeast strain $1°2^{YAHH}$ as in formulation 1.

Formulation 5 RNP Particles from the Mutant Yeast Strain $1°2^{P714T}$

The mutant yeast strain $1°2^{P714T}$ was obtained from Dr. Philip S. Perlman and was constructed according to the procedure described in Kennell et al., 1993, *Cell* 73, 133–146, where it is named n161/m161-C1036Δ1. The RNP particles comprise a mutated, excised aI2 intron RNA molecule and an aI2-encoded protein that carries the missense mutation $P_{714}T$ in the Zn domain. The RNP particle preparation was made from mitochondria of mutant yeast strain $1°2^{P714T}$ as in formulation 1.

Formulation 6 RNP Particle from Mutant Yeast Strain $1°2^{HHVR}$

The mutant yeast strain $1°2^{HHVR}$ was obtained from Dr. Philip S. Perlman and was made by using the nucleotide described in Moran et al., 1995, Mol. Cell Biol. 15, 2828–38, which is incorporated herein by reference, using a mutagenized pJVM164 plasmid. The allele was constructed by site-directed mutagenesis of pJVM164. The aI2 intron has the following changes: positions 2208–2219 from CAT-CACGTAAGA SEQ. ID. NO. 8 to GCAGCTGCAGCT SEQ ID NO: 9, ($H_{736}H_{737}V_{738}R_{739}$ to AAAA) and $A_{2227}$ A to T ($N_{742}I$). This nucleotide integrase preparation comprises a mutated, excised aI2 intron RNA and an aI2-encoded protein that has a missense mutation in the HHVR motif. The RNP particle preparation was made from mitochondria of mutant yeast strain $1°2^{HHVR}$.

Formulation 7 RNP Particle from Mutant Yeast Strain $1°2^{\Delta ConZn}$

The mutant yeast strain $1°2^{\Delta-ConZn}$ was obtained from Dr. Philip S. Perlman and was made as described in Moran et al., 1995, Mol. Cell Biol. 15, 2828–38, using a mutagenized pJVM164 plasmid. The allele was constructed by oligonucleotide-directed mutagenesis of pJVM164. The aI2 intron has the following changes:positions 2157–2165 changed from TTATTTAGT to TAATAATAA ($L_{719}F_{720}S_{721}$ to OchOchOch). RNP particles comprise a mutated, excised aI2 intron RNA and an aI2-encoded protein that lacks the most conserved motifs in the Zn domain. The RNP particle preparation was made from mitochondria of mutant yeast strain $1°2^{\Delta ConZn}$.

Formulation 8 RNP Particle from Mutant Yeast Strain $1°2^{C-C/1}$

The mutant yeast strain $1°2^{C-C/1}$ was obtained from Dr. Phillip S. Perlman and was made by using a nucleotide described in Moran et al., 1995 Mol. Cell Biol. 15, 2828–38, using a mutagenized pJVM164 plasmid. The allele was constructed by site-directed mutagenesis of pJVM164. The aI2 intron has the following changes:positions 2172–2173 changed from TG to GC ($C_{724}A$) and 2180–2182 changed from TTG to AGC ($1_{726}C_{727}$ to MA). The RNP particles comprise a mutated, excised aI2 intron RNA and an aI2-encoded protein that has three amino acid residues changed in the first $Zn^{+2}$-finger-like motif. The RNP particle preparation was made from mitochondria of mutant yeast strain $1°2^{C-C/1}$.

Formulation 9 RNP Particles from Mutant Yeast Strain $1°2^{C-C/2}$

The mutant yeast strain $1°2^{C-C/2}$ was obtained from Dr. Philip S. Perlman and was made as described in Moran et al., 1995 Mol. Cell Biol. 15,2828–38, using a mutagenized pJVM164 plasmid. The allele was constructed by site-directed mutagenesis of pJVM164. The aI2 intron has the following changes: position 2304–2305 changed from TG to GC ($C_{768}A$) and 2313–2314 changed from TG to GC ($C_{771}A$). The RNP particles comprise a mutated excised aI2 intron RNA and an aI2-encoded protein that has two amino acids changed in the second $Zn^{+2}$ finger-like motif. The RNP particle preparation was made from mitochondria of mutant yeast strain $1°2^{C-C/2}$.

Formulation 10 RNP Particles from Mutant Yeast Strain 1°2$^{H6}$

The mutant yeast strain, obtained from Dr. Philip S. Perlman, was made by transferring the mutagenized plasmid pJVM 164 into the mitochondria of yeast strain GRF 18 as described in Moran et al., 1995 Ref. The allele was constructed by site-directed mutagenesis of pJVM164 and has the sequence CATCATCATCATCATCAT, SEQ. ID. NO. 10, inserted between nucleotides 2357 and 2358 of the aI2 intron. The RNP particle preparation was made from mitochondria of mutant yeast strain 1°2$^{H6}$ according to the protocol described above for formulation 1. The RNP particles comprise a mutated, excised aI2 intron RNA and an aI2-encoded protein that has six histidines added to the C terminus of the aI2-encoded protein.

Formulation 11 RNP Particles from Neurospora Intermedia

Mitochondria from the Varkud strain of Neurospora intermedia, which is available from the Fungal Genetics Stock Center, were prepared as described in Lambowitz A.M. 1979, Preparation and analysis of mitochondrial ribosomes. Meth. Enzymol. 59, 421–433. The conidia were disrupted with glass beads and the mitochondria and RNP particles isolated as described in formulation 1. The RNP particles comprise an excised coI intron RNA and the protein encoded by the coI intron.

Formulation 12 Reconstituted RNP Particle Preparation

A reconstituted RNP particle preparation was made by incubating an exogenous, excised, in vitro RNA transcript of the aI2 intron with an RNA-protein complex preparation isolated from the mutant yeast strain 1°2$^{\Delta D5}$, in which the aI2 intron RNA lacks a domain V and is therefore splicing defective. The mutant allele 1°2$^{\Delta D5}$ was obtained from Dr. Philip S. Perlman and was constructed using the same procedure that was used to make yeast strain 1$^{+}$2$^{\Delta D5}$ that was described in Moran et al. 1995, except that the final mating was with yeast strain 1°2$^{+}$. The RNA-protein complex preparation was isolated from 1°2$^{\Delta D5}$ using the protocol described above in formulation 1 for RNP particle preparations. The RNA-protein complex preparation isolated from the mitochondria of 1°2$^{\Delta D5}$ does not contain excised aI2 RNA but does contain aI2-encoded protein that is associated with other RNA molecules in the preparation.

The exogenous RNA was made by in vitro transcription of the plasmid pJVM4 which includes a fragment of the yeast mitochondrial COX1 gene from the ClaI site of the group II intron 1 (aI1) to the BamHI site of aI3 that has been inserted into the pBLUESCRIPT KS+ plasmid. Plasmid pJVM4 contains the following COX1 sequences: Exon 2, aI2, Exon 3 and parts of aI1 and aI3 sequence. The sequences are operably linked to a T3 RNA polymerase promoter. The Exon 2 and Exon 3 sequence are required for self-splicing of the aI2 intron RNA from the RNA transcript. pJVM4 was linearized with BstEII, which cuts at the 3' end of Exon 3 then 5 μg of the plasmid was incubated in 0.300 ml of 40 mM Tris-HCl at pH 8.0, 25 mM NaCl, 8 mM MgCl$_2$ 2 mM spermidine, 5 mM DTT 500 mM rNTPs, 600 U of RNasin from US Biochemical and 300–750 U of T3 RNA polymerase from BRL at 37° C. for 2 hours to make the RNA transcripts. Following the incubation, the RNA transcripts were phenolcia extracted, purified on G-50 column, phenolcia extracted and precipitated with ethanol. The RNA transcripts were then incubated in 40 mM Tris-HCl at pH 7.5, 100 mM MgCl$_2$, 2 M NH$_4$Cl at 40–45° C. for 1 hour to allow self-splicing of the aI2 intron RNA molecules from the RNA transcripts and to obtain the splicing products. The splicing products, which include the excised aI2 RNA transcript, the ligated transcript which lacks the aI2 intron RNA, and the unspliced transcript, were desalted by passing through a G-50 column, then phenolcia extracted and ethanol precipitated to provide the exogenous RNA. The exogenous RNA was then resuspended to a final concentration of 1.0 mg/ml in 10 mM Tris-HCl, pH 8.0, 1 mM EDTA.

To prepare the reconstituted RNP particle preparation, 1 μl of the exogenous RNA was added to 2 μl of the 1°2$^{\Delta D5}$ RNA-protein complex preparation (0.025 O.D.$_{.260}$ units) on ice for 0–10 minutes. The preparation was used immediately.

Formulation 13 Reconstituted RNP Particle Preparation Containing a Nucleotide Integrase Comprising a Group II Intron RNA Having Modified EBS Sequences Plasmid pJVM4 derivatives were used to prepare exogenous aI2 intron RNA molecules in which the EBS1 and EBS2 sequences are different from the EBS sequences in the wild-type aI2 intron. pJVM4 contains the aI2 intron sequence and flanking exon sequences from wild-type yeast 161 cloned downstream of a phage T3 promoter in pBluescript II KS(+). Plasmids containing modified introns were derive s from pJVM4 by PCR mutagenesis with appropriate primers. In al1 cases, the modified region was sequenced to verify the correct mutation and the absence of adventitious mutations.

Plasmids pJVM4-aI1EBS1, pJVM4-aI1EBS2 and pJVM4-aI1EBS1/EBS2 contain aI2 RNA derivatives in which the EBS1 and/or EBS2 sequences were replaced with those of aI1. In each case, portions of the 5' and 3' exons were also changed to aI1 sequences to permit in vitro splicing. pJVM4-aI1 EBS1 has EBS1 positions 2985–2990 changed from 5' AGAAGA to 5' CGTTGA; pJVM4-aI1EBS2 has EBS2 positions 2935–2940 changed from 5' TCATTA to 5' ACAATT; and pJVM4-aI1EBS1 EBS2 has EBS1 and EBS2 positions 2935–2940 and 2985–2990 changed from 5' TCATTA to 5' ACAATT and 5' AGAAGA to 5' CGTTGA, respectively. For pJVM4-aI1EBS1 and pJVM4-aI1EBS1/EBS2, the 5' portion of the pJVM4 insert consisting of aI1 and E2 sequence was replaced with the last 24 bp of E1. For pJVM4-aI1EBS2, positions −24 to −7 (GTCATGCTGTATTAATGA) SEQ. ID. NO. 10 were replaced with (ATGGTAATTCACAATTAT), SEQ. ID. NO. 11 leaving the aI2 IBS1 sequence unchanged. For al three constructs, the 3' portion of the insert was replaced by the first 15 bp of E2 instead of E3 and aI3.

pJVM4-EBS2-8G, pJVM4-EBS2-9T-10A, pJVM4-EBS2-11A, pJVM4-EBS2-12T, and pJVM4-EBS2-13T(1) are derivatives of pJVM4 in which the indicated changes were introduced at different positions in EBS2. pJVM4-EBS2-13T(2) is identical to pJVM4-EBS2-13T(1) except that it contains a second mutation, T to A, at intron position 2932.

pJVM4-∂-C, pJVM4-∂-G, and pJVM9-∂-T are derivatives of pJVM4 in which the a nucleotide (position 2984) was changed to C, G, or T, respectively, with the compensatory nucleotide substituted at the ∂' position of exon 3 for in vitro splicing.

Exogenous aI2 intron transcripts having a modified EBS1 sequence and/or a modified EBS2 sequence were synthesized using phage T3 polymerase and the modified plasmids as templates. The synthetic transcripts contained regions of the modified aI2 intron RNA and regions of the flanking exon 2 and exon 3 of the yeast mitochondrial COX1 protein. The synthetic transcripts were self-spliced and the spliced products desalted through a G-50 column, phenol-CIA extracted, ethanol precipitated, and dissolved in TE (pH8.0) at a final concentration of 1.0 μg/μl (0.52 μM).

The resulting modified, excised aI2 RNA molecules were individually mixed with RNA-protein complex preparations isolated from $1^o2^{\Delta D5}$ using the protocol described above in formulation 1 for RNP particle preparations. This yeast mutant has a deletion in domain V of the aI2 intron and is unable to splice aI2 RNA. This mutant overproduces aI2 protein from the unspliced precursor mRNA. Thus, the RNA-protein complex preparation contains larger amounts of the aI2 protein.

For reconstitution, 1 μl of the spliced, synthetic aI2 transcripts was mixed with 2 μl (0.025 $OD_{260}$ units) of the RNA-protein complex preparation and incubated on ice for 0–10 minutes.

Formulation 14

An RNP particle preparation containing an RNP particle in which the loop region of domain IV of the group II intron RNA is modified, that is the loop region nucleotide sequence of domain IV differs from the nucleotide sequence of the aI2 RNA of formulations 1–10 is prepared by two methods. First oligonucleotide-directed mutagenesis of the aI2 intron DNA is performed by standard, well-known methods to change the nucleotide sequences which encode for the loop region of domain IV of the aI2 intron RNA. The mutagenized aI2 intron DNA is then inserted into a vector, such as a plasmid, where it is operably linked to an RNA polymerase promoter, such as a promoter for T7 RNA polymerase or SP6 RNA polymerase or T3 RNA polymerase and an in vitro transcript of the modified group II intron RNA is made as described above in formulation 12. The exogenous RNA is then combined with an RNA-protein complex that has been isolated as described for formulation 12 to produce a modified reconstituted RNP particle preparation.

Alternatively, an RNP particle preparation in which the sequences within the loop region of the group II intron RNA are modified is prepared by site-directed mutagenesis of an organism, such as a yeast, as described in formulations 4–10, and by isolation of the RNP particle preparation from the organism as described in formulation 1. IV is performed as in formulations 4–10 of the aI2 intron DNA.

Formulation 15 RNP Particle Preparation from a Genetically-Engineered Cell

A nucleotide integrase comprising an excised RNA which is encoded by the Ll.ltrB intron of a lactococcal cojugative element pRS01 of Lactococcus lactis and the protein encoded by the ORFLtrA of the Ll.ltrB intron were prepared by transforming cells of the BLR(DE3) strain of the bacterium *Escherichia coli,* which has the recA genotype, with the plasmid pETLtrA19. Plasmid pETLtrA19 comprises the DNA sequence for the group II intron Ll.ltrB from *Lactococcus lactis,* positioned between portions of the flanking exons ltrBE1 and ltrBE2. pETLtrA19 also comprises the DNA sequence for the T7 RNA polymerase promoter and the T7 transcription terminator. The sequences are oriented in the plasmid in such a manner that the ORF sequence, SEQ. ID. NO. 6, within the Ll.ltrB intron is under the control of the T7 RNA polymerase promoter. The ORF of the Ll.ltrB intron encodes the protein ltrA. The sequence of the Ll.ltrB intron and the flanking exon sequences present in pETLtrA19 are shown SEQ.ID. NO. 5. The amino acid sequence of the ltrA protein is shown in SEQ. ID. NO.7. Domain IV is encoded by nucleotide 705 to 2572.

pETLtrA19 was prepared first by digesting pLE12, which was obtained from Dr. Gary Dunny from the University of Minnesota, with HindIII and isolating the restriction fragments on a 1% agarose gel. A 2.8 kb HindIII fragment which contains the Ll.ltrB intron together with portions of the flanking exons ltrBE1 and ltrBE2 was recovered from the agarose gel and the single-stranded overhangs were filled in with the Klenow fragment of DNA polymerase I obtained from Gibco BRL, Gaithersburg, Md. The resulting fragment was ligated into plasmid pET-11a that had been digested with XbaI and treated with Klenow fragment. pET-11a was obtained from Novagen, Madison, Wis.

pETLtrA19 was introduced into the *E. coli* cells using the conventional $CaCl_2$-mediated transformation procedure of Sambrook et al. as described in "Molecular Coning A Laboratory Manual", pages 1–82, 1989. Single transformed colonies were selected on plates containing Luria-Bertani (LB) medium supplemented with ampicillin to select the plasmid and with tetracycline to select the BLR strain. One or more colonies were inoculated into 2 ml of LB medium supplemented with ampicillin and grown overnight at 37° C. with shaking. 1 ml of this culture was inoculated into 100 ml LB medium supplemented with ampicillin and grown at 37° C. with shaking at 200 rpm until $OD_{595}$ of the culture reached 0.4. Then isopropyl-beta-D-thiogalactoside was added to the culture to a final concentration of 1 mM and incubation was continued for 3 hours. Then the entire culture was harvested by centrifugation at 2,200×g, 4° C., for 5 minutes. The bacterial pellet was washed with 150 mM NaCl and finally resuspended in ⅟₂₀ volume of the original culture in 50 mM Tris, pH 7.5, 1 mM EDTA, 1 mM DTT, and 10% (v/v) glycerol (Buffer A). Bacteria were frozen at –70° C.

To produce a lysate the bacteria were thawed and frozen at –70° C. three times. Then 4 volumes of 500 mM KCl, 50 mM $CaCl_2$, 25 mM Tris, pH 7.5, and 5 mM DTT (HKCTD) were added to the lysate and the mixture was sonicated until no longer viscous, i.e. for 5 seconds or longer. The lysate was fractionated into a soluble fraction and insoluble fraction by centrifugation at 14,000×g, 4° C., for 15 minutes. Then 5 ml of the resulting supernatant, i.e., the soluble fraction, were loaded onto a sucrose cushion of 1.85 M sucrose in HKCTD and centrifuged for 17 hours at 4° C., 50,0000 rpm in a Ti 50 rotor from Beckman. The pellet which contains the RNP particles was washed with 1 ml water and then dissolved in 25 μl 10 mM Tris, pH 8.0, 1 mM DTT on ice. Insoluble material was removed by centrifugation at 15,000×g, 4° C., for 5 minutes. The yield of RNP particles prepared according to this method comprise the excised Ll.ltrB intron RNA and the ltrA protein.

Preparation of Substrate DNA

Figure 8:
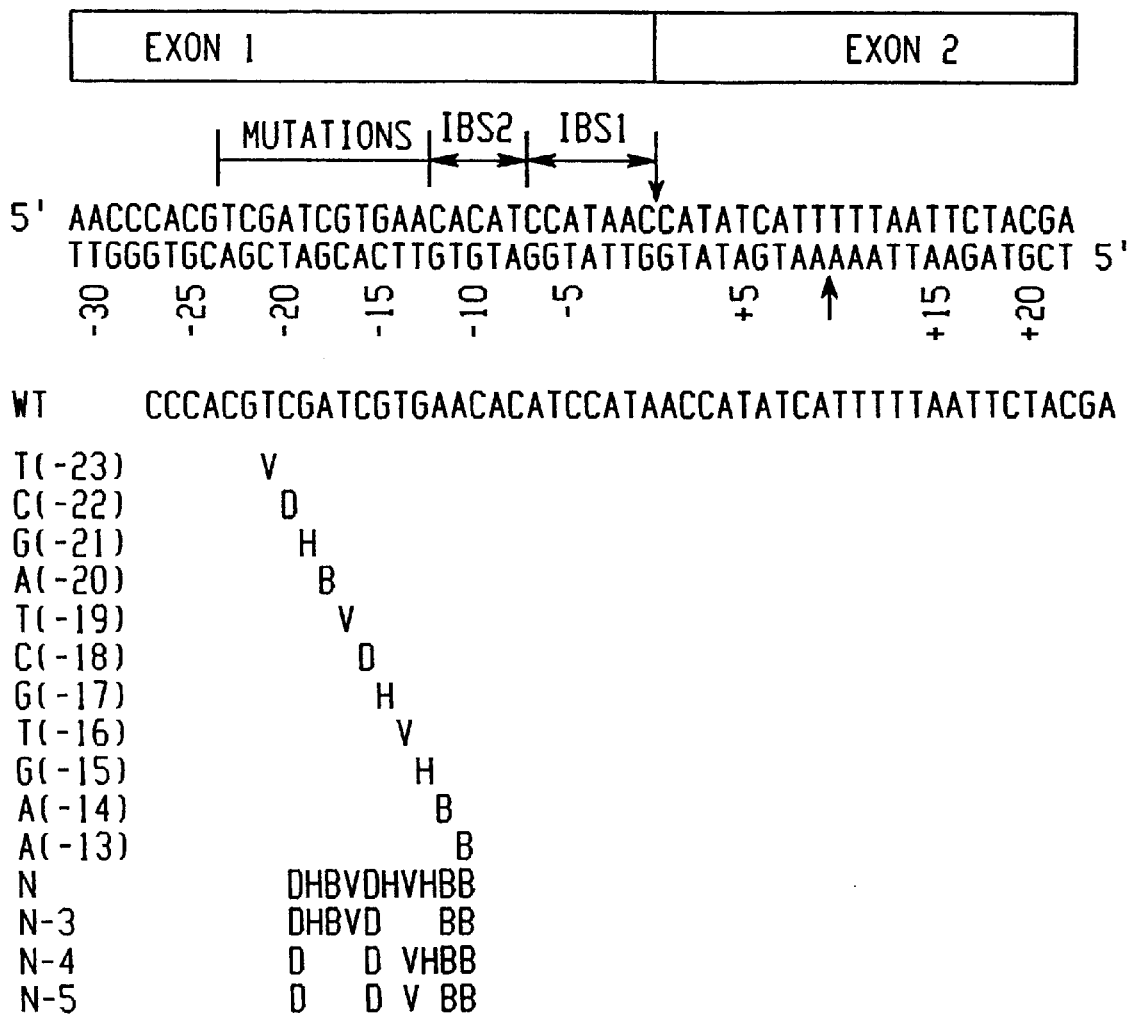
FIG. 8 is a chart depicting the wild-type sequence SEQ ID NO: 4 of the E1/E2 of the *Lactococcus lactis* ltrB gene and the position of the point mutations made in this wild-type sequence.
Figure 9:
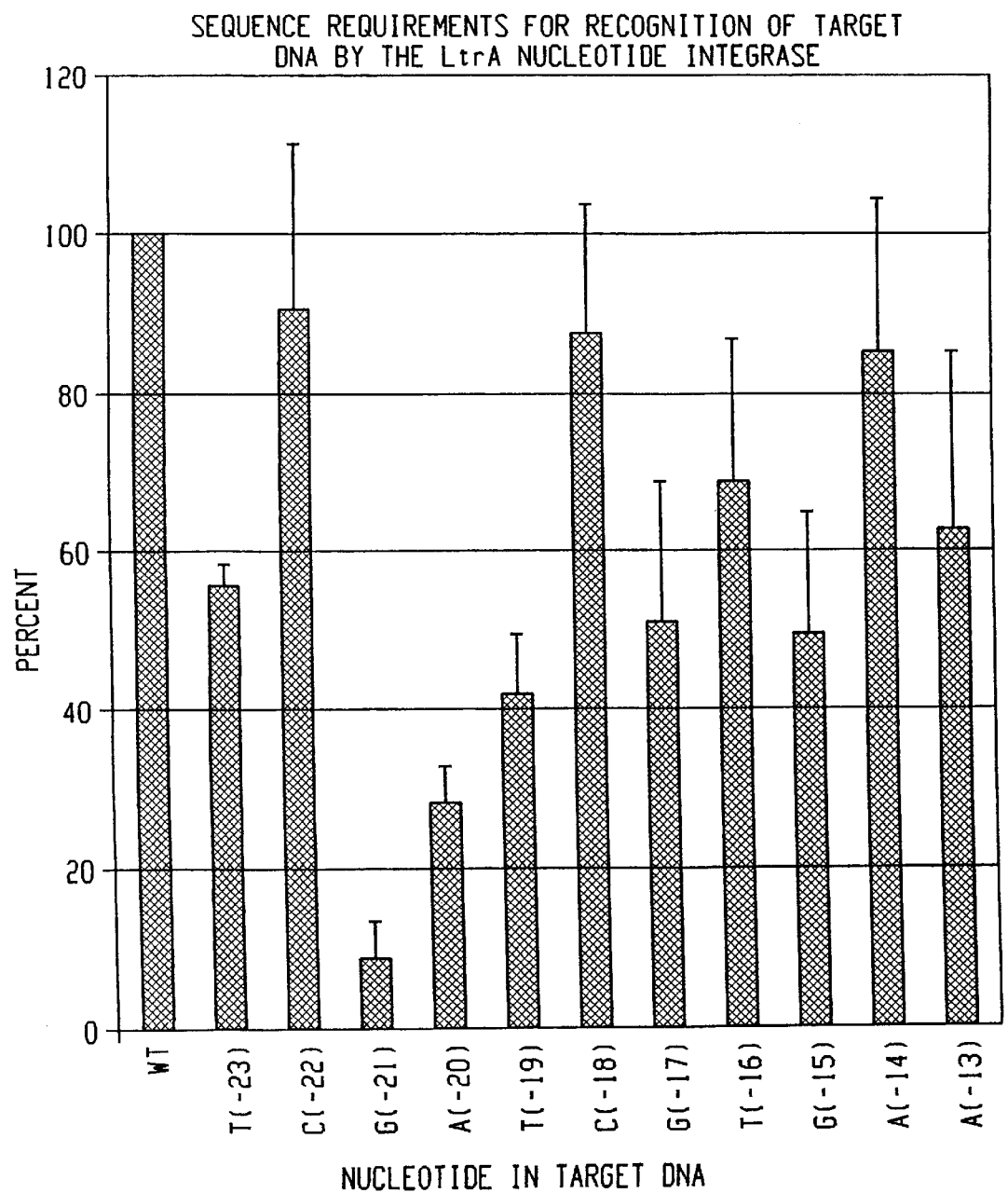
FIG. 9 is a graph showing the relative extent of cleavage of double-stranded DNA substrates by a nucleotide integrase comprising a wild-type group II intron RNA of the *Lactococcus lactis* ltrB gene, hereinafter referred to as the "Ll.ltrB intron" RNA, and the protein encoded thereby, hereinafter referred to as the ltra protein.
Figure 13:
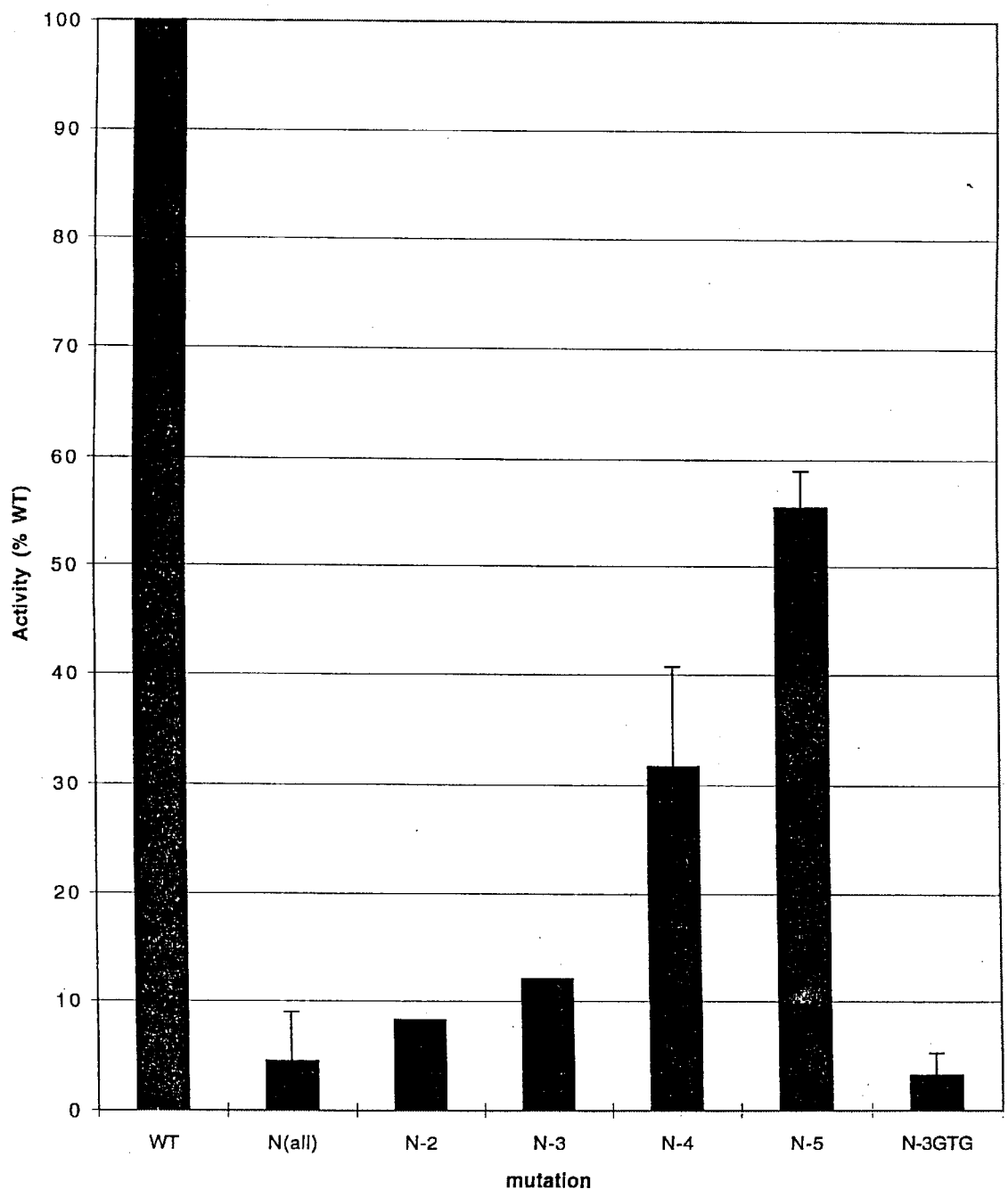
FIG. 13 is a graph showing the relative extent of cleavage of DNA substrates having multiple mutations by a nucleotide integrase comprising a wild-type Ll.ltrB intron RNA and the ltrA protein.
Figure 14:
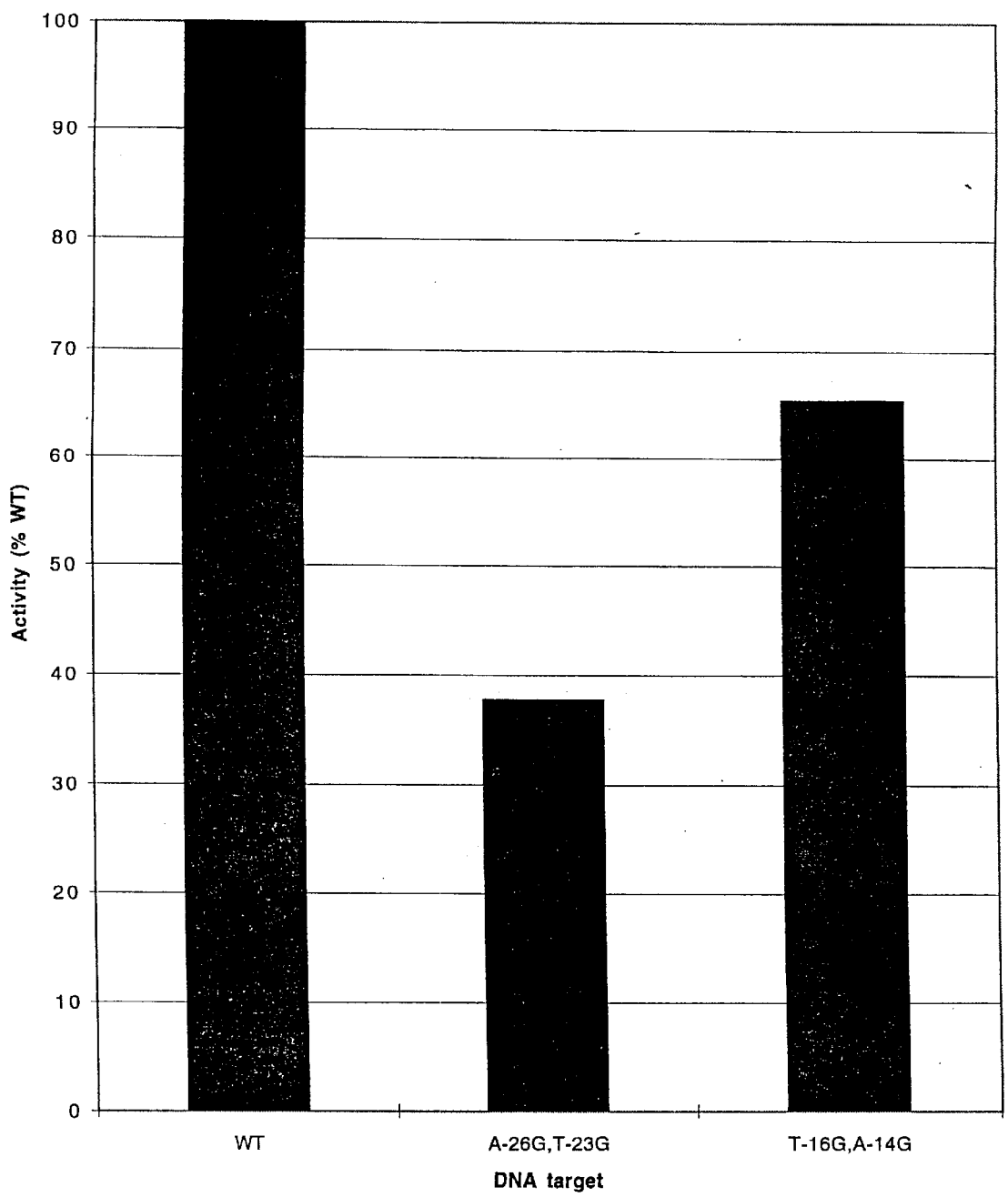
FIG. 14 is a graph showing the relative extent of cleavage of the DNA substrates having a high G/C content in the first sequence element by a nucleotide integrase comprising a wild-type Ll.ltrB intron RNA and the ltrA protein.
Figure 15:
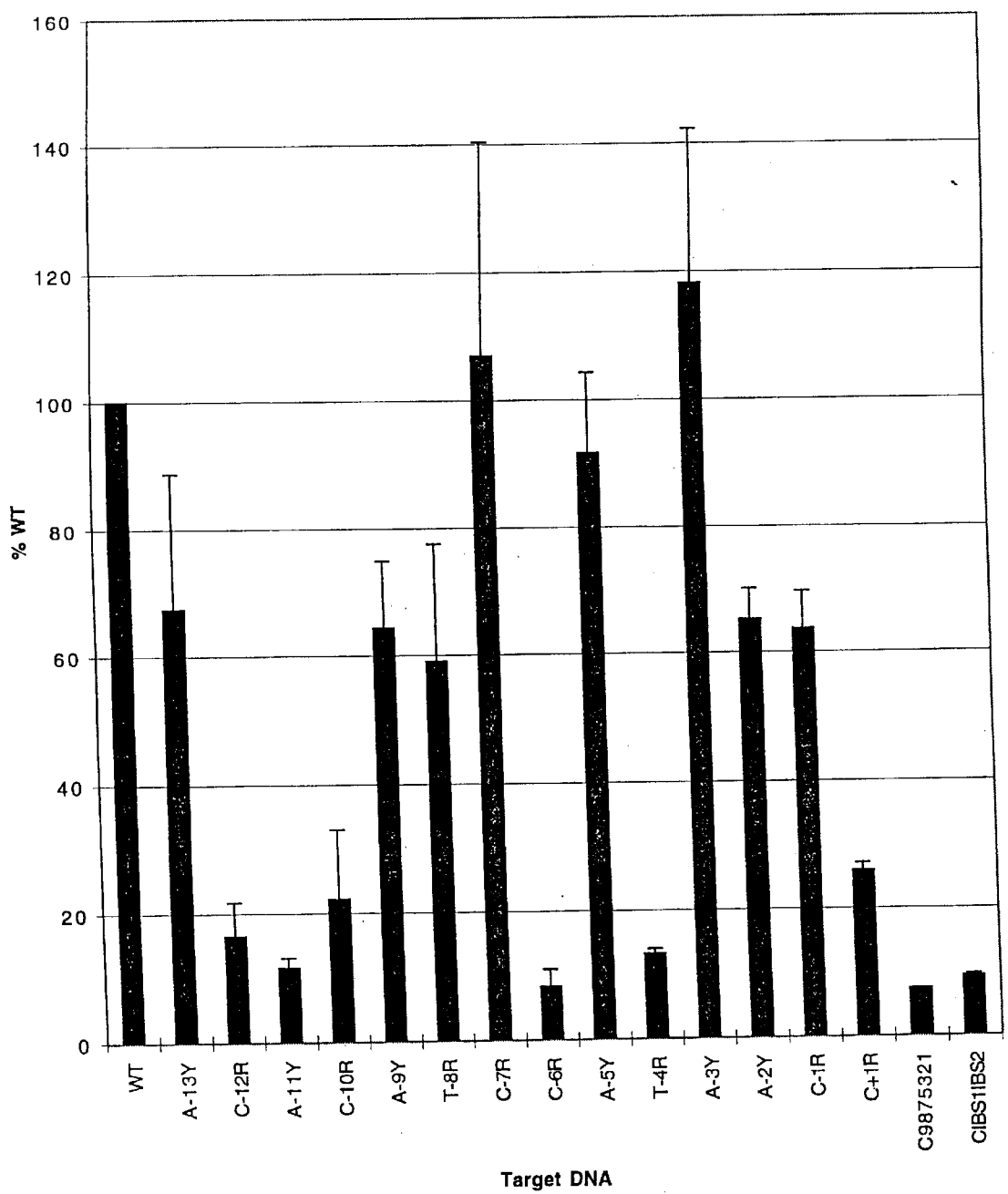
FIG. 15 is a graph showing the relative extent of cleavage of the substrates having an wild-type and mutated IBS1 and IBS2 sequences element by a nucleotide integrase comprising an Ll.ltrB intron RNA and the ltrA protein.

Labeled DNA substrates having sequences from the E2/E3 junction of the yeast mitochondrial COX1 gene, the El/E2 junction of the yeast mitochondrial COX1 gene, and the E1/E2 junction of the putative Lactococcus lactis relaxase gene (ltrB) were synthesized from recombinant plasmids or synthetic oligonucleotide templates by PCR or primer extension. The sequence of the substrate containing the E2/E3 junction of the yeast mitochondrial COX 1 gene is depicted in FIG. 3. The sequence, SEQ ID NO 2 of the top strand of such substrate is denoted as wt. The sequence of the substrate containing the E1/E2 junction of the yeast mitochondrial COX 1 gene is depicted in FIG. 6, which also identifies the locations of the mutations in this sequence. The sequence, SEQ ID NO 3 of the top strand of such substrate is denoted as wt in FIG. 6. The sequence of the substrate containing the E1 /E2 junction of the putative Lactococcus lactis relaxase gene (ltrB) is depicted in FIG. 8, which also identifies the locations of the mutations in this sequence. The sequence of the top strand of a DNA substrate containing this E1 /E2 junction is denoted as wt in FIG. 8. DNA substrates that were labeled on the 5' end of the antisense strand were also generated from plasmids by PCR with 200 ng of the 5' end-labeled primer and unlabeled primer, both of which are complementary to a sequence in the polylinker.

Single-stranded DNA substrates were synthesized by end-labeling nucleotides. Short segments of double-stranded DNA substrates were also prepared The following examples of methods employing nucleotide integrases comprising an excised aI2 intron RNA bound to an aI2 protein, an excised aI1 intron RNA bound to an aI1 protein, or an excised ltrA intron RNA bound to an ltrA protein to cleave DNA substrates are for illustration only and are not intended to limit the scope of the invention.

EXAMPLE 1

Cleaving a Double-Stranded DNA Substrate with a Nucleotide Integrase Comprising a Wild-type aI2 Intron RNA and a wild-type aI2-Encoded Protein 0.025 $O.D._{260}$ units of the RNP particles of formulation 1 were reacted with a DNA substrate consisting of yeast mitochondrial COX1 exons 2 and 3 (E2E3) and comprising the WT sequence shown in FIG. 3. The reaction was conducted at 37° C. in a buffer containing 100 mM KCl, 20 mM $MgCl_2$ at pH7.5. One portion of the cleavage products was denatured with glyoxal and analyzed in a 1% agarose gel to determine the extent of cleavage of the top strand or sense strand of the DNA substrate at the E2/E3 junction. Another portion of the nucleic acid cleavage products was analyzed in a denaturing 6% polyacrylamide gel to determine the extent of cleavage of both strands of the double stranded DNA substrate. The gels were dried and autoradiographed or quantitated by phosphorimaging with a Molecular Dynamics Phosphorimager 445.

The results indicated that the nucleotide integrase comprising an excised aI2 intron RNA from wild-type yeast bound to an aI2 intron-encoded protein from wild-type yeast cleaved the top strand of a substrate having the wt target sequence at the position marked by the arrowhead in FIG. 3. The results also indicated that the group II intron RNA is integrated into the cleavage site of the sense strand. The results also indicated that the nucleotide integrase cleaved the bottom strand or antisense strand of the double-stranded DNA substrate at a location 10 base pairs downstream from the cleavage site in the first strand. 0.025 $O.D._{260}$ units of the RNP particles of formulation 1 were reacted with six different derivatives of the wt DNA substrate of FIG. 3. Each of the derivatives contained a single point mutation in IBS2 of the wt sequence shown in FIG. 3. In the derivatives, the nucleotides in the −7, −8, −9, −10, −11, −12, and −13 were each changed to its complement. The reactions were conducted and the cleavage products assayed on a 1% agarose gel as described above. The results indicated that the ability of this nucleotide integrase to cleave a double-stranded DNA substrate was reduced unless there was full complementarity between each of the nucleotides of EBS2 of the aI2 intron RNA and each of the nucleotides of the IBS2 of the substrate. The only exception occurred with the substrate having a mutation at the nucleotide at +7.

0.025 $O.D._{260}$ units of the nucleotide integrase of formulation 1 were reacted with derivatives of the wt DNA substrate of FIG. 3 in which the nucleotides at each of the positions from −14 to −21 in the wt sequence were separately changed to a mixture of the incorrect nucleotides. Thus, the nucleotide integrase was reacted with 10 different substrates, each of which contained a mixture of three mutations at a single site. The reactions were conducted as described above in example 1 and the cleavage products were glyoxylated and assayed on a 1% agarose gel. The results indicated that the nucleotide integrase cleaved substrates having point mutations at position −21, −20, −17, and −14 in the target sequence at levels that ranged from 67% to 115% of the levels achieved when the nucleotide integrase was reacted with the wt sequence depicted in FIG. 3. The levels of cleavage were reduced to the greatest extent with the substrates having point mutations at −15 and −18. The level of cleavage that occurred with substrates having mutations at −15 and −18 was 9% and 3% of the cleavage obtained when the nucleotide integrase was reacted with the wt sequence depicted in FIG. 3. Mutations at positions −16 and −19 had moderate effects, and substrates containing these mutation were cleaved by the nucleotide integrase at levels that were 23% and 31% of the levels achieved with a substrate having the wt sequence.

0.025 $O.D._{260}$ units of the nucleotide integrase of formulation 1 were reacted with derivatives of the DNA substrate of FIG. 3 in which the nucleotides at each of the positions from +1 to +10 in the wt sequence were separately changed to a mixture of three different bases. Thus, the nucleotide integrase was reacted with 30 different substrates, each of which had a mixture of the three different nucleotides. The reactions were conducted as described above in example 1 and the cleavage products were assayed on a 6% polyacrylamide gel to determine whether the nucleotides at these positions are required for cleavage of the antisense strand of the substrate containing the wt sequence. The cleavage products were also glyoxylated and analyzed on a 1% agarose gel to determine if changes in the nucleotides at these positions had any effect on the ability of the nucleotide integrase to cleave the bottom or antisense strand of the substrate. The results indicated that the aI2 nucleotide integrase cleaved the bottom strand of substrates having changes at position +1, +4, and +6 in the wt sequence shown in FIG. 3 at levels that were 39, 33, and 29%, respectively of the levels achieved when the nucleotide integrase was reacted with the wt sequence. Changes in the nucleotides at the other positions, i.e., +2, +3, +5, +7, +8, +9, and +10 had little effect on the ability of the nucleotide sequence to cleave the bottom strand of the substrate. The results also indicated that changes in the nucleotides at each of these positions had little effect on the ability of the nucleotide integrase to cleave the top strand of the mutated substrate.

Comparative Example A 0.025 $O.D._{260}$ units of the RNP particle preparations of formulations 1, 2, 4, 5 were reacted for 20 minutes with 125 fmoles (150,000 cpm) of an internally-labeled DNA substrate having the wt sequence depicted in FIG. 3. To verify cleavage, the products were glyoxalated and analyzed in a 1% agarose gel. The results indicated that nucleotide integrases which lack excised aI2 intron RNA or in which the intron-encoded protein lacks the nonconserved portion of the Zn domain, will neither cleave the double-stranded DNA substrate nor attach an RNA.

EXAMPLE 2

Cleaving a Double-stranded DNA substrate with the Reconstituted RNP Particle Preparation of Formulation 12

The reconstituted RNP particle preparation of formulation 12 was reacted with 250 fmoles (300,000 cpm) of the 142 base pair DNA substrates generated from pE2E3 and which were 5' end-labeled on either the sense strand or the antisense strand for 20 minutes at 37° C. To verify cleavage of both strands of the substrate, the reaction products were extracted with phenol-CIA in the presence of 0.3 M NaOAc and 2 mg single-stranded salmon sperm DNA followed by precipitation with ethanol. DNA reactions products were analyzed in a 6% polyacrylamide/8 M urea gel. The reconstituted particle preparation cleaved both strands of a double-stranded DNA substrate which contained the wild-type sequence shown in FIG. 4. Similar results, i.e. cleavage of both strands, were obtained when the 5' end labeled substrates were incubated with the RNP particle preparation of formulation 10.

EXAMPLE 3

Cleaving Double-stranded DNA Substrates with a Nucleotide Integrase Comprising a Modified aI2 Intron RNA and an aI2-Encoded Protein 0.025 O.D.$_{260}$ units of the RNP particles of formulation 13 in which the EBS1 of the aI2 group II intron RNA was changed to the EBS1 sequence of the aI1 intron RNA was reacted with the wt DNA substrate of FIG. 3 and with a derivative thereof in which the nucleotides at position −1 to −6 were changed to 5' TTAATG, which is the IBS1 sequence of the wt sequence for the aI1 nucleotide integrase. Each of the derivatives contained a single mutation in the wt sequence shown in FIG. 3. The reactions were conducted and the cleavage products analyzed as described in example 1. The aI2 nucleotide integrase comprising a group II intron RNA with a modified EBS1 was not able to cleave a substrate with the wt sequence but was able to cleave a substrate in which the nucleotides at position −1 to −6 were complementary to the modified EBS I1.

EXAMPLE 4

Cleaving Substrate with a Nucleotide Integrase Comprising a Wild-type or Modified aI2 Intron RNA and an aI2-Encoded Protein 0.025 O.D.$_{260}$ units of the RNP particles of formulation 1 were reacted with three different derivatives of the DNA wt substrate of FIG. 3. Each of the derivatives contained a single point mutation. In the derivatives the nucleotide at +1 was changed to either a C, G, or A. The derivatives were also reacted with a nucleotide integrase comprising an aI2 intron RNA in which the nucleotide immediately preceding EBS1 was either an A, G, C, or T. The reactions were conducted and the cleavage products assayed on a 1% agarose gel as described in example 1. The results indicated that cleavage of the top strand is enhanced when the nucleotide at +1 is complementary to the nucleotide immediately preceding the EBS1 in the aI2 intron RNA and that cleavage of the sense strand is strongly reduced when the target sequence has a G at the +1 position.

EXAMPLE 5

Cleaving Double-Stranded DNA Substrates with a Nucleotide Integrase Comprising an aI1 Intron RNA and an aI1 Intron-encoded Protein Double-stranded DNA substrates comprising either the wt sequence or an altered sequence having one of the eleven single point mutations depicted in FIG. 6 were reacted with the RNP particle preparation of Formulation 3. For each reaction, 1.5 nM (about 150000 cpm) of a double-stranded DNA substrate was mixed with 0.025 OD$_{260}$ units of the RNP particle preparation in 10 μl of 50 mM Tris pH 7.5, 5 mM KCl, 10 mM MgCl$_2$, 5mM DTT. The reaction mixtures were incubated for 20 minutes at 37° C. The reaction was stopped by adding 70 μl of 0.5 mM EDTA, 0.15 mg/ml tRNA. The nucleic acids were phenol extracted, ethanol precipitated, glyoxylated and analyzed on a 1% agarose gel.

The nucleotide integrase of formulation 3 cleaved substrate DNAs having mutations at positions −23, −20, −17, −16, −15 and −14 as efficiently as a substrate having the wt sequence depicted in FIG. 6. Mutations at positions G(−22), G(−21), A(−19) and A(−18) reduced the efficiency of the cleavage somewhat from 75 to 25% of the cleavage that occurred with the wt sequence. The most critical nucleotide appears to be the C at position(−13). Mutations at this position reduced cleavage of the substrate to less than 1% of that which occurred with the wt sequence.

Mutations in the downstream region +1 to +10 had variable effects on cleavage of the top strand. Substitution of the nucleotide at +1 which disrupts the δ interaction strongly inhibited cleavage. The substitution at +2 inhibited cleavage of the top strand by about 50%, whereas other substitutions had relatively little effect.

The ability of the nucleotide integrase of formulation 3 to cleave the other or the bottom strand of substrates was also determined. Substitutions at positions −13, −18, −19, and −21 reduced cleavage of both the bottom strand and the top strand of the double-stranded substrate. In the downstream region, nucleotide substitutions at +4 and +6 strongly inhibited cleavage of the bottom strand. (9 and 1% activity, respectively). Nucleotide substitutions at +7 and +9 inhibited moderately (53% and 18% activity, respectively), while nucleotide substitutions at +2, +3, +5, and +10 reproducibly stimulated cleavage of the bottom strand.

EXAMPLE 6

Cleaving Substrates with a Nucleotide Integrase Comprising a Wild-type or Modified L1.ltrB Intron RNA and an ltrA Protein Double-stranded DNA substrates comprising either the wt sequence or an altered wt sequence having one of the eleven single point mutations depicted in FIG. 8 were reacted with the RNP particle preparation of Formulation 15. The point mutations occur at positions −23 to −13 in the wt sequence. For each reaction, 1.5 nM of a double-stranded DNA substrate was mixed with 0.025 OD$_{260}$ units of the RNP particle preparation in 10 μl of 50 mM Tris pH 7.5, 10 mM KCl, 10 mM MgCl$_2$, 5mM DTT. The reaction mixtures were incubated for 20 minutes at 37° C. The reaction was stopped by adding 70 ml of 28.6 mM EDTA, 0.15 mg/ml tRNA. The nucleic acids were phenol extracted, ethanol precipitated, glyoxylated and analyzed on a 1% agarose gel The nucleotide integrase of formulation 15 cleaved substrate DNAs having mutations at positions C(−22), C(−1 8), and A(−14) at levels that were approximately 80% of the levels achieved with a substrate having the wt sequence depicted in FIG. 8. Substrates having point mutations at positions G(−21), A(−20), T(−19) were cleaved at levels that were approximately 40% or less of the levels achieved using substrates having a wt sequence.

The nucleotide integrase of formulation 15 was also reacted with double stranded DNA substrates in which the IBS1 and IBS2 sequences were modified as shown in FIG. 12. First, a DNA substrate in which both the IBS1 sequence (−1 to −7) and the IBS2 sequence (−8 to −13) were changed to their complementary sequence (cIBS1IBS2) gave less than 10% of the activity of the wild-type substrate. Next, each position in the IBS1 sequence and the IBS2 sequence as well as the δ nucleotide (−13 to +1) were modified by changing A or G residues to a mixture of pyrimidine residues, and C or T residues to a mixture of purine residues. Substrates having substitutions at positions −12, −11, −10, −6, −4, and +1 were cleaved by the wild-type ltrA nucleotide integrase at levels that were 10 to 30% of the levels achieved when the substrate contained the wild-type sequence shown in FIG. 12. The ltrA nucleotide integrase cleaved substrates having substitutions at position −13, −9, −8, −2, and −1 at levels that were about 60% of the wild-type activity. Substitutions at −7, −5, and −3 in the substrate sequence had little to no effect on the ability of the ltrA nucleotide integrase to cleave the top strand of the substrate (92 to 118% of wild-type activity). Further, a DNA substrate in which position −7, −5, and −3 were changed simultaneously gave about 70% of wild-type activity, consistent with the relatively small effects of single nucleotide substitutions at these positions. The results indicate that base pairing between the nucleotides in the EBS1 sequence of the Ll.ltrB intron RNA and the nucleotides at positions −3, −5, and −7 is not required for cleavage of the top strand of a double-stranded DNA substrate by the ltrA nucleotide integrase.

The ltrA nucleotide integrase comprising a wild-type Ll.ltrB intron RNA and an ltrA protein was also reacted with double stranded DNA substrates in which the nucleotides at positions +2 to +19, +21, to +24, +30 and +32 of the wild-type sequence shown in FIG. 12 were simultaneously changed to their respective complement. The ltrA integrase cleaved substrates having multiple substitutions in these downstream nucleotides at levels that were 70% of those achieved with the wild-type substrate.

An ltrA nucleotide integrase comprising a wild-type Ll.l-trB intron RNA and an ltrA protein was also reacted with a double stranded DNA substrate in which the A-T base-pairs at positions −26 and −23 of the wild-type sequence shown in FIG. 12 were changed to G-C base-pairs, and with a double-stranded DNA substrate in which the A-T base-pairs at positions −16 and −14 were changed to G-C base pairs. The wild-type ltrA nucleotide integrase cleaved the modified substrates at levels that were about 35% and 65%, respectively of the levels achieved with the wild-type substrate. Thus, except for those nucleotide pairs that are at critical positions in the first sequence element (such as for example the G-C pair at position −21), it is preferred that the first sequence element be A-T rich and G-C poor.

An ltrA nucleotide integrase comprising a wild-type Ll.l-trB intron RNA and an ltrA protein was also reacted with double stranded DNA substrates in which the sequence of nucleotides at positions +2 to +5 of the wild-type sequence shown in FIG. 12 was changed to the more G/C rich sequence TGCG. The wild-type ltrA nucleotide integrase cleaved the modified substrates at levels that were less than 10% of the levels achieved with the wild-type substrate. Thus, it is preferred that the second sequence element, particularly the first five pairs of nucleotides downstream of the cleavage site, be A-T rich or G-C poor.

LtrA nucleotide integrases containing a modified Ll.ltrB intron RNA and an ltrA protein were reconstituted by using purified LtrA protein and in vitro synthesized intron RNA. The modifications were made in the EBS1 nucleotide that binds to the nucleotide at position −4 in the substrate and in the nucleotides of the EBS2 sequence that bind to the nucleotides at positions −10, 11, and −12 in the substrate. Modifications were also made in the 5 nucleotide. Cleavage of the top strand of substrates in which the nucleotides at positions −10, −11 and +1 were changed from wild-type was restored by compensatory mutations in the corresponding EBS2 positions and the δ nucleotide of the intron RNA. A compensatory change in the EBS2 nucleotide that binds to the nucleotide at −12 in the substrate partially restored the cleavage activity of the nucleotide integrase, while a nucleotide integrase comprising a compensatory change in the EBS1 nucleotide that binds to the nucleotide at −4 in the substrate exhibited no detectable cleavage activity. Thus, it is preferred that the ltrA nucleotide integrase be used to cleave double-stranded DNA substrates that have a T at position −4 relative to the cleavage site.

EXAMPLE 7

Cleaving a Double-Stranded DNA Substrate with Purified RNP Particles 125 fmoles (150,000 cpm) of an internally-labeled substrate containing of yeast mitochondrial COX1 exons 2 and 3 (E2E3) and comprising the WT sequence shown in FIG. 3 were incubated with 10 μl of each of the fractions obtained from the sucrose gradient in formulation 1a. Taking into account the composition of the fractions, the final reaction medium of 20 μl contained 100 mM KCl, 20 mM $MgCl_2$, 50 mM Tris-HCl, pH 7.5, and 5 mM DTT. Following a 20 minute reaction at 37° C., 30 μl of water, 5 μl 0.3 M NaOAc and 5 μg tRNA were added to the fractions. The reaction products were phenol extracted, ethanol precipitated, glyoxalated, separated on a 1% agarose gel and analyzed by autoradiography of the dried gel. The results indicated that the purified RNP particles of formulation 1a are useful to cleave both strands of a double-stranded DNA substrate and to insert the aI2 intron RNA into the cleavage site.

EXAMPLE 8

Cleaving Both Strands of a Double-stranded DNA Substrate and Attaching a cDNA to the Cleavage Site of the Bottom Strand.

0.025 $O.D._{260}$ units of the RNP particles from formulations 1,2,4,5,6,7,8,9, were incubated with 250 fmoles (300,000 cpm) of a 142 base pair DNA substrate comprising the WT sequence shown in FIG. 3. DNA incubation products were analyzed in a 6% polyacrylamide/8 M urea gel.

A radiolabeled band corresponding to the 5' fragment was detected when RNP particles of formulations 1 and 2 were incubated with substrates that had been labeled on the 5' end of either the top strand or the bottom strand of the DNA substrate, indicating that these particles cleaved both strands of the DNA substrate. The RNP particles of formulation 1 cleaved the top strand precisely at the exon 2-exon 3 junction. The RNP particles of formulations 1 and 2 cleaved the bottom or antisense strand 10 base pairs downstream from the top or sense strand cleavage site. RNP particles of formulation 1 that had been treated with protease K, or RNase A, or boiled did not cleave either strand.

Radiolabeled bands were also detected when the RNP particles of formulation 4 were incubated with DNA substrates that had been 5' end-labeled on either the sense strand or antisense strand, indicating that this nucleotide integrase cleaved both strands of DNA substrate. The RNP particles of formulation 4 contain a modified, excised aI2 RNA and an aI2-encoded protein which lacks detectable reverse transcriptase activity. Although the extent of cleavage of RNP particles of formulation 4 is somewhat reduced compared to cleavage with the RNP particle preparation of formulation 1, the endonuclease activity of the RNA is present even when the reverse transcriptase activity of the aI2-encoded protein is absent.

The radiolabeled bands were detected when the RNP particles of formulation 5 were incubated with the DNA substrate that had been labeled on the 5' end of either the top or bottom strand. In quantitative assays normalized by either O.D.$_{260}$ or soluble aI2 reverse transcriptase activity, the cleavage activities for the top and bottom strands by the RNP particles of formulation 5 were 6% and 25%, respectively, of activities of the RNP particles of formulation 1.

A radiolabeled band corresponding to the 5' fragment was detected when the DNA substrate labeled on the 5' end of the top strand was incubated with the RNP particles of formulation 6, but a band corresponding to the 5' fragment of the top strand was not detected when the RNP particles of formulation 6 were incubated with a DNA substrate that had been labeled on the 5' end of the bottom strand. The RNP particles of formulation 6 contain a modified, excised aI2 intron RNA and an aI2-encoded protein that has an alteration in one of the putative endonuclease motifs. Similar results were obtained with the RNP particles of formulation 7, which contains a modified, excised aI2 intron RNA and an aI2-encoded protein in which the conserved portion of the Zn domain is absent. Likewise, RNP particles of formulations 8 and 9, each of which contains a modified, excised aI2 intron RNA and an aI2-encoded protein in which there is a mutation in the $Zn^{2+}$-like motif, cleaved the sense strand but not the antisense strand of the DNA substrate. For the RNP particles of formulations 6, 7, 8, and 9, the level of sense-strand cleavage was proportional to the amount of RNA-DNA products detected in the agarose gels. These findings indicate that the antisense strand endonuclease activity of the aI2-encoded protein is associated with the Zn domain.

A radiolabeled band corresponding to the 5' fragment was detected when the reconstituted RNP particle preparation of formulation 12 was incubated with substrates that had been labeled on the 5' end of either the sense strand or the antisense strand of the DNA substrate. These results establish that the reconstituted RNP particle preparation cleaves both strands of the DNA substrate.

Thus, both the catalytic RNA molecule of the nucleotide integrase and the intron-encoded protein are required for cleavage of both strands of the double stranded DNA. Certain modifications in the Zn domain and the X domain of intron-encoded protein disrupt the cleavage of the antisense strand of the nucleotide integrase 0.025 O.D.$_{260}$ units of the RNP particle preparations of formulations 1, 2, 4 and 5 were combined in 10 μl of reaction medium with 1 μg of plasmid containing the wild-type sequence depicted in FIG. 4. The reaction medium contained 0.2 mM each of dATP, dGTP and dTTP, 10 μCi [a-$^{32}$P]-dCTP (3,000 Ci/mmole; DuPont NEN, Boston, Mass.), 100 mM KCl, and 5 mM dithiothreitol, 2 mM $MgCl_2$, and 50 mM Tris-HCl, pH 8.5. The reaction was initiated by addition of the RNP preparations, incubated for 10 minutes at 37° C., and chased with 0.2 mM dCTP for another 10 minutes. After the chase period, the reactions were terminated by extraction with phenol-CIA (phenol-chloroform-isoamyl alcohol; 25:24:1) in the presence of 0.3 M sodium acetate, pH 7.8, and 5 μg E. coli tRNA carrier (Sigma, St. Louis, Mo.). Products were ethanol precipitated twice and resolved in 1% agarose gels containing 90 mM Tris-borate, pH 8.3, 2 mM EDTA and 0.05% ethidium bromide. The results indicated that the RNP particles of formulations 1 and 2 catalyze the formation of a DNA molecule on the cleaved DNA substrate. The results also indicated that a nucleotide integrase which lacks an excised group II intron RNA or which contains a group II intron-encoded protein that lacks a reverse transcriptase domain does not catalyze the formation of a cDNA molecule on the cleaved strand.

Cleavage of Single Stranded DNA

An aI2 nucleotide integrase comprising an excised aI2 RNA and aI2-encoded protein was used to cleave a single stranded DNA comprising an IBS2 and IBS1 sequence complementary to the EBS1 and EBS2 sequences of the wild-type aI2 intron RNA. The reaction is greatly improved when the 3 nucleotides +1 to +3 can base-pair with the 3 nucleotides immediately upstream of EBS1. The most preferred reaction conditions for cleavage of the substrate and insertion of the intron RNA into the cleavage site by the nucleotide integrase, are 100 mM KCl, 20 mM $MgCl_2$, pH 7.5, 5 mM DTT and 37° C.

What is claimed is:

1. A method of cleaving a double stranded DNA substrate at a cleavage site comprising the following steps:
   (a) providing a double-stranded DNA substrate having a top strand and a recognition site; wherein said top strand has a T at position −4 relative to the cleavage site;
   (b) providing an isolated nucleotide integrase comprising
      (i) a wild-type or a modified Ll.ltrB intron RNA having a first hybridization sequence for hybridizing with a first intron RNA binding sequence on said top strand of the DNA substrate and a second hybridization sequence for hybridizing with a second RNA binding sequence on said top strand of the substrate; and
      (ii) a protein encoded by an Ll.ltrB intron for binding with at least one nucleotide in a first sequence element in the recognition site of the substrate, said protein being bound to said Ll.ltrB intron RNA; and
   (c) reacting the nucleotide integrase with the substrate to permit the nucleotide integrase to cleave said top strand of the DNA substrate and to insert the Ll.ltrB intron RNA into the cleavage site.

2. The method of claim 1 wherein the top strand of the substrate further has a G at −21 and an A at −20 relative to the cleavage site and wherein the top strand of the substrate has a sequence which differs from the wt sequence, SEQ. ID. NO: 4, shown in FIG. 8.

3. The method of claim 2 wherein the top strand of the substrate further has a T at −19, a G at −17, and a G at −15 relative to the cleavage site.

4. The method of claim 2 wherein the nucleotide at −3, or −5, or −7 on the top strand of the substrate is not complementary to a nucleotide at the corresponding position in the first hybridization sequence of the Ll.ltrB intron RNA.

5. The method of claim 1 wherein the sequence of nucleotides from +1 through +5 on the top strand of the substrate contains more A and T nucleotides than C and G nucleotides.

6. The method of claim 1 wherein the sequence of nucleotides from −14 to −26 on the top strand of the substrate contains more A and T nucleotides than C and G nucleotides.

7. The method of claim 1 wherein the top strand of the substrate further has a C at −12, an A at −11, a C at −10, a C at −6, and a C at +1 relative to the cleavage site and wherein the top strand of the substrate has a sequence which differs from the wt sequence, SEQ. ID. NO: 4, shown in FIG. 8.

8. The method of claim 1 wherein the top strand of the substrate has a nucleotide that is complementary to the nucleotide on said top strand of the substrate, said nucleotide being located at position +1 relative to the cleavage site and wherein the top strand of the substrate has a sequence which differs from the wt sequence, SEQ. ID. NO: 4, shown in FIG. 8.

9. The method of claim 1 wherein there is at least 80% complementarity between the first hybridization sequence and the first intron RNA binding sequence and at least 80% complementarity between the second hybridization sequence and the second intron RNA-binding sequence and wherein the top strand of the substrate has a sequence which differs from the wt sequence, SEQ. ID. NO: 4, shown in FIG. 8.

10. A method for cleaving a single-stranded nucleic acid substrate at a cleavage site comprising the following steps:
  (a) providing an isolated nucleotide integrase comprising:
    (i) a group II intron RNA having a first hybridizing sequence for hybridizing with a first intron RNA binding sequence on the nucleic acid substrate and a second hybridizing sequence for hybridizing with a second hybridizing sequence on said nucleic acid substrate, wherein the three nucleotides immediately upstream of the first hybridizing sequence are complementary to nucleotides at positions +1 to +3 on the substrate, and
    (ii) a group II intron-encoded protein bound to said group II intron RNA; and
  (b) reacting the nucleotide integrase with the substrate to permit the nucleotide integrase to cleave the nucleic acid substrate and to insert the group II intron RNA into the cleavage site.

* * * * *

UNITED STATES PATENT AND TRADEMARK OFFICE
CERTIFICATE OF CORRECTION

PATENT NO.    : 6,306,596 B1
DATED         : October 23, 2001
INVENTOR(S)   : Alan M. Lambowitz, Steven Zimmerly, Huatao Guo, Georg Mohr and Clifford James Beall It is certified that error appears in the above-identified patent and that said Letters Patent is hereby corrected as shown below:

<u>Title page,</u>
After "[75] Inventors:" please delete "Allen" and insert -- Alan --.

Signed and Sealed this

Twenty-eighth Day of May, 2002

Attest:

*Attesting Officer*

JAMES E. ROGAN
*Director of the United States Patent and Trademark Office*

SEQUENCE LISTING

<160> NUMBER OF SEQ ID NOS: 12

<210> SEQ ID NO 1
<211> LENGTH: 5203
<212> TYPE: DNA
<213> ORGANISM: S. cerevisiae

<400> SEQUENCE: 1

```
atggtacaaa gatgattata ttcaacaaat gcaaaagata ttgcagtatt atattttatg      60
ttagctattt ttagtggtat ggcaggaaca gcaatgtctt taatcattag attagaatta     120
gctgcacctg gttcacaata tttacatggt aattcacagt tatttaatgg tgcgcctctc     180
agtgcgtata tttcgttgat gcgtctagca ttagtattat gaatcatcaa tagatactta     240
aaacatatga ctaactcagt aggggctaac tttacgggga caatagcatg tcataaaaca     300
cctatgatta gtgtaggtgc agttaagtgt tacatggtta ggttaacgaa cttcttacaa     360
gtctttatca ggattacaat ttcctcttat catttggata tagtaaaaca agtttgatta     420
ttttacgttg aggtaatcag attatgattc attgttttag atagcacagg cagtgtgaaa     480
```

-continued

```
aagatgaagg acctaaataa cacaaaagga aatacgaaaa gtgagggatc aactgaaaga    540
ggaaactctt gagttgacag aggtatagta gtaccgaata ctcaaataaa aatgagattt    600
ttaaatcaag ttagatacta ttcagtaaat aataatttaa aaatagggaa ggataccaat    660
attgagttat caaaagatac aagtacttcg gacttgttag aatttgagaa attagtaata    720
gataatataa atgaggaaaa tataaataat aatttattaa gtattataaa aaacgtagat    780
atattaatat tagcatataa tagaattaag agtaaacctg gtaatataac tccaggtaca    840
acattagaaa cattagatgg tataaatata atatatttaa ataaattatc aaatgaatta    900
ggaacaggta aattcaaatt taaacccatg agaatagtta atattcctaa acctaaagct    960
ggtataagac ctttaagtgt aggtaatcca agagataaaa ttgtacaaga agttataaga    1020
ataattttag atacaatttt tgataaaaag atatcaacac attcacatgg ttttagaaag    1080
aatataagtt gtcaaacagc aatttgagaa gttagaaata tatttggtgg aagtaattga    1140
tttattgaag tagacttaaa aaaatgtttt gatacaattt ctcatgattt aattattaaa    1200
gaattaaaaa gatatatttc agataaaggt tttattgatt tagtatataa attattaaga    1260
gctggttata ttgatgagaa aggaacttat cataaaccta tattaggttt acctcaagga    1320
tcattaatta gtcctatctt atgtaatatt gtaataacat tggtagataa ttgattagaa    1380
gattatatta atttatataa taaaggtaaa gttaaaaaac aacatcctac atataaaaaa    1440
ttatcaagaa taattgcaaa agctaaaata ttttcgacaa gattaaaatt acataaagaa    1500
agagctaaag gcccactatt tatttataat gatcctaatt tcaagagaat aaaatacgtt    1560
agatatgcag atgatatttt aattgggta ttaggttcaa aaaatgattg taaaataatc    1620
aaaagagatt taaacaattt tttaaattca ttaggtttaa ctataaatga agaaaaaact    1680
ttaattactt gtgcaactga actaccagca agattttag gttataatat ttcaattaca    1740
cctttaaaaa gaatacctac agttactaaa ctaattagag gtaaacttat tagaagtaga    1800
aatacaacta gacctattat taatgcacca attagagata ttatcaataa attagctact    1860
aatggatatt gtaagcataa taaaaatggt agaaataggt gcctacaag agtaggtaga    1920 tgactatatg aagaacctag aacaattatt aataattata aagcgttagg tagaggtatc    1980
ttaaattatt ataaattagc tactaattat aaaagattaa gagaaagaat ctattacgta    2040
ttatattatt catgtgtatt aactttagct agtaaatata gattaaaaac attaagtaaa    2100
actattaaaa aatttggtta taattttaaat attattgaaa atgataaatt aattgccaat    2160
tttccaagaa atacttttga taatatcaaa aaaattgaaa atcatggtat atttatatat    2220
atatcagaag ctaaagtaac tgatccttt gaatatatcg attcaattaa atatatatta    2280
cctacagcta aagctaattt taataaaacct tgtagtattt gtaattcaac tattgatgta    2340
gaaatacatc atgttaaaca attacataga ggtatattaa aagcacttaa agattatatt    2400
ctaggtagaa taattaccat aaacagaaaa caaattccat tatgtaaaca atgtcatatt    2460
aaaacacata aaaataaatt taaaatatat gcacctggta tataaaatct attattaatg    2520
atactcaata tggaaagccg tatgatggga aactatcacg tacggtttgg gaaaggctct    2580
ttaacacgtg gcaacatagg ttaatttgct attcatttt tagtagttgg tcatgctgta    2640
ttaatgattt tctgtgcgcc gtttcgctta atttatcact gtattgaagt gttaattgat    2700
aaacatatct ctgtttattc aattaatgaa aactttaccg tatcattttg gttctgatta    2760
ttagtagtaa catacatagt atttagatac gtaaaccata tggcttaccc agttggggcc    2820
aactcaacgg ggacaatagc atgccataaa agcgctggag taaaacagcc agcgcaaggt    2880
```

```
aagaactgtc cgatggctag gttaacgaat tcctgtaaag aatgtttagg gttctcatta  2940
actccttccc acttgggat tgtgattcat gcttatgtat tggaagaaga ggtacacgag  3000
ttaaccaaaa atgaatcatt agctttaagt aaaagttgac atttggaggg ctgtacgagt  3060
tcaaatggaa aattaagaaa tacgggattg tccgaaaggg gaaaccctgs ggataacgga  3120
gtcttcatag tacccaaatt taatttaaat aaagcgagat actttagtac tttatctaaa  3180
ttaaatgcaa ggaaggaaga cagtttagcg tatttaacaa agattaatac tacggatttt  3240
tccgagttaa ataaattaat agaaaataat cataataaac ttgaaaccat taatactaga  3300
attttaaaat taatgtcaga tattagaatg ttattaattg cttataataa aattaaaagt  3360
aagaaaggta atatatctaa aggttctaat aatattacct tagatgggat taatatttca  3420
tatttaaata aattatctaa agatattaac actaataygt ttaaattttc tccggttaga  3480
agagttgaaa ttcctaaaac atctggagga tttagacctt taagtgttgg aaatcctaga  3540
gaaaaaattg tacaagaaag tatgagaata atattagaaa ttatctataa taatagtttc  3600
tcttattatt ctcatggatt tagacctaac ttatcttgtt taacagctat tattcaatgt  3660
aaaaattata tgcaatactg taattgattt attaaagtag atttaaataa atgctttgat  3720
acaattccac ataatatgtt aattaatgta ttaaatgaga gaatcaaaga taaaggtttc  3780
atagacttat tatataaatt attaagagct ggatatgttg ataaaaataa taattatcat  3840
aatacaactt taggaattcc tcaaggtagt gttgtcagtc ctattttatg taatattttt  3900
ttagataaat tagataaata tttagaaaat aaatttgaga atgaattcaa tactggaaat  3960
atgtctaata gaggtagaaa tccaatttat aatagtttat catctaaaat ttatagatgt  4020
aaattattat ctgaaaaatt aaaattgatt agattaagag accattacca aagaaatatg  4080
ggatctgata aaagttttaa aagagcttat tttgttagat atgctgatga tattatcatt  4140
ggtgtaatgg gttctcataa tgattgtaaa aatattttaa acgatattaa taacttctta  4200
aaagaaaatt taggtatgtc aattaatata gataaatccg ttattaaaca ttctaaagaa  4260
ggagttagtt ttttagggta tgatgtaaaa gttacacctt gagaaaaaag accttataga  4320
atgattaaaa aaggtgataa ttttattagg gttagacatc atactagttt agttgttaat  4380 gccccatta gaagtattgt aataaaatta ataaacatg gctattgttc tcatggtatt  4440
ttaggaaaac ccagagggt tggaagatta attcatgaag aaatgaaaac catttaatg  4500 cattacttag ctgttggtag aggtattata aactattata gattagctac caattttacc  4560
acattaagag gtagaattac atacatttta ttttattcat gttgtttaac attagcaaga  4620
aaatttaaat taaatactgt taagaaagtt atttaaaat tcggtaaagt attagttgat  4680
cctcattcaa aagttagttt tagtattgat gattttaaaa ttagacataa aataaatata  4740
actgattcta attatacacc tgatgaaatt ttagatagat ataaatatat gttacctaga  4800
tctttatcat tatttagtgg tatttgtcaa atttgtggtt ctaaacatga tttagaagta  4860
catcacgtaa gaacattaaa taatgctgcc aataaaatta aagatgatta tttattaggt  4920
agaatgatta agataaatag aaaacaaatt actatctgta aaacatgtca ttttaaagtt  4980
catcaaggta aatataatgg tccaggttta taataattat tatactcctt cgggtcgcc  5040 gcggggcgg gccggactat taaatatgcg ttaaatggag agccgtatga tatgaaagta  5100
tcacgtacgg ttcggagagg gctctttat atgaatgtta ttcattcag ataggtttgc  5160 tactctactc ttagtaatgc ctgctttaat tggaggtttt ggt                    5203
```

<210> SEQ ID NO 2
<211> LENGTH: 53
<212> TYPE: DNA
<213> ORGANISM: S. cerevisiae

<400> SEQUENCE: 2
gtagttggtc atgctgtatt aatgattttc ttcttagtaa tgcctgcttt aat    53

<210> SEQ ID NO 3
<211> LENGTH: 53
<212> TYPE: DNA
<213> ORGANISM: S. cerevisiae

<400> SEQUENCE: 3
aatttacatg gtaattcaca gttatttaat gttttagtag ttggtcatgc tgt    53

<210> SEQ ID NO 4
<211> LENGTH: 53
<212> TYPE: DNA
<213> ORGANISM: Lactococcus lactis

<400> SEQUENCE: 4
aacccacgtc gatcgtgaac acatccataa ccatatcatt tttaattcta cga    53

<210> SEQ ID NO 5
<211> LENGTH: 2761
<212> TYPE: DNA
<213> ORGANISM: Lactococcus lactis

<400> SEQUENCE: 5

| | | |
|---|---|---|
| aagcttagag aaaaataatg cggtgcttgg tcatcacctc atccaatcat tttctcctga | 60 |
| tgacaatcta actcctgaac aaattcatga ataggtcgt caaaccatat tagaatttac | 120 |
| aggtggcgaa tatgaatttg tgattgcaac ccacgtcgat cgtgaacaca tccataacgt | 180 |
| gcgcccagat agggtgttaa gtcaagtagt ttaaggtact actctgtaag ataacacaga | 240 |
| aaacagccaa cctaaccgaa aagcgaaagc tgatacggga acagagcacg gttggaaagc | 300 |
| gatgagttac ctaaagacaa tcgggtacga ctgagtcgca atgttaatca gatataaggt | 360 |
| ataagttgtg tttactgaac gcaagtttct aatttcggtt atgtgtcgat agaggaaagt | 420 |
| gtctgaaacc tctagtacaa agaaaggtaa gttatggttg tggacttatc tgttatcacc | 480 |
| acatttgtac aatctgtagg agaacctatg gaacgaaac gaaagcgatg ccgagaatct | 540 |
| gaatttacca agacttaaca ctaactgggg atacccctaaa caagaatgcc taatagaaag | 600 |
| gaggaaaaag gctatagcac tagagcttga aaatcttgca agggtacgga gtactcgtag | 660 |
| tagtctgaga agggtaacgc cctttacatg gcaaaggggt acagttattg tgtactaaaa | 720 |
| ttaaaaattg attagggagg aaaacctcaa atgaaaacca acaatggcaa ttttagaaag | 780 |
| aatcagtaaa aattcacaag aaaatataga cgaagttttt acaagacttt atcgttatct | 840 |
| tttacgtcca gatatttatt acgtggcgta tcaaaattta tattccaata aaggagcttc | 900 |
| cacaaaagga atattagatg atacagcgga tggctttagt gaagaaaaaa taaaaaagat | 960 |
| tattcaatct ttaaaagacg gaacttacta tcctcaacct gtacgaagaa tgtatattgc | 1020 |
| aaaaaagaat tctaaaaaga tgagacccttt aggaattcca actttcacag ataaattgat | 1080 |
| ccaagaagct gtgagaataa ttcttgaatc tatctatgaa ccggtattcg aagatgtgtc | 1140 |
| tcacggtttt agacctcaac gaagctgtca cacagctttg aaaacaatca aaagagagtt | 1200 |
| tggcggcgca agatggtttg tggagggaga tataaaaggc tgcttcgata atatagacca | 1260 |

-continued

```
cgttacactc attggactca tcaatcttaa aatcaaagat atgaaaatga gccaattgat    1320
ttataaattt ctaaaagcag gttatctgga aaactggcag tatcacaaaa cttacagcgg    1380
aacacctcaa ggtggaattc tatctcctct tttggccaac atctatcttc atgaattgga    1440
taagtttgtt ttacaactca aaatgaagtt tgaccgagaa agtccagaaa gaataacacc    1500
tgaatatcgg gaacttcaca atgagataaa aagaatttct caccgtctca agaagttgga    1560
gggtgaagaa aaagctaaag ttcttttaga atatcaagaa aaacgtaaaa gattacccac    1620 actccctgt  acctcacaga caaataaagt attgaaatac gtccggtatg cggacgactt    1680
cattatctct gttaaaggaa gcaaagagga ctgtcaatgg ataaaagaac aattaaaact    1740
ttttattcat aacaagctaa aatggaatt  gagtgaagaa aaaacactca tcacacatag    1800
cagtcaaccc gctcgttttc tgggatatga tatacgagta aggagaagtg gaacgataaa    1860
acgatctggt aaagtcaaaa agagaacact caatgggagt gtagaactcc ttattcctct    1920
tcaagacaaa attcgtcaat ttattttga  caagaaaata gctatccaaa agaaagatag    1980
ctcatggttt ccagttcaca ggaaatatct tattcgttca acagacttag aaatcatcac    2040
aatttataat tctgaattaa gagggatttg taattactac ggtctagcaa gtaattttaa    2100
ccagctcaat tatttttgctt atcttatgga atacagctgt ctaaaaacga tagcctccaa    2160
acataaggga acactttcaa aaaccatttc catgtttaaa gatggaagtg gttcgtgggg    2220
catcccgtat gagataaagc aaggtaagca gcgccgttat tttgcaaatt ttagtgaatg    2280
taaatcccct tatcaattta cggatgagat aagtcaagct cctgtattgt atggctatgc    2340
ccggaatact cttgaaaaca ggttaaaagc taaatgttgt gaattatgtg aacatctga    2400 tgaaaatact tcctatgaaa ttcaccatgt caataaggtc aaaaatctta aaggcaaaga    2460
aaaatgggaa atggcaatga tagcgaaaca acgtaaaact cttgttgtat gctttcattg    2520
tcatcgtcac gtgattcata acacaagtg  aatttttacg aacgaacaat aacagagccg    2580
tatactccga gaggggtacg tacggttccc gaagagggtg gtgcaaacca gtcacagtaa    2640
tgtgaacaag gcggtacctc cctacttcac catatcattt ttaattctac gaatctttat    2700
actggcaaac aatttgactg gaaagtcatt cctaaagaga aaacaaaaag cggcaaagct    2760
t                                                                    2761
```

<210> SEQ ID NO 6
<211> LENGTH: 599
<212> TYPE: PRT
<213> ORGANISM: Lactococcus lactis

<400> SEQUENCE: 6

```
Met Lys Pro Thr Met Ala Ile Leu Glu Arg Ile Ser Lys Asn Ser Gln
 1               5                  10                  15

Glu Asn Ile Asp Glu Val Phe Thr Arg Leu Tyr Arg Tyr Leu Leu Arg
            20                  25                  30

Pro Asp Ile Tyr Tyr Val Ala Tyr Gln Asn Leu Tyr Ser Asn Lys Gly
        35                  40                  45

Ala Ser Thr Lys Gly Ile Leu Asp Asp Thr Ala Asp Gly Phe Ser Glu
    50                  55                  60

Glu Lys Ile Lys Lys Ile Ile Gln Ser Leu Lys Asp Gly Thr Tyr Tyr
65                  70                  75                  80

Pro Gln Pro Val Arg Arg Met Tyr Ile Ala Lys Lys Asn Ser Lys Lys
                85                  90                  95
```

-continued

```
Met Arg Pro Leu Gly Ile Pro Thr Phe Thr Asp Lys Leu Ile Gln Glu
            100                 105                 110
Ala Val Arg Ile Leu Leu Glu Ser Ile Tyr Glu Pro Val Phe Glu Asp
            115                 120                 125
Val Ser His Gly Phe Arg Pro Gln Arg Ser Cys His Thr Ala Leu Lys
            130                 135             140
Thr Ile Lys Arg Glu Phe Gly Gly Ala Arg Trp Phe Val Glu Gly Asp
145                 150                 155                 160
Ile Lys Gly Cys Phe Asp Asn Ile Asp His Val Thr Leu Ile Gly Leu
                165                 170                 175
Ile Asn Leu Lys Ile Lys Asp Met Lys Met Ser Gln Leu Ile Tyr Lys
            180                 185                 190
Phe Leu Lys Ala Gly Tyr Leu Glu Asn Trp Gln Tyr His Lys Thr Tyr
            195                 200                 205
Ser Gly Thr Pro Gln Gly Gly Ile Leu Ser Pro Leu Leu Ala Asn Ile
            210                 215                 220
Tyr Leu Glu His Leu Asp Lys Phe Val Leu Gln Leu Lys Met Lys Phe
225                 230                 235                 240
Asp Arg Glu Ser Pro Glu Arg Ile Thr Pro Glu Tyr Arg Glu Leu His
                245                 250                 255
Asn Glu Ile Lys Arg Ile Ser His Arg Leu Lys Lys Leu Glu Gly Glu
            260                 265                 270
Glu Lys Ala Lys Val Leu Leu Glu Tyr Gln Glu Lys Arg Lys Arg Leu
            275                 280                 285
Pro Thr Leu Pro Cys Thr Ser Gln Thr Asn Lys Val Leu Lys Tyr Val
            290                 295                 300
Arg Tyr Ala Asp Asp Phe Ile Ile Ser Val Lys Gly Ser Lys Glu Asp
305                 310                 315                 320
Cys Gln Trp Ile Lys Glu Gln Leu Lys Leu Pro Ile His Asn Lys Leu
                325                 330                 335
Lys Met Glu Leu Ser Glu Glu Lys Thr Leu Ile Thr His Ser Ser Gln
            340                 345                 350
Pro Ala Arg Phe Leu Gly Tyr Asp Ile Arg Val Arg Arg Ser Gly Thr
            355                 360                 365
Ile Lys Arg Ser Gly Lys Val Lys Lys Arg Thr Leu Asn Gly Ser Val
            370                 375                 380
Glu Leu Leu Ile Pro Leu Gln Asp Lys Ile Arg Gln Phe Ile Phe Asp
385                 390                 395                 400
Lys Lys Ile Ala Ile Gln Lys Lys Asp Ser Ser Trp Phe Pro Val His
                405                 410                 415
Arg Lys Tyr Leu Ile Arg Ser Thr Asp Leu Glu Ile Ile Thr Ile Tyr
            420                 425                 430
Asn Ser Glu Leu Arg Gly Ile Cys Asn Tyr Tyr Gly Leu Ala Ser Asn
            435                 440                 445
Phe Asn Gln Leu Asn Tyr Phe Ala Tyr Leu Met Glu Tyr Ser Cys Leu
            450                 455                 460
Lys Thr Ile Ala Ser Lys His Lys Gly Thr Leu Ser Lys Thr Ile Ser
465                 470                 475                 480
Met Phe Lys Asp Gly Ser Gly Ser Trp Gly Ile Pro Tyr Glu Ile Lys
                485                 490                 495
Gln Gly Lys Gln Arg Arg Tyr Phe Ala Asn Phe Ser Glu Cys Lys Ser
            500                 505                 510
Pro Tyr Gln Phe Thr Asp Glu Ile Ser Gln Ala Pro Val Leu Tyr Gly
```

```
            515                 520                 525
Tyr Ala Arg Asn Thr Leu Glu Asn Arg Leu Lys Ala Lys Cys Cys Glu
            530                 535                 540

Leu Cys Gly Thr Ser Asp Glu Asn Thr Ser Tyr Glu Ile His His Val
545                 550                 555                 560

Asn Lys Val Lys Asn Leu Lys Gly Lys Glu Lys Trp Glu Met Ala Met
                565                 570                 575

Ile Ala Lys Gln Arg Lys Thr Leu Val Val Cys Phe His Cys His Arg
            580                 585                 590

His Val Ile His Lys His Lys
            595

<210> SEQ ID NO 7
<211> LENGTH: 777
<212> TYPE: PRT
<213> ORGANISM: S. cerevisiae

<400> SEQUENCE: 7

Ala Pro Thr Ser Ala Tyr Ile Ser Leu Met Arg Thr Ala Leu Val Leu
  1               5                  10                  15

Trp Ile Ile Asn Arg Tyr Leu Lys His Met Thr Asn Ser Val Gly Ala
                 20                  25                  30

Asn Phe Thr Gly Ile Met Ala Cys His Lys Thr Pro Met Ile Ser Val
             35                  40                  45

Gly Gly Val Lys Cys Tyr Met Val Arg Leu Thr Asn Phe Leu Gln Val
         50                  55                  60

Phe Ile Arg Ile Thr Ile Ser Ser Tyr His Leu Asp Met Val Lys Gln
 65                  70                  75                  80

Val Trp Leu Pro Tyr Val Glu Val Ile Arg Leu Trp Phe Ile Val Leu
                 85                  90                  95

Asp Ser Thr Gly Ser Val Lys Lys Met Lys Asp Thr Asn Asn Thr Lys
            100                 105                 110

Gly Asn Thr Lys Ser Glu Gly Ser Thr Glu Arg Gly Asn Ser Trp Val
        115                 120                 125

Asp Arg Gly Met Val Val Pro Asn Thr Gln Met Lys Met Arg Phe Leu
130                 135                 140

Asn Gln Val Arg Tyr Tyr Ser Val Asn Asn Asn Leu Lys Met Gly Lys
145                 150                 155                 160

Asp Thr Asn Ile Glu Leu Ser Lys Asp Thr Ser Thr Ser Asp Leu Leu
                165                 170                 175

Glu Phe Glu Lys Leu Val Met Asp Asn Met Asn Asp Asp Asn Met Asn
            180                 185                 190

Asn Asn Leu Leu Ser Ile Met Lys Asn Val Asp Met Leu Met Leu Ala
        195                 200                 205

Tyr Asn Arg Ile Lys Ser Lys Pro Gly Asn Met Thr Pro Gly Thr Thr
    210                 215                 220

Leu Glu Thr Leu Asp Gly Met Asn Met Met Tyr Leu Asn Lys Leu Ser
225                 230                 235                 240

Asn Glu Leu Gly Thr Gly Lys Phe Lys Phe Lys Pro Met Arg Met Val
                245                 250                 255

Asn Ile Pro Lys Pro Lys Gly Gly Met Arg Pro Leu Ser Val Gly Asn
            260                 265                 270

Pro Arg Asp Lys Ile Val Gln Glu Val Met Arg Met Ile Leu Asp Thr
        275                 280                 285
```

-continued

```
Ile Phe Asp Lys Lys Ser Met Thr His Ser His Gly Phe Arg Lys Asn
    290                 295                 300

Met Ser Cys Gln Thr Ala Ile Trp Glu Val Arg Asn Met Phe Gly Gly
305                 310                 315                 320

Ser Asn Trp Phe Ile Glu Val Asp Leu Lys Lys Cys Phe Asp Thr Ile
                325                 330                 335

Ser His Asp Leu Ile Ile Lys Glu Leu Lys Arg Tyr Ile Ser Asp Lys
            340                 345                 350

Gly Phe Ile Asp Leu Val Tyr Lys Leu Leu Arg Ala Gly Tyr Ile Asp
        355                 360                 365

Glu Lys Gly Thr Tyr His Lys Pro Met Leu Gly Leu Pro Gln Gly Ser
    370                 375                 380

Leu Ile Ser Pro Ile Leu Cys Asn Ile Val Met Thr Leu Val Asp Asn
385                 390                 395                 400

Trp Leu Glu Asp Tyr Ile Asn Leu Tyr Asn Lys Gly Lys Val Lys Lys
                405                 410                 415

Gln His Pro Thr Tyr Lys Lys Leu Ser Arg Met Ile Ala Lys Ala Lys
            420                 425                 430

Met Phe Ser Thr Arg Leu Lys Leu His Lys Glu Arg Ala Lys Gly Pro
        435                 440                 445

Thr Phe Ile Tyr Asn Asp Pro Asn Phe Lys Arg Met Lys Tyr Val Arg
    450                 455                 460

Tyr Ala Asp Asp Ile Leu Ile Gly Val Leu Gly Ser Lys Asn Asp Cys
465                 470                 475                 480

Lys Met Ile Lys Arg Asp Leu Asn Asn Phe Leu Asn Ser Leu Gly Leu
                485                 490                 495

Thr Met Asn Glu Glu Lys Thr Leu Ile Thr Cys Ala Thr Glu Thr Pro
            500                 505                 510

Ala Arg Phe Leu Gly Tyr Asn Ile Ser Ile Thr Pro Leu Lys Arg Met
        515                 520                 525

Pro Thr Val Thr Lys Thr Ile Arg Gly Lys Thr Ile Arg Ser Arg Asn
530                 535                 540

Thr Thr Arg Pro Ile Ile Asn Ala Pro Ile Arg Asp Ile Ile Asn Lys
545                 550                 555                 560

Leu Ala Thr Asn Gly Tyr Cys Lys His Asn Lys Asn Gly Arg Met Gly
                565                 570                 575

Val Pro Thr Arg Val Gly Arg Trp Thr Tyr Glu Glu Pro Arg Thr Ile
            580                 585                 590

Ile Asn Asn Tyr Lys Ala Leu Gly Arg Gly Ile Leu Asn Tyr Tyr Lys
        595                 600                 605

Leu Ala Thr Asn Tyr Lys Arg Leu Arg Asp Arg Ile Tyr Tyr Val Leu
    610                 615                 620

Tyr Tyr Ser Cys Val Leu Thr Leu Ala Ser Lys Tyr Arg Leu Lys Thr
625                 630                 635                 640

Met Ser Lys Thr Ile Lys Lys Phe Gly Tyr Asn Leu Asn Ile Ile Glu
                645                 650                 655

Asn Asp Lys Leu Ile Ala Asn Phe Pro Arg Asn Thr Phe Asp Asn Ile
            660                 665                 670

Lys Lys Ile Glu Asn His Gly Met Phe Met Tyr Met Ser Glu Ala Lys
        675                 680                 685

Val Thr Asp Pro Phe Glu Tyr Ile Asp Ser Ile Lys Tyr Met Leu Pro
    690                 695                 700

Thr Ala Lys Ala Asn Phe Asn Lys Pro Cys Ser Ile Cys Asn Ser Thr
```

-continued

```
                705                 710                 715                 720
Ile Asp Val Glu Met His His Val Lys Gln Leu His Arg Gly Met Leu
                    725                 730                 735

Lys Ala Thr Lys Asp Tyr Ile Thr Gly Arg Met Ile Thr Met Asn Arg
                740                 745                 750

Lys Gln Ile Pro Leu Cys Lys Gln Cys His Ile Lys Thr His Lys Asn
            755                 760                 765

Lys Phe Lys Asn Met Gly Pro Gly Met
        770                 775

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:
      Modifications to Full-Lenght Sequence

<400> SEQUENCE: 8
catcacgtaa ga                                                              12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence:
      Modifications to Full-Lenght Sequence

<400> SEQUENCE: 9
gcagctgcag ct                                                              12

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:
      Modifications to Full-Lenght Sequence

<400> SEQUENCE: 10
gtcatgctgt attaatga                                                        18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:
      Modifications to Full-Lenght Sequence

<400> SEQUENCE: 11
atggtaattc acaattat                                                        18

<210> SEQ ID NO 12
<211> LENGTH: 785
<212> TYPE: PRT
<213> ORGANISM: S. cerevisiae

<400> SEQUENCE: 12

Ala Pro Phe Arg Leu Ile Tyr His Cys Ile Glu Val Leu Ile Asp Lys
 1               5                  10                  15

His Ile Ser Val Tyr Ser Ile Asn Glu Asn Phe Thr Val Ser Phe Trp
            20                  25                  30
```

-continued

```
Phe Trp Leu Leu Val Val Thr Tyr Met Val Phe Arg Tyr Val Asn His
         35                  40                  45
Met Ala Tyr Pro Val Gly Ala Asn Ser Thr Gly Thr Met Ala Cys His
         50                  55                  60
Lys Ser Ala Gly Val Lys Gln Pro Ala Gln Gly Lys Asn Cys Pro Met
 65                  70                  75                  80
Ala Arg Leu Thr Asn Ser Cys Lys Glu Cys Leu Gly Phe Ser Leu Thr
                     85                  90                  95
Pro Ser His Leu Gly Ile Val Ile His Tyr Val Leu Glu Glu
                100                 105                 110
Val His Glu Leu Thr Lys Asn Glu Ser Leu Ala Leu Ser Lys Ser Trp
         115                 120                 125
His Leu Glu Gly Cys Thr Ser Ser Asn Gly Lys Leu Arg Asn Thr Gly
         130                 135                 140
Leu Ser Glu Arg Gly Asn Pro Gly Asp Asn Gly Val Phe Met Val Pro
145                 150                 155                 160
Lys Phe Asn Leu Asn Lys Ala Arg Tyr Phe Ser Thr Leu Ser Lys Leu
                165                 170                 175
Asn Ala Arg Lys Glu Asp Ser Leu Ala Tyr Leu Thr Lys Ile Asn Thr
                180                 185                 190
Thr Asp Phe Ser Glu Leu Asn Lys Leu Met Glu Asn Asn His Asn Lys
         195                 200                 205
Thr Glu Thr Ile Asn Thr Arg Ile Leu Lys Leu Met Ser Asp Ile Arg
         210                 215                 220
Met Leu Leu Ile Ala Tyr Asn Lys Ile Lys Ser Lys Lys Gly Asn Met
225                 230                 235                 240
Ser Lys Gly Ser Asn Asn Ile Thr Leu Asp Gly Ile Asn Ile Ser Tyr
                245                 250                 255
Leu Asn Lys Leu Ser Lys Asp Ile Asn Thr Asn Met Phe Lys Phe Ser
                260                 265                 270
Pro Val Arg Arg Val Glu Ile Pro Lys Thr Ser Gly Gly Phe Arg Pro
         275                 280                 285
Leu Ser Val Gly Asn Pro Arg Glu Lys Ile Val Gln Glu Ser Met Arg
         290                 295                 300
Met Met Leu Glu Ile Ile Tyr Asn Asn Ser Phe Ser Tyr Tyr Ser His
305                 310                 315                 320
Gly Phe Arg Pro Asn Leu Ser Cys Leu Thr Ala Ile Ile Gln Cys Lys
                325                 330                 335
Asn Tyr Met Gln Tyr Cys Asn Trp Phe Ile Lys Val Asp Leu Asn Lys
                340                 345                 350
Cys Phe Asp Thr Ile Pro His Asn Met Leu Ile Asn Val Leu Asn Glu
         355                 360                 365
Arg Ile Lys Asp Lys Gly Phe Met Asp Leu Leu Tyr Lys Leu Leu Arg
         370                 375                 380
Ala Gly Tyr Val Asp Lys Asn Asn Tyr His Asn Thr Thr Leu Gly
385                 390                 395                 400
Ile Pro Gln Gly Ser Val Val Ser Pro Ile Leu Cys Asn Ile Phe Leu
                405                 410                 415
Asp Lys Leu Asp Lys Tyr Leu Glu Asn Lys Phe Glu Asn Glu Phe Asn
                420                 425                 430
Thr Gly Asn Met Ser Asn Arg Gly Arg Asn Pro Ile Tyr Asn Ser Leu
         435                 440                 445
```

-continued

```
Ser Ser Lys Ile Tyr Arg Cys Lys Leu Leu Ser Glu Lys Leu Lys Leu
    450                 455                 460

Ile Arg Leu Arg Asp His Tyr Gln Arg Asn Met Gly Ser Asp Lys Ser
465                 470                 475                 480

Phe Lys Arg Ala Tyr Phe Val Arg Tyr Ala Asp Asp Ile Ile Ile Gly
                485                 490                 495

Val Met Gly Ser His Asn Asp Cys Lys Asn Ile Leu Asn Asp Ile Asn
            500                 505                 510

Asn Phe Leu Lys Glu Asn Leu Ser Ile Val Met Lys Leu Asn Lys His
        515                 520                 525

Gly Tyr Cys Ser His Gly Ile Leu Gly Lys Pro Gly Met Ser Ile Asn
    530                 535                 540

Met Asp Lys Ser Val Ile Lys His Ser Lys Glu Gly Val Ser Phe Leu
545                 550                 555                 560

Gly Tyr Asp Val Lys Val Thr Pro Trp Glu Lys Arg Pro Tyr Arg Met
                565                 570                 575

Ile Lys Lys Gly Asp Asn Phe Ile Arg Val Arg His His Thr Ser Leu
            580                 585                 590

Val Val Asn Ala Pro Ile Arg Arg Gly Val Gly Arg Leu Ile His Cys
        595                 600                 605

Glu Met Lys Thr Ile Leu Met His Tyr Leu Ala Val Gly Arg Gly Ile
    610                 615                 620

Met Asn Tyr Tyr Arg Leu Ala Thr Asn Phe Thr Thr Leu Arg Gly Arg
625                 630                 635                 640

Ile Thr Tyr Ile Leu Phe Tyr Ser Cys Cys Leu Thr Leu Ala Arg Lys
                645                 650                 655

Phe Lys Leu Asn Thr Val Lys Lys Val Ile Leu Lys Phe Gly Lys Val
            660                 665                 670

Leu Val Asp Pro His Ser Lys Val Ser Phe Ser Ile Asp Asp Phe Lys
        675                 680                 685

Ile Arg His Lys Met Asn Met Thr Asp Ser Asn Tyr Thr Pro Asp Glu
    690                 695                 700

Ile Leu Asp Arg Tyr Lys Tyr Met Leu Pro Arg Ser Leu Ser Leu Phe
705                 710                 715                 720

Ser Gly Ile Cys Gln Ile Cys Gly Ser Lys His Asp Leu Glu Val His
                725                 730                 735

His Val Arg Thr Leu Asn Asn Ala Ala Asn Lys Ile Lys Asp Asp Tyr
            740                 745                 750

Leu Leu Gly Arg Met Ile Lys Met Asn Arg Lys Gln Ile Thr Ile Cys
        755                 760                 765

Leu Thr Cys His Phe Lys Val His Gln Gly Leu Tyr Asn Gly Pro Gly
    770                 775                 780

Leu
785
```